US009683041B2

(12) United States Patent
Spee et al.

(10) Patent No.: US 9,683,041 B2
(45) Date of Patent: Jun. 20, 2017

(54) ANTI-NKG2A ANTIBODIES AND USES THEREOF

(71) Applicant: NOVO NORDISK A/S, Bagsvaerd (DK)

(72) Inventors: Petrus Johannes Louis Spee, Alleroed (DK); Soeren Berg Padkaer, Vaerlose (DK)

(73) Assignee: NOVO NORDISK A/S, Bagsvaerd (DK)

(*) Notice: Subject to any disclaimer, the term of this patent is extended or adjusted under 35 U.S.C. 154(b) by 0 days.

(21) Appl. No.: 14/548,327

(22) Filed: Nov. 20, 2014

(65) Prior Publication Data

US 2015/0071929 A1  Mar. 12, 2015

Related U.S. Application Data

(60) Division of application No. 13/477,888, filed on May 22, 2012, now Pat. No. 8,901,283, which is a continuation of application No. 12/305,683, filed as application No. PCT/EP2007/056485 on Jun. 28, 2007, now Pat. No. 8,206,709.

(60) Provisional application No. 60/818,550, filed on Jul. 5, 2006.

(30) Foreign Application Priority Data

Jun. 30, 2006  (EP) .................................. 06116429

(51) Int. Cl.
| A61K 39/395 | (2006.01) |
|---|---|
| C07K 16/28 | (2006.01) |
| C07K 16/46 | (2006.01) |
| A61K 39/00 | (2006.01) |

(52) U.S. Cl.
CPC ...... *C07K 16/2803* (2013.01); *C07K 16/2851* (2013.01); *C07K 16/468* (2013.01); *A61K 2039/505* (2013.01); *C07K 2316/96* (2013.01); *C07K 2317/24* (2013.01); *C07K 2317/31* (2013.01); *C07K 2317/56* (2013.01); *C07K 2317/565* (2013.01); *C07K 2317/73* (2013.01); *C07K 2317/76* (2013.01); *C07K 2317/92* (2013.01)

(58) Field of Classification Search
CPC ............ C07K 16/2803; C07K 16/2851; A61K 39/395; A61K 39/39558
See application file for complete search history.

(56) References Cited

U.S. PATENT DOCUMENTS

| 5,489,525 A | 2/1996 | Pastan |
| 5,876,950 A | 3/1999 | Siadak et al. |
| 5,994,524 A | 11/1999 | Matsushima et al. |
| 8,206,709 B2 | 6/2012 | Spee et al. |
| 2003/0095965 A1 | 5/2003 | Van Beneden et al. |
| 2003/0171280 A1 | 9/2003 | Soderstrom |
| 2005/0037002 A1 | 2/2005 | Velardi et al. |
| 2009/0208416 A1 | 8/2009 | Moretta et al. |
| 2011/0052606 A1 | 3/2011 | Spee et al. |
| 2011/0229486 A1 | 9/2011 | Moretta et al. |

FOREIGN PATENT DOCUMENTS

| CN | 1747969 A | 3/2006 |
| CN | 101107269 A | 1/2008 |
| EP | 1036327 A2 | 9/2000 |
| JP | 03112485 A | 5/1991 |
| JP | 03112486 A | 5/1991 |
| JP | 03112487 A | 5/1991 |
| JP | 2004-528824 A | 9/2004 |
| JP | 03112484 U | 8/2005 |
| WO | 99/28748 A2 | 6/1999 |
| WO | 01/71005 A2 | 9/2001 |
| WO | WO 02/05122 | 1/2002 |
| WO | 02/50122 | 6/2002 |
| WO | 03/008449 A1 | 1/2003 |
| WO | 03/095965 A2 | 11/2003 |
| WO | 2004/003019 A2 | 1/2004 |
| WO | 2004/056312 | 7/2004 |
| WO | 2005/009465 A1 | 2/2005 |
| WO | 2005/105849 A1 | 11/2005 |
| WO | 2006/070286 | 7/2006 |
| WO | 2007042573 A2 | 4/2007 |
| WO | 2008/009545 | 1/2008 |
| WO | 2009/092805 A1 | 7/2009 |

OTHER PUBLICATIONS

HogenEsch et al. J. Controlled Release 2012; 164:183-186.*
Pearson H., Nature News, "Tragic Drug Trial Spotlights Potent Molecule", Nature Mar. 17, 2006; www.nature.com/news/2006/060313/full/news060313-17.html.*
Benevolo et al., J. Translational Med. 2011; 9:184, pp. 1-10.*
Bossard et al., Int'l J. Cancer, 2011; 131:855-63.*
Freishtat et al., BMC Pulmonary Med. 2007; 7:14 pp. 1-6.*
Leavenworth et al., Proc. Nat'l Acad. Sci. 2010; 107:2562-67.*
Hagberg et al., Rheumatol. 2013; 52:1818-23.*
Chan & Carter, Nature Rev. Immunol, 2010; 10:301-316.*
Wischhusen et al, J. Neuropathol. Exp Neurol., 2005; 64: 523-528.*
Marin et al., Immunogentics 2003; 54:767-775.*
Ruggeri et al., Haematologica, 2016; 105:626-633.*
Nattermann et al., Am. J. Pathol. 2005; 10:95-107.*
Nattermann et al., Am. J. Pathol. 2005; 166:443-53.*
Casset et al., Biochemical and Biophysical Research Communications, "A Peptide Mimetic of an Anti-CD4 Monoclonal Antibody by Rational Design", 2003, vol. 307, pp. 198-205.

(Continued)

*Primary Examiner* — Jessica H Roark
(74) *Attorney, Agent, or Firm* — Saliwanchik, Lloyd & Eisenschenk

(57) ABSTRACT

Described herein are anti-NKG2A antibodies suitable for human therapy, including humanized versions of murine anti-NKG2A antibody Z270, as well as related methods and materials for producing and using such antibodies. Exemplary complementarity-determining regions (CDRs) sequences and sites for optional amino acid back-substitutions in framework region (FR) and/or CDRs of such antibodies are also described.

14 Claims, 29 Drawing Sheets

(56) References Cited

OTHER PUBLICATIONS

Chen et al., Journal of Molecular Biology., "Selection and Analysis of an Optimized Anti-VEGF Antibody: Crystal Structure of an Affinity-Matured FAB in Complex With Antigen", 1999, Volume -, No. 293, pp. 865-881.
De Pascalis et al., Journal of Immunology, "Grafting of "Abbreviated" Complementarity-Determining Regions Containing Specificity-Determining Residues Essential for Ligand Contact to Engineer a Less Immunogenic Humanized Monoclonal Antibody", 2002, vol. 169, pp. 3076-3084.
Gonzales Noreen E et al, Tumor Biology, "Minimizing the Immunogenicity of Antibodies for Clinical Application", 2005, vol. 26, No. 1, pp. 31-43.
Holm et al., Molecular Immunology, "Functional Mapping and Single Chain Construction of the Anti-Cytokeratin 8 Monoclonal Antibody TS1", 2007, vol. 44, pp. 1075-1084.
Kashmiri et al., Methods, "SDR Grafting—A New Approach to Antibody Humanization", 2005, vol. 36, No. 1, pp. 25-34.
Kumar et al., Journal of Biological Chemistry, "Molecular Cloning and Expression of the FABS of Human Autoantibodies in *Escherichia coli*", 2000, vol. 275, pp. 35129-35136.
MacCallum et al., Journal of Molecular Biology., "Antibody-Antigen Interactions: Contact Analysis and Binding Site Topography", 1996, vol. 262, pp. 732-745.
Rudikoff et al., Proceedings of the National Academy of Sciences of the USA, "Single Amino Acid Substitution Altering Antigen-Binding Specificity", 1982, vol. 79, pp. 1979-1983.
Smith-Gill et al., Journal of Immunology, "Contributions of Immunoglobulin Heavy and Light Chains to Antibody Specificity for Lysozyme and Two Haptens", 1987, vol. 139, pp. 4135-4144.
Song et al., Biochemical and Biophysical Research Communications, "Light Chain of Natural Antibody Plays a Dominant Role in Proten Antigen Binding", 2000, vol. 268, pp. 390-394.
Vajdos et al., Journal of Molecular Biology., "Comprehensive Functional Maps of the Antigenbiding Site of an Anti-ERBB2 Antibody Obtained With Shotgun Scanning Mutagenesis", 2002, vol. 320, pp. 415-428.
Ward et al., Nature, "Binding Activities of a Repertoire of Single Immunoglobulin Variable Domains Secreted From *Escherichia coli*", 1989, vol. 341, pp. 544-546.
Wu H. et al., Journal of Molecular Biology, "Humanization of a Murine Monoclonal Antibody by Simultaneous Optimization of Framework and CDR Residues", 1999, vol. 294, No. 1, pp. 151-162.
Derre et al., "Expression and Release of HLA-E by Melanoma Cells and Melanocytes: Potential Impact on the Response of Cytotoxic Effector Cells," Journal of Immunology, 2006, vol. 177, p. 3100-3107.
Coupel et al., "Expression and Release of Soluble HLA-E is an Immunoregulatory Feature of Endothelial Cell Activation." Blood, 2007, vol. 109, pp. 2806-2814.
Vance et al., "Recognition of the Class Ib Molecule Qa-1b by Putative Activating Receptors CD94/NKG2C and CD94/NKG2E on Mouse Natural Killer Cells," Journal of Experimental Medicine, 1999, vol. 190, pp. 1801-1812.
Carter, P. et al., "Humanization of an Anti-P185HER2 Antibody for Human Cancer Therapy," Proceedings of the National Academy of Sciences of the USA, 1992, vol. 89, No. 10, pp. 4285-4289.
Bagot et al., "Functional Inhibitory Receptors Expressed by a Cutaneous T-Cell Lymphoma-Specific Cytolytic Clonal T-Cell Population," Journal of Investigative Dermatology, 2000, vol. 115, No. 6, pp. 994-999.
Bagot et al., "CD4+ Cutaneous T-Cell Lymphoma Cells Express the p140-Killer Cell Immunoglobulin-like Receptor," Blood, 2001, vol. 97, No. 5, pp. 1388-1391.
Biassoni et al., "Molecular and Functional Characterization of NKG2D, NKp80, and NKG2C Triggering NK Cell Receptors in Rhesus and Cynomolgus Macaques: Monitoring of NK Cell Function During Simian HIV Infection," Journal of Immunology, 2005, vol. 174, pp. 5695-5705.

Carretero et al., "The CD94 and NKG2-A C-type Lectins Covalently Assemble to Form a Natural Killer Cell Inhibitory Receptor for HLA Class I Molecules," European Journal of Immunology, 1997, vol. 27, pp. 563-567.
Costa et al., "Differential Disappearance of Inhibitory Natural Killer Cell Receptors during HAART and Possible Impairment of HIV-1-Specific CD8 Cytotoxic T Lymphocytes," AIDS, 2001, vol. 15, pp. 965-974.
Haedicke et al., "Expression of CD94/NKG2A and Killer Immunoglobulin-Like Receptors in NK Cells and a Subset of Extranodal Cytotoxic T-cell Lymphomas," Blood, 2000, vol. 95, No. 11, pp. 3628-3630.
Kamarashev et al., "Differential Expression of Cytotoxic Molecules and Killer Cell Inhibitory Receptors in CD8+ and CD56+ Cutaneous Lymphomas," American Journal of Pathology, 2001, vol. 158, No. 5, pp. 1593-1598.
Le Bouteiller et al., "Engagement of CD160 Receptor by HLA-C is a Triggering Mechanism used by Circulating Natural Killer (NK) Cells to Mediate Cytotoxicity," Proceedings of the National Academy of Sciences in the USA, 2002, vol. 99, No. 26, pp. 16963-16968.
Mavilio et al., "Identification of NKG2A and NKp80 as Specific Natural Killer Cell Markers in Rhesus and Pigtailed Monkeys," Blood, 2005, vol. 106, No. 5, pp. 1718-1725.
Mingari et al., "HLA Class I-specific Inhibitory Receptors in Human T Lymphocytes: Interleukin 15-induced Expression of CD94/NKG2A in Superantigen- or Alloantigen-activiated CD8+ T Cells," Proceedings of the National Academy of Sciences of the USA, 1998, vol. 95, pp. 1172-1177.
Ponte, et al., "Inhibitory Receptors Sensing HLA-G1 Molecules in Pregnancy: Decidua-associated Natural Killer Cells Express LIR-1 and CD94/NKG2A and Acquire p49, and HLA-G1-Specific Receptor," Proceedings of the National Academy of Sciences of the USA, 1999, vol. 96, pp. 5674-5679.
Sivori et al., "CD94 Functions as a Natural Killer Cell Inhibitory Receptor for Different HLA Class I Alleles: Identification of the Inhibitory Form of CD94 by the Use of Novel Monoclonal Antibodies," European Journal of Immunology, 1996, vol. 26, pp. 2487-2492.
Sivori et al., "p46, a Novel Natural Killer Cell-specific Surface Molecule that Mediates Cell Activation," Journal of Experimental Medicine, 1997, vol. 186, No. 7, pp. 1129-1136.
Vacca et al., "Analysis of Natural Killer Cells Isolated from Human Decidua: Evidence that 2B4 (CD244) Functions as an Inhibitory Receptor and Blocks NK-cell Function," Blood, 2006, vol. 108, No. 13, pp. 4078-4085.
Vitale et al., "The Leukocyte Ig-like Receptor (LIR)-1 for the Cytomegalovirous UL18 Protein Displays a Broad Specificity for Different HLA Class I Alleles: Analysis of LIR-1+ NK Cell Clones," International Immunology, 1999, vol. 11, No. 1, pp. 29-35.
Voss et al., "Participation of the CD94 Receptor Complex in Costimulation of Human Natural Killer Cells," Journal of Immunology, 1998, vol. 160, pp. 1618-1626.
Zimmer et al., "Activity and Phenotype of Natural Killer Cells in Peptide Transporter (TAP)-deficient Patients (Type I Bare Lymphocyte Syndrome)," Journal of Experimental Medicine, 1998, vol. 187, No. 1, pp. 117-122.
Castriconi et al., "Shaping of Adaptive Immunity by Innate Interactions," C.R. Biologies, 2004, vol. 327, pp. 533-537.
Guma et al., "Imprint of Human Cytomegalovirus Infection on the NK Cell Receptor Repertoire," Blood, 2004, vol. 104, No. 12, pp. 3664-3671.
Gunturi et al., "The Role of CD94/NKG2 in Innate and Adaptive Immunity," Immunologic Research, 2004, vol. 30, No. 1, pp. 29-34.
Jinushi et al., "Negative Regulation of NK Cell Activities by Inhibitor Receptor CD94/NKG2A Leads to Altered NK Cell-Induced Modulation of Dendritic Cell Functions in Chronic Hepatitis C Virus Infection," The Journal of Immunology, 2004, vol. 173, pp. 6072-6081.
Llano et al., "Differential Effects of US2, US6, and US11 Human Ctyomegalovirus Proteins on HLA Class Ia and HLA-E Expression: Impact on Target Susceptibility to NK Cell Subsets," European Journal of Immunology, 2003, vol. 33, pp. 2744-2754.

(56) References Cited

OTHER PUBLICATIONS

Riteau et al., "HLA-G1 Co-Expression Boosts the HLA Class I-Mediated NK Lysis Inhibition," International Immunology, 2001, vol. 13, No. 2, pp. 193-201.
Ward et al., HLA-C and HLA-E Reduce Antibody-Dependent Natural Killer Cell-Mediated Cyotoxicity of HIV-Infected Primary T Cell Blasts, AIDS, 2004, vol. 18, pp. 1769-1779.
Pedersen et al., "Differential Expression of Inhibitory or Activating CD94/NKG2 Subtypes on MART-1-Reactive T Cells in Vitiligo Versus Melanoma: A Case Report," J. Invest. Derm., 2002, vol. 118, pp. 595-599.
Wu et al., "Multimerization of a chimeric anti-CD20 single-chain Fv-Fc fusion protein is mediated through variable domain exchange," Prot. Engin., 2001, vol. 14, pp. 1025-1033.
Author Guide, Blood, pp. 1-19, Aug. 30, 2010.
Instructions to Authors, European Journal of Immunology, pp. 1-6, 2009.
Gavilondo et al., "Antibody Engineering at the Millennium," Biotechniques, 2000, vol. 29, No. 1, pp. 128-145.
Moretta et al., Identification of Four Subsets of Human CD3-CD16+ Natural Killer (NK) Cells by the Expression of Clonally Distributed Functional Surface Molecules: Correlation between Subset Assignment of NK Clones and Ability to Mediate Specific Alloantigen Recognition, J. Exp. Med., 1990, vol. 172, pp. 1589-1598.
Cleland et al., "The Development of Stable Protein Formulations: A Close Look at Protein Aggregation, Deamidation, and Oxidation," Critical Reviews in Therapeutic Drug Carrier Systems, 1993, vol. 10, No. 4, pp. 307-377.
Sablitzky et al., "Molecular Basis of an Isogenic Anti-Idiotypic Response," The EMBO Journal, 1984, vol. 3, No. 12, pp. 3005-3012.
Soderstrom et al. CD94/NKG2 is the Predominant Inhibitory Receptor Involved in Recognition of HLA-G by Decidual and Peripheral Blood NK Cells. J of Immunology. 1997 vol. 159 pp. 1072-1075, Abstract only.
Petrie, E. J., et al. CD94-NKG2A recognition of human leukocyte antigen (HLA)-E bound to an HLA class I leader sequence (2008), J. Exp. Med. 205; 725-735.
NCBI Database, "Gene Bank IDS GI:20981680", dated Apr. 3, 2013.
NCBI Database, "Gene Bank IDS GI:116013", dated May 29, 2013.
Borrego et al., "The CD94/NKG2 Familty of Receptors," Imm. Res., 2006, vol. 35, No. 3, pp. 263-277.
Brooks et al., Journal of Experimental Medicine, "NKG2A Complexed With CD94 Defines a Novel Inhibitory Natural Killer Cell Receptor", 1997, vol. 185, No. 4, pp. 795-800.
Carretero M et al., European Journal of Immunology, "Specific Engagement of the CD94/NKG2-A Killer Inhibitory Receptor by the HLA-E Class IB Molecule Induces SHP-1 Phosphatase Recruitment to Tyrosine-Phosphorylated NKG2-A: Evidence . . . ", 1998, vol. 28, No. 4, pp. 1280-1291.
Casadevall A et al., Nature Reviews Microbiology, "Passive Antibody Therapy for Infectious Diseases", 2004, vol. 2, No. 9, pp. 695-703.
Coiffier B et al, The Hematology Journal, "Dose Intensity or Monoclonal Antibody I First-Line Treatment", 2004, vol. 5, Number -, pp. S154-S158.
Fang M et al., Immunity, "CD94 is Essential for NK Cell-Mediated Resistance to a Lethal Viral Disease", 2011, vol. 34, Number , pp. 579-589.
Gatto et al., Current medical Chemistry-Anti cancer Agents, "Mono Clonal Antibodies Cancer Theraphy", 2004, vol. 4, No. 5, pp. 411-414.
Hinoda et al., Cancer Science, "Monoclonal Antibodies as Effective Therapeutic Agents for Solid Tumors", 2004, vol. 95, No. 8, pp. 621-625.

Kaiser B K et al., Journal of Immunology, "Interactions Between NKG2X Immunoreceptors and HLA-E Ligands Display Overlapping Affinities and Thermodynamics", 2005, vol. 174, No. 5, pp. 2878-2884.
Kärre, K et al., Nature, "Selective Rejection of H-2-Deficient Lymphoma Variants Suggests Alternative Immune Defence Strategy", 1986, vol. 319, Number , pp. 675-678.
Ludewig B et al., Immunological Reviews., "Role of Dendritic Cells in the Induction and Maintenance of Autoimmune Diseases", 1999, vol. 169, Number , pp. 45-54.
Moretta, A et al, Annual Review of Immunology, "Activating Receptors and Coreceptors Involved in Human Natural Killer Cell-Mediated Cytolysis", 2001, vol. 19, Number -, pp. 197-223.
Martin et al., Immunogenetics, "The Genomic Organization and Evolution of the Natural Killer Immunoglobulin-Like Receptor (KIR) Gene Cluster", 2000, vol. 51, Number -, pp. 268-280.
Miller et al., Blood, "Human Natural Killer Cells With Polyclonal Lectin and Immunoglobulinlike Receptors Develop From Single Hematopoietic Stem Cells With Preferential Expression of NKG2A and KIR2DL2/L3/S2", 2001, vol. 98, No. 3, pp. 705-713.
Miller et al., Journal of Immunology, "Analysis of HLA-E Peptide-Binding Specificity and Contact Residues in Bound Peptide Required for Recognition by CD94/NKG2", 2003, vol. 171, Number , pp. 1369-1375.
Moretta A et al., Current Opinion in Immunology, "HLA Class I Specific Inhibitory Receptors", 1997, vol. 9, Number -, pp. 694-701.
Moretta L et al., The EMBO Journal, "Unravelling Natural Killer Cell Function: Triggering and Inhibitory Human NK Receptors", 2004, vol. 23, Number , pp. 255-259.
Ohlen C et al., Science, "Prevention of Allogeneic Bone Marrow Graft Rejection by H-2 Transgene in Donor Mice", 1989, vol. 246, Number , pp. 666-668.
Olszewski A j et al., Science STKE, "Empowering Targeted Therapy: Lessons From Rituximab", 2004, vol. 241, Number , pp. 1-6.
O'Neill et al., Blood, "Manipulating Dendritic Cell Biology for the Active Immunotherapy of Cancer", 2004, vol. 104, No. 8, pp. 2235-2246.
Ralph Mocikat et al., Immunity, "Natural Killer Cells Activated by MHC Class IIow Targets Prime Dendritic Cells to Induce Protective CD8 T Cell Responses", 2003, vol. 19, No. 4, pp. 561-569.
Ravetch et al., Science, "Immune Inhibitory Receptors", 2000, vol. 290, Number -, pp. 84-89.
Roit et al., New methods of Immunoassay,1991, pp. 65-75.
Roitt et al, Immunology, 2000, pp. 106-111.
Roitt et al, Immunology, 2000, pp. 530-535.
Sharma et al., The Journal of Pharmacology and Experimental Therapeutics, "Comparative Pharmacodynamics of Keliximab and Clenoliximab in Transgenic Mice Bearing Human CD4", 2000, vol. 293, No. 1, pp. 33-41.
Singer et al., Genes and Genomes,1998, vol. 1, pp. 63.
Lee et al., "HLA-E is a Major Ligand for the Natural Killer Inhibitory Receptor CD94/NKG2A," PNAS USA, 1998, vol. 95, pp. 5199-5204.
Van Beneden et al., Journal of Immunology, "Expression of LY49E and CD94/NKG2 on Fetal and Adult NK Cells", 2001, vol. 166, Number , pp. 4302-4311.
Yawata M et al., Critical Reviews in Immunology, "Variation Within the Human Killer Cell Immunoglobulin-Like Receptor(KIR) Gene Family", 2002, vol. 22, No. 5&6, pp. 463-482.
Zambello R et al., Blood, "Expression and Function of KIR and Natural Cytotoxicity Receptors in NK-Type Lymphoproliferative Diseases of Granular Lymphocytes", 2003, vol. 102, Number , pp. 1797-1805.
Le Bouteiller et al., Research in Immunology, "Antigen-Presenting Function(s) of the Non-Classical HLA-E,-F and -G Class I Molecules: The Beginning of a Story", 1996, vol. 147, No. 5, pp. 301-313.
Mingari, M.C et al., International Immunology, "Cytolytic I Lymphocytes Displaying Natural Killer . . . ", 1995, vol. 7, No. 4, pp. 697-703.
Roque et al. Biotechnology Progress. "Antibodies and Genetically Engineered Related Molecules" 2004 vol. 20(3) pp. 639-654.

(56) References Cited

OTHER PUBLICATIONS

Downs, S et al. "Development of Antibodies Specific for NKG2 Family Members." 2011. Depts. of Monoclonal Antibodies and antibody applications,R&D Systems Inc,Minneapolis MN,USA.
Aldrich et al., "Identification of Tap-Dependent Leader Peptide Recognized by Alloreactive T Cells Specific for a Class Ib Antigen," Cell, 1994, vol. 79, pp. 649-658.
Aramburu et al., "A Novel Function Cell Surface Dimer (Kp43) Expressed by Natural Killer Cells and T Cell Receptor-Gamma/Delta+ T Lymphocytes," The Journal of immunology, 1990, vol. 144, No. 8, pp. 3238-3247.
Borrego, Francisco et al., "Recognition of Human Histocompatability Leukocyte Antigen (HLA)-E Complexed with HLA Class I Signal Sequence-Derived Peptides by CD94/NKG2 Confers Protection from Natural Killer Cell-Mediated Lysis", Journal of Experimental Medicine, Mar. 2, 1998, vol. 187, No. 5, pp. 813-881.
Braud et al, TAP-and tapasin-dependent HLA-E Surface Expression Correlates with the Binding of an MHC Class Leader Peptide, Current Biology, 1998, vol. 8, No. 1, pp. 1-10.
Braud et al., "The Human Major Histocompatibility Complex Class Ib Molecule HLA-E Binds signal Sequence-derived Peptides with Primary Anchor Residues at Position 2 and 9," Eur. J. Immunol., 1997, vol. 27, pp. 1164-1169.
Braud et al., "HLA-E Binds to Natural Killer Cell Receptors CD94/NK02A, B and C," Nature (London), 1998, vol. 391, Vo. 6669, pp. 795-799.
Brooks et al., "Specific Recognition of HLA-E, But Not Classical, HLA Class I Molecules by Soluble CD94/NKG2A and NK Cells," Journal of Immunology, 1999, vol. 162, pp. 305-315.
Houchins et al., "DNA Sequence Analysis of NKG2, a Family of Related cDNA Clones Enclonding Type II Integral Membrane Proteins on Human Natural Killer Cells", J. Exp. Med., 1991, vol. 173, pp. 1017-1020.
Houchins et al., Natural Killer Cell Cytolytic Activity is Inhibited by NKG2-A and Activated by NKG2-C, The Journal of Immunology, 1997, vol. 158, pp. 3603-3609.
Lanier et al., "Arousal and Inhibition of Human NK Cells," Immunological Reviews, 1997, vol. 155, pp. 145-154.
Lanier et al., Immunoreceptor DAP12 Bearing a Tyrosine-Based Activation Motif is Involved in Activiating NK Cells, Nature 1998, vol. 391, pp. 703-707.
Lazetic et al., "Human Natural Killer Cell Receptors Involved in MHC Class I Recognition are Disulfide-Linked Heterokimers of CD94 and NKG2 Subunits," The Journal of Immunology, 1996, vol. 157, pp. 4741-4745.
Lee et al., "HLA-E Surface Expression Depends on Binding of TAP-Dependent Peptides Derived from Certain HLA Class I Signal Sequences," The Journal of Immunology, 1998, vol. 160, pp. 4951-4960.
Leibson, Paul J., "Cytotoxic Lymphocyle Recognition of HLA-E: Utilizing a Nonclassical Window to Peer into Classical MHC," Immunity, 1998, vol. 9, No. 3, pp. 289-294.
Llano et al., "HLA-EBound Peptides Influence Recognition by Inhibitory and Triggering CD94/NKG2 Receptors, Preferential Response to an HLQ-G Derived Nonamer," European Journal Immunology, 1998, vol. 29, No. 9, pp. 2854-2863.
O'Callaghan et al., "Structure and Funtion of the Human MHC Class Ib Molecules HLA-E, HLA-F and HLA-G," Immunol. Rev., 1998, vol. 163, pp. 129-138.
O'Callaghan et al., Structure Features Impose Tight Peptides Binding Specifically in teh Nonclassical MHC Molecule HLA-E, Molecular Cell, 1998, vol. 1, No. 4, pp. 531-541.
Perez-Villar et al., "Functional Ambivalence of the Kp43 (CD 94) NK Cell-Associated Surface Antigen," the Journal of Immunology, 1995, vol. 154, pp. 5779-5788.
Phillips et al., "CD94 and a Novel Associated Protein (94AP) Form a NK Cell Receptor Involved in the Recognition of HLA-A, HLA-B, and HLA-C Allotypes," Immunity, 1996, vol. 5, pp. 163-172.

Plougastel et al., "Cloning of NKG2-F, a New Member of the NKG2 Family of Human Natural Killer Cell Receptor Genes," Eur. J. Immunol., 1997, vol. 27, pp. 2835-2839.
Posch et al., "HLA-E is the Ligand for the Natural Killer Cell CD94/NK02 Receptors," Journal of Biomedical Science, 1998, vol. 5, No. 5, pp. 321-331.
Shawar et al., "Antigen Presentation by Major Histocompatibility Complex Class I-B Molecules," Annual Review of Immunology, 1994, vol. 12, pp. 839-880.
Sivori et al., "Inhibitory CD94 Molecules Identified by the Z199 Monoclonal Antibody Recognize Different HLA-Class I Molecules," Transplantation Proceedings, 1996, vol. 28, No. 6, pp. 3199-3203.
Ulbrecht et al., "The HLA-E Gene Encodes Two Differently Regulated Transcripts and a Cell Surface Protein," The Journal of Immunoloty, 1992, vol. 149, No. 9, pp. 2945-2953.
Ulbrecht et al., "Impaired Intracellular Transport and Cell Surface Expression of Nonpolymorphic HLA-E Evidence for Inefficient Peptide Building," J Exp Med, 1992, vol. 176, pp. 1083-1090.
Marshak-Rothstein et al., "Hybridoma proteins expressing the predominant idiotype of the antiazophenylarsonate response of A/J mice," PNAS, 1980, vol. 77, pp. 1120-1124.
Gessner et al., "The IgG Fc receptor family," 1998, Ann Hematol, vol. 76, pp. 231-248.
Reddy et al., "Elimination of Fc Receptor-Dependent Effector Functions of a Modified IgG4 Monoclonal Antibody to Human CD4," 2000, J. Immunol, vol. 164, pp. 1925-1933.
Yokoyama et al., "Immune functions encoded by the natural killer gene complex," 2003, Nature Rev Immunol, vol. 3, pp. 304-316.
Paul, Fundamental Immunology, 3rd Edition, 1993, pp. 292-295.
Brown et al., J. Immunol. 1996; 156(9):3285-91.
Arturo Casadevall et al., "Immunoglobulin Isotype Influences Affinity and Specificity," Proc Natl Acad Sci USA, 2012, vol. 109, No. 31, pp. 12272-12273.
Bottino, C. et al. "NTB-A, a Novel SH2D1A-associated Surface Molecule Contributing to the Inability of Natural Killer Cells to Kill Epstein-Barr Virus-infected B Cells in X-linked Lymphoproliferative Disease," J. Exp. Med., Aug. 6, 2001, pp. 235-246, vol. 194, No. 3.
Casadevall, A. et al. "Immunoglobulin isotype influences affinity and specificity," PNAS, Jul. 31, 2012, pp. 12272-12273, vol. 109, No. 31.
Cooper, M. A. et al. "NK cell and DC interactions," Trends in Immunology, Jan. 2004, pp. 47-52, vol. 25, No. 1.
D'Andrea, A. et al. "Regulation of T cell Lymphokine Production by killer Cell Inhibitory Receptor Recognition of Self HLA Class I Alleles," J. Exp. Med., Aug. 1996, pp. 789-794, vol. 184.
Demotte, N. et al. "A reversible functional defect of CD8+ T lymphocytes involving loss of tetramer labeling," Eur. J. Immunol., 2002, pp. 1688-1697, vol. 32.
Fauser, A. A. et al. "Guidelines for Anti-emetic Therapy: Acute Emesis," Eur. J. Canc., 1999, pp. 361-370, vol. 35, No. 3.
Leavenworth, J. W. et al. "Mobilization of natural killer cells inhibits development of collagen-induced arthritis," PNAS, Aug. 30, 2011, pp. 14584-14589, vol. 108, No. 35.
Lu, L. et al. "Regulation of Activated CD4+ T Cells by NK Cells via the Qa-1-NKG2A Inhibitory Pathway," Immunity, May 2007, pp. 593-604, vol. 26.
Mavilio, D. et al. "Natural killer cells in HIV-1 infection: Dichotomous effects of viremia on inhibitory and activating receptors and their functional correlates," PNAS, Dec. 9, 2003, pp. 15011-15016, vol. 100, No. 25.
Park, K.S. et al. "Inhibitory NKG2A and activating NKG2D and NKG2C natural killer cell receptor genes: susceptibility for rheumatoid arthritis," Tissue Antigens, 2008, pp. 342-346, vol. 72.
Pende, D. et al. "HLA-G recognition by human natural killer cells. Involvement of CD94 both as inhibitory and as activating receptor complex," Eur. J. Immunol., 1997, pp. 1875-1880, vol. 27.
Perez-Villar, J. J. et al. "The CD94/NKG2-A Inhibitory Receptor Complex is Involved in Natural Killer Cell-Mediated Recognition of Cells Expressing HLA-G1," The Journal of Immunology., 1997, pp. 5736-5743, vol. 158.

(56) References Cited

OTHER PUBLICATIONS

"PNAS Information for Authors," *PNAS*, Oct. 2013, pp. 1-6, vol. 110.
Presta, L. G. "Engineering of therapeutic antibodies to minimize immunogenicity and optimize function," *Advanced Drug Delivery Reviews*, 2006, pp. 640-656, vol. 58, No. 5-6.
Pridgeon, C. et al. "Natural killer cells in the synovial fluid of rheumatoid arthritis patients exhibit a CD56bright,CD94bright,CD158negative phenotype," *Rheumatology*, Apr. 16, 2003, pp. 870-878, vol. 42.
Teixeira De Matos, C. et al. "Activating and inhibitory receptors on synovial fluid natural killer cells of arthritis patients: role of CD94/NKG2A in control of cytokine secretion," *Immunology*, 2007, pp. 291-301, vol. 122.
Vance, R. E. et al. "Implications of CD94 deficiency and monoallelic NKG2A expression for natural killer cell development and repertoire formation," *PNAS*, Jan. 22, 2002, pp. 868-873, vol. 99, No. 2.
Vitale, C. et al. "Analysis of the activating receptors and cytolytic function of human natural killer cells undergoing in vivo differentiation after allogeneic bone marrow transplantation," *Eur. J. Immunol.*, 2004, pp. 455-460, vol. 34.
Zhang, A. L. et al. "Natural killer cells trigger differentiation of monocytes into dendritic cells," *Blood*, Oct. 1, 2007, pp. 2484-2493, vol. 110, No. 7.

\* cited by examiner

```
Light chain 1         2         3          4         5         6
  1       6789012345678901   4567ABCDEFG901234  789012345    01234567 9
  DIQMTQSPASLSASVGETVTITCRASE        NIYSYLAWYQQKQGKSPQFLVYNAKTLAEGVPS
  DIQMTQSPSSLSASVGDRVTITCRASQ        SISSYLNWYQQKPGKAPKLLIYAASSLQSGVPS
  DIQMTQSPSSLSASVGDRVTITCRASE        NIYSYLAWYQQKPGKAPKLLYNAKTLAEGVPS
  DIQMTQSPSSLSASVGDRVTITCRASE        NIYSYLAWYQQKPGKAPKXLXYNAKTLAEGVPS 7         8         9         10
  1 3   67 9 0 2345678901234567 9012345AB67 90123456789     <- The Kabat Scheme     SEQ ID NO:
  RFSGSGSGTQFSLKINSLQPEDFGSYYCQHHYGTP   RTFGGGIKLEIK       Z270VL                        1
  RFSGSGSGTDFTLTISSLQPEDFATYYCQQSYSTP   LTFGGGTKVEIK       VKI_O2/JK4                    9
  RFSGSGSGTDFTLTISSLQPEDFATYYCQHHYGTP   RTFGGGTKVEIK       humZ270VL1                    4
  RFSGSGSGTDFTLTISSLQPEDFATYYCQHHYGTP   RTFGGGTKVEIK       humZ270VL1cons                6

Heavy Chain 1         2         3          4         5         6
  1       6789012345678901       12345AB 7890123456 8 012ABC34567B90
  QVQLXQSGAEXXXPGASVKXSCKASGYTFTSYWMN    WVRQPQGLQWXGRIDP    YDSETHYX
  QVQLVQSGAEVKKPGASVKVSCKASGYTFTSYGIS    WVRQAPGQGLEWMGWISA  YNGNTNYA
  QVQLXQSGAEVKKPGASVKVSCKASGYTFTSYWMN    WVRQAPGQGLEWMGRIDP  YDSETHYA
  QVQLXQSGAEVKKPGASVKVSCKASGYTFTSYWMN    WVRQAPGQGLEWMGRIDP  YDSETHYX
  QVQLXQSGAEVKKPGASVKVSCKASGYTFTSYWMN    WVRQAPGQGLEWMGRIDP  YDSETHYX 7         8         9        10                11         SEQ ID NO:
  12345678   2 4    9012ABC345678901   567890ABCDEFGH1JK12 4567890  <- Kabat
  QK       T D S  STAYMLSLSD AVYYCARGGYDFDVGTLYWFF   DVWGXGTTVTVS  Z270VH                2
  QKLQGRVTMTDTSTSTAYMELRSLRSDDTAVYYCAR           YYYYYGM  DVWGQGTTVTVS  VH1_18/JH6       10
  QKLQGRVT T D S STAYMELRSLRSDDTAVYYCARGGYDFDVGTLYWFF DVWGQGTTVTVS  humZ270VH1            5
  QKLQGXVTXTDXSXSTAYMELRSLRSDDTAVYYCARGGYDFDVGTLYWFF DVWGQGTTVTVS  humZ270VH1cons        7
  QKXXXXXTXTDXSXSTAYMELRSLRSDDTAVYYCARGGYDFDVGTLYWFF DVWGQGTTVTVS  humZ270VH1cons2       8
```

Fig. 1

| | |
|---|---|
| CDR_L1 | RASENIYSYLA |
| CDR_L2 | NAKTLAE |
| CDR_L3 | QHHYGTPRT |
| CDR_H1 | SYWMN |
| CDR_H2 | RIDPYDSETHYAQKLQG |
| CDR_H3 | GGYDFDVGTLYWFFDV |

Fig. 2

Figure 4A  Z270 VL cDNA: (SEQ ID NO:14)

atgagtgtgcccactcagGTCCTGGGGTTGCTGCTGCTGTGGCTTACAGGTGCCAGATGTGACA
TCCAGATGACTCAGTCTCCAGCCTCCCTATCTGCATCTGTGGGAGAAACTGTCACCATC
ACATGTCGAGCAAGTGAGAATATTTACAGTTATTTAGCATGGTATCAGCAGAAACAGGG
AAAATCTCCTCAGTTCTTGGTCTATAATGCAAAAACCTTAGCAGAAGGTGTGCCATCAAG
GTTCAGTGGCAGTGGATCAGGCACACAGTTTTCTCTGAAGATCAACAGCCTGCAGCCTG
AAGATTTTGGGAGTTATTACTGTCAACATCACTATGGTACTCCTCGGACGTTCGGTGGA
GGCACCAAGCTGGAAATCAAA Figure 4B  Z270 VL protein (SEQ ID NO:15):

MSVPTQVLGLLLLWLTGARCDIQMTQSPASLSASVGETVTITCRASENIYSYL-
AWYQQKQGKSPQFLVYNAKTLAEGVPSRFSGSGSGTQFSL-
KINSLQPEDFGSYYCQHHYGTPRTFGGGTKLEIK

Figure 4C  Z270 VH cDNA (SEQ ID NO:16):

ATGGGATGGAGCTATATCATCCTCTTCTTGTTAGCAACAGCTACATGTGTCCAC-
TCCCAGGTCCAACTGCAGCAGCCTGGGGCTGAGCTGGTGAGGCCTGGGGCTTCAG-
TGAAGCTGTCCTGCAAGGCTTCTGGCTACACGTTCACCAGCTACTG-
GATGAACTGGGTTAAGCAGAGGCCTGAGCAAGGCCTTCAGTG-
GATTGGAAGGATTGATCCTTACGATAGTGAAACTCACTACAG-
TCAAAAGTTCAAGGACAAGGCCATATTGACTGTAGACAAATCCTCCAGCACAGCC-
TACATGCGACTCAGCAGCCTGACATCTGAGGACTCTGCGGTCTATTACTGTGCAA-
GAGGGGGCTATGATTTCGACGTAGGAACTCTCTACTGGTTCTTCGATGTCTGGGGCG-
CAGGGACCACGGTCACCGTCTCCTCA

Figure 4D  Z270 VH protein (SEQ ID NO:17):

MGWSYIILFLLATATCVHSQVQLQQPGAELVRPGASVKLSCK-
ASGYTFTSYWMNWVKQRPEQGLQWIGRIDPYDSETHYSQKFKDKAIL-
TVDKSSSTAYMRLSSLTSEDSAVYYCARGGYDFDVGTLYWFFDVWGAGTTVTVSS.

Z270 VL and IgG1 constant region (SEQ ID NO:18):
GAATTCgccaccatgagtgtgcccactcaggtcctgggggtt-
gctgctgctgtggcttacaggtgccagatgtgacatccagatgactcag-
tctccagcctccctatctgcatctgtgggagaaactgtcaccatcacatgtcgagcaagtga-
gaatatttacagttatttagcatggtatcagcagaaacagggaaaatctcctcagttctt-
ggtctataatgcaaaaaccttagcagaaggtgtgccatcaaggttcagtggcagtg-
gatcaggcacacagttttctctgaagatcaacagcctgcagcctgaagatttggggag-
ttattactgtcaacatcactatggtactcctcggacgttcggtggaggcaccaagctg-
gaaatcaaacgggctgatgctgcaccaactgtatccatcttcccaccatccagtgagcag-
ttaacatctggaggtgcctcagtcgtgtgcttcttgaacaacttctaccccaaaga-
catcaatgtcaagtggaagattgatggcagtgaacgacaaaatggcgtcctgaacagtt-
ggactgatcaggacagcaaagacagcacctacagcatgagcagcaccctcacgttgac-
caaggacgagtatgaacgacataacagctatacctgtgaggccactcacaaga-
catcaacttcacccattgtcaagagcttcaacaggaatgagtgttagGCTAGC

Figure 4E

Z270 H1 variable region and IgG1 constant region (SEQ ID NO:19):
gaattcGCCACCATGGGATGGAGCTATATCATCCTCTTCTTGTTAGCAACAGC-
TACATGTGTCCACTCCCAGGTCCAACTGCAG-
CAGCCTGGGGCTGAGCTGGTGAGGCCTGGGGCTTCAGTGAAGCTGTCCTG-
CAAGGCTTCTGGCTACACGTTCACCAGCTACTGGATGAACTGGGTTAA-
GCAGAGGCCTGAGCAAGGCCTTCAGTGGATTGGAAGGATTGATCCTTACGA-
TAGTGAAACTCACTACAGTCAAAAGTTCAAGGACAAGGCCATATTGACTGTAGA-
CAAATCCTCCAGCACAGCCTACATGCGACTCAGCAGCCTGACATCTGAG-
GACTCTGCGGTCTATTACTGTGCAAGAGGGGGCTATGATTTCGACGTAGGAACTCTC-
TACTGGTTCTTCGATGTCTGGGGCGCAGGGACCACGGTCACCGTCTCCTCAgccaaaac-
gacacccccatctgtctatccgctagccctggatctgctgcccaaactaactccatggtgaccctgggatgcctggtcaagggc-
gatctgctgcccaaactaactccatggtgaccctgggatgcctggtcaagggc-
tatttccctgagccagtgacagtgacctggaactctggatcctgtccagcggtgtgcacac-
cttcccagctgtcctgcagtctgacctctacactctgagcagctcagtgactgtcccctccag-
cacctggcccagcgagaccgtcacctgcaacgttgcccacccggccagcagcaccaaggtg-
gacaagaaaattgtgcccagggattgtggttgtaagccttgcatatgtacag-
tcccagaagtatcatctgtcttcatcttcccccaaagcccaaggatgtgctcac-
cattactctgactcctaaggtcacgtgtgttgtggtagacatcag-
caaggatgatcccgaggtccagttcagctggtttgtagatgatgtggaggtg-
cacacagctcagacgcaaccccgggaggagcagttcaacagcactttccgctcagtcag-
tgaacttcccatcatgcaccaggactggctcaatggcaaggag-
ttcaaatgcagggtcaacagtgcagctttccctgcccccatcgagaaaaccatctccaaaac-
caaaggcagaccgaaggctccacaggtgtacaccattccacctcccaaggag-
cagatggccaaggataaagtcagtctgacctgcatgataacagacttcttccctgaaga-
cattactgtggagtggcagtggaatgggcagccagcggagaactacaagaacac-
tcagcccatcatggacacagatggctcttacttcgtctacagcaagctcaatgtgcagaagag-
caactgggaggcaggaaatactttcacctgctctgtgttacatgagggcctgcacaaccacca-
tactgagaagagcctctcccactctcctggtaaatga.

Figure 4F

Z270VL sequence and human light chain (kappa) constant region (SEQ ID NO:20):

GAATTCgccaccatgagtgtgcccactcaggtcctggggtt-
gctgctgctgtggcttacaggtgccagatgtgacatccagatgactcag-
tctccagcctccctatctgcatctgtgggagaaactgtcaccatcacatgtcgagcaagtga-
gaatatttacagttatttagcatggtatcagcagaaacagggaaaatctcctcagttctt-
ggtctataatgcaaaaaccttagcagaaggtgtgccatcaaggttcagtggcagtg-
gatcaggcacacagttttctctgaagatcaacagcctgcagcctgaagattttgggag-
ttattactgtcaacatcactatggtactcctcggacgttcggtggaggcaccaagctg-
gaaatcaaacggactgtggcggcgccatctgtcttcatcttcccgccatctgatgagcagtt-
gaaatctggtaccgctagcgttgtgtgcctgctgaataacttctatcccaga-
gaggccaaagtacagtggaaggtggataacgccctccaatcgggtaactcccaggagag-
tgtcacagagcaggacagcaaggacagcacctacagcctcagcagcaccctgacgctgag-
caaagcagactacgagaaacacaaagtctac-
gcctgcgaagtcacccatcagggcctgagctcgcccgtcacaaagagcttcaacaggggagagtgttagGGATCC

Figure 4G

Z270 VH and human IgG4 heavy chain constant region (SEQ ID NO:21)
GAATTCgccaccatgggatggagctatatcatcctcttcttgttagcaacagc-
tacatgtgtccactcccaggtccaactgcag-
cagcctggggctgagctggtgaggcctggggcttcagtgaagctgtcctgcaaggcttctggc-
tacacgttcaccagctactggatgaactgggttaagcagaggcctgagcaaggccttcagtg-
gattggaaggattgatccttacgatagtgaaactcactacag-
tcaaaagttcaaggacaaggccatattgactgtagacaaatcctccagcacagcc-
tacatgcgactcagcagcctgacatctgaggactctgcggtctattactgtgcaagagggggc-
tatgatttcgacgtaggaactctctactggttcttcgatgtctggggcgcagggaccac-
ggtcaccgtctcctcaGCTAGCaccaagggcccatccgtcttccccctggcgccctgctccag-
gagcacctccgagagcacagccgccctgggctgcctggtcaaggactacttccccgaac-
cggtgacggtgtcgtggaactcaggcgccctgaccagcggcgtgcacaccttcccggctgtcc-
tacagtcctcaggactctactccctcagcagcgtggtgaccgtgccctccagcagcttggg-
cacgaagacctacacctgcaacgtagatcacaagcccagcaacaccaaggtggacaagagag-
ttgagtccaaatatggtcccccatgcccaccatgcccagcacctgagttcctggggggac-
catcagtcttcctgttccccccaaaacccaaggacactctcatgatctcccg-
gacccctgaggtcacgtgcgtggtggtggacgtgagccaggaagaccccgaggtccag-
ttcaactggtacgtggatggcgtggaggtgcataatgccaagacaaagccgcgggaggag-
cagttcaacagcacgtaccgtgtggtcagcgtcctcaccgtcctgcaccaggactggctgaacggcaaggagtacaagtg-
gactggctgaacggcaaggagtacaagtg-
caaggtctccaacaaaggcctcccgtcctccatcgagaaaaccatctccaaagccaaaggg-
cagccccgagagccacaggtgtacaccctgcccccatcccaggaggagatgaccaagaac-
caggtcagcctgacctgcctggtcaaaggcttctaccccagcgacatcgccgtggagtggga-
gagcaatgggcagccggagaacaactacaagaccacgcctcccgtgctggactccgac-
ggctccttcttcctctacagcaggctaaccgtggacaagagcaggtggcaggaggg-
gaatgtcttctcatgctccgtgatgcatgaggctctgcacaaccactacacacagaa-
gagcctctccctgtctctgggtaaatgaGGATCC.

Figure 4H

Z270 light chain CDRs grafted into VKI_02/JK4 template (SEQ ID NO:22):

gaattcgccaccatggacatgagggtccccgctcagctcctggggctcctgctactctggctccgaggtgccagatgtgacatcc agatgacccagtctccatcctccctgtctgcatctgtaggagacagagtcaccatcacttgcCGAGCAAGTGAGAATAT TTACAGTTATTTAGCAtggtatcagcagaaaccagggaaagcccctaagctcctgatctatAATGCAAAAACC TTAGCAGAAggggtcccatcaaggttcagtggcagtggatctgggacagatttcactctcaccatcagcagtctgcaacctg aagattttgcaacttactactgtCAACATCACTATGGTACTCCTCGGACGTTCGGCGGAGGGACCAA GGTGGAGATCAAAcggactgtggcggcgccatctgtcttcatcttcccgccatctgatgag-cagttgaaatctggtaccgctagcgttgtgtgcctgctgaataacttctatcccaga-gaggccaaagtacagtggaaggtggataacgccctccaatcgggtaactcccaggagag-tgtcacagagcaggacagcaaggacagcacctacagcctcagcagcaccctgacgctgag-caaagcagactacgagaaacacaaagtctac-gcctgcgaagtcacccatcagggcctgagctcgcccgtcacaaagagcttcaacaggggagagtgttag

Figure 4I

Z270 heavy chain CDRs with optimized CDR-H2 grafted into VH1_18/JK6 template (SEQ ID NO:23):

gaattcgccaccatggactggacctggagcatccttttcttggtggcagcag-
caacaggtgcccactcccaggttcagctggtgcagtctggagctgaggtgaagaa-
gcctggggcctcagtgaaggtctcctgcaaggcttctggttacacctttaccAGCTACTG-
GATGAACtgggtgcgacaggcccctggacaagggcttgagtggatgg-
gaAGGATTGATCCTTACGATAGTGAAACTCACtatgcacagaagctccagggcagagtcac-
catgaccacagacacatccacgagcacagcctacatggagctgaggagcctgagatctgac-
gacacggccgtgtattactgtgcgagaGGGGGCTATGATTTCGACGTAGGAACTCTC-
TACTGGTTCTTCGATGTCtggggccaagggacaacggtcaccgtctcttcagctagccac-
caagggcccatccgtcttccccctggcgccctgctccaggagcacctccgagag-
cacagccgccctgggctgcctggtcaaggactacttccccgaaccggtgacggtgtcgtg-
gaactcaggcgccctgaccagcggcgtgcacaccttcccggctgtcctacagtcctcag-
gactctactccctcagcagcgtggtgaccgtgccctccagcagcttgggcacgaagac-
ctacacctgcaacgtagatcacaagcccagcaacaccaaggtggacaagagagttgag-
tccaaatatggtcccccatgcccaccatgcccagcacctgagttcctggggggaccatcag-
tcttcctgttccccccaaaacccaaggacactctcatgatctcccggacccctgaggtcac-
gtgcgtggtggtggacgtgagccaggaagaccccgaggtccagttcaactggtacgtg-
gatggcgtggaggtgcataatgccaagacaaagccgcgggaggagcagttcaacagcac-
gtaccgtgtggtcagcgtcctcaccgtcctgcaccaggactggctgaacggcaaggag-
tacaagtgcaaggtctccaacaaaggcctcccgtcctccatcgagaaaaccatctccaaa-
gccaaagggcagccccgagagccacaggtgtacaccctgcccccatcccaggaggagatgac-
caagaaccaggtcagcctgacctgcctggtcaaaggcttctacccagcgacatcgccgtg-
gagtgggagagcaatgggcagccggagaacaactacaagaccacgcctcccgtgctg-
gactccgacggctccttcttcctctacagcaggctaaccgtggacaagagcaggtggcag-
gaggggaatgtcttctcatgctccgtgatgcatgaggctctgcacaaccactacacacagaa-
gagcctctccctgtctctgggtaaatga

Figure 4J

For transient expression

```
Heavy Chain
            1           2              3               4            5              6
1        6789012345678901         12345AB 7890123456 88 012ABC34567890
QVQLQQPGAELVRPGASVKLSCKASGYTFTSYWMN    WVKQRPEQGLQWIGRIDP   YDSETHYS
QVQLVQSGAEVKKPGASVKVSCKASGYTFTSYGIS    WVRQAPGQGLEWMGWISA   YNGNTNYA
QVQLVQSGAEVKKPGASVKVSCKASGYTFTSYWMN    WVRQAPGQGLEWMGRIDP   YDSETHYS
QVQLVQSGAEVKKPGASVKVSCKASGYTFTSYWMN    WVKQAPGQGLQWIGRIDP   YDSETHYS 7          8           9          10                 11                       SEQ ID NO:
    12345678   2 4      9012ABC345678901     567890ABCDEFGHIJK12 4567890  <- Kabat
QKFKDKAILTVDKSSSTAYMRLSSLTSEDSAVYYCARGGYDFDVGTLYWFF    DVWGAGTTVTVS  Z270VH        2
QKLQGRVTMTTDTSTSTAYMELRSLRSDDTAVYYCAR          YYYYYGM  DVWGQGTTVTVS  VHI_18/JH6   10
QKFKDRVTMTTDTSTSTAYMELRSLRSDDTAVYYCARGGYDFDVGTLYWFF    DVWGQGTTVTVS  humZ270VH3   24
QKFKDKATMTTDTSTSTAYMELRSLRSDDTAVYYCARGGYDFDVGTLYWFF    DVWGQGTTVTVS  humZ270VH4   25
```

Fig. 11

```
Heavy Chain
              1            2             3              4          5            6
    1        6789012345678901        12345AB 7890123456  8 012ABC34567890
    QVQLQQPGAELVRPGASVKLSCKASGYTFTSYWMN  WVKQRPEQGLQWIGRIDP  YDSETHYS
    QVQLVQSGAEVKKPGASVKVSCKASGYTFTSYWMN  WVRQAPGQGLEWMGRIDP  YDSETHYA
    EVQLVQSGAEVKKPGESLRISCKGSGYSFTSYWMN  WVRQMPGKGLEWMGRIDP  YDSETHYS
    EVQLVQSGAEVKKPGESLKISCKGSGYSFTSYWMN  WVRQMPGKGLEWMGRIDP  YDSETHYS
    EVQLVQSGAEVKKPGATVKISCKVSGYTFTSYWMN  WVQQAPGKGLEWMGRIDP  YDSETHYA
    QVQLVQSGAEVKKPGASVKVSCKASGYTFTSYWMN  WVRQAPGQGLEWMGRIDP  YDSETHYA 7            8             9             10         11                SEQ ID NO:
    1234567890          89012ABC34567890123 567890ABCDEFGHIJK12 34567890 <- Kabat
    QKFKDKATLTVDKSSTAYMRLSSLTSEDSAVYYCARGGYDFDVGTLYWFF  DVWGAGTTVTVS  Z270VH       2
    QKLQGRVTMTTDISTSTAYMELRSLRSDDTAVYYCARGGYDFDVGTLYWFF  DVWGQGTTVTVS  humZ270VH1   5
    PSFQGHVTISADKSISTAYLQWSSLKASDTAMYYCARGGYDFDVGTLYWFF  DVWGQGTTVTVS  humZ270VH5  26
    PSFQGQVTISADKSISTAYLQWSSLKASDTAMYYCARGGYDFDVGTLYWFF  DVWGQGTTVTVS  humZ270VH6  27
    EKFQGRVTIIADISTDTAYMELSSLRSEDTAVYYCATGGYDFDVGTLYWFF  DVWGQGTTVTVS  humZ270VH7  28
    QKFQGRVTMTRDTSTSTVYMELSSLRSEDTAVYYCARGGYDFDVGTLYWFF  DVWGQGTTVTVS  humZ270VH8  29
```

Fig. 12

```
Light Chain                                                              SEQ ID NO:
            1          2           3            4          5         6
    1234567890123456789012 4567ABCDEF890123456 789012345 678 0123456 789
    DIQMTQSPASLSASVGETVTITCRASE               NIYSYLAWYQQKGKSPQFLVYNAKTLAEGVPS    Z270VL
    ....................A.AA......A.AA................A.AA..A 7       8           9         10
    1234567 8 901 2345678901234567 8901234 5AB67 890123456789 <- The Kabat Scheme
    RFSGSGSGTQFSLKINSLQPEDFGSYYCQHHYGTP     RTFGGGTKLEIK       Z270VL                1
    ............................A.A Heavy Chain
            1          2           3            4          5         6
    1234 5678901234567890123 456 78 12345AB 7890123456 78 012ABC34567890
    QVQLQQPGAELVRPGASVKLSCKASGYTFTSYWMN       WVKQRPFQGLQWIGRIDP  YDSETHYS    Z270VH
    ....................A.A..A.AA...A..................A...AAAA 7       8          9         10          11
    12345678 9 1234 56 89012ABC345678901 23 567890ABCDEFGHIJK12 4567890 <- Kabat
    QKFKDKATLTVDKSSSTAYMRLSSLTSEDSAVYYCARGGYDFDVGTLYWFF        DVWGAGTTVTVS  Z270VH   2
    ...........................A...AAAA.AA.A.....A
```

Fig. 14

SEQUENCE LISTING

```
<160> NUMBER OF SEQ ID NOS: 29

<210> SEQ ID NO 1
<211> LENGTH: 107
<212> TYPE: PRT
<213> ORGANISM: Mus musculus

<400> SEQUENCE: 1

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Phe Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Arg
                85                  90                  95

Thr Phe Gly Gly Gly Thr Lys Leu Glu Ile Lys
            100                 105

<210> SEQ ID NO 2
<211> LENGTH: 124
<212> TYPE: PRT
<213> ORGANISM: Mus musculus

<400> SEQUENCE: 2

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30
```

Trp Met Asn Trp Val Lys Gln Arg Pro Glu Gln Gly Leu Gln Trp Ile
            35                  40                  45

Gly Arg Ile Asp Pro Tyr Asp Ser Glu Thr His Tyr Ser Gln Lys Phe
 50                  55                  60

Lys Asp Lys Ala Ile Leu Thr Val Asp Lys Ser Ser Thr Ala Tyr
65                  70                  75                  80

Met Arg Leu Ser Ser Leu Thr Ser Glu Asp Ser Ala Val Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Ala Gly Thr Thr Val Thr Val Ser
        115                 120

<210> SEQ ID NO 3
<211> LENGTH: 107
<212> TYPE: PRT
<213> ORGANISM: Mus musculus

<400> SEQUENCE: 3

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 4
<211> LENGTH: 107
<212> TYPE: PRT
<213> ORGANISM: Artificial
<220> FEATURE:
<223> OTHER INFORMATION: Humanized sequence

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Arg
                85                  90                  95

Thr Phe Gly Gly Gly Thr Lys Val Glu Ile Lys
            100                 105

```
<210> SEQ ID NO 5
<211> LENGTH: 124
<212> TYPE: PRT
<213> ORGANISM: Artificial
<220> FEATURE:
<223> OTHER INFORMATION: Humanized sequence

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met Asn Trp Val Arg Gln Ala Pro Gly Gln Gly Leu Glu Trp Met
            35                  40                  45

Gly Arg Ile Asp Pro Tyr Asp Ser Glu Thr His Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser
        115                 120

<210> SEQ ID NO 6
<211> LENGTH: 107
<212> TYPE: PRT
<213> ORGANISM: Artificial
<220> FEATURE:
<223> OTHER INFORMATION: Humanized sequence
<220> FEATURE:
<221> NAME/KEY: UNSURE
<222> LOCATION: (46)..(46)
<223> OTHER INFORMATION: Xaa is L or F
<220> FEATURE:
<221> NAME/KEY: UNSURE
<222> LOCATION: (48)..(48)
<223> OTHER INFORMATION: Xaa is I or V

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
                20                  25                  30

Leu Ala Trp Tyr Gln Gln Lys Pro Gly Lys Ala Pro Lys Xaa Leu Xaa
            35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Arg
                85                  90                  95

Thr Phe Gly Gly Gly Thr Lys Val Glu Ile Lys
            100                 105

<210> SEQ ID NO 7
<211> LENGTH: 124
<212> TYPE: PRT
<213> ORGANISM: Artificial
<220> FEATURE:
<223> OTHER INFORMATION: Humanized sequence
```

-continued

```
<220> FEATURE:
<221> NAME/KEY: UNSURE
<222> LOCATION: (5)..(5)
<223> OTHER INFORMATION: Xaa is V or Q
<220> FEATURE:
<221> NAME/KEY: UNSURE
<222> LOCATION: (70)..(70)
<223> OTHER INFORMATION: Kabat position 69; Xaa is M or L
<220> FEATURE:
<221> NAME/KEY: UNSURE
<222> LOCATION: (72)..(72)
<223> OTHER INFORMATION: Kabat position 71; Xaa is T or V
<220> FEATURE:
<221> NAME/KEY: UNSURE
<222> LOCATION: (74)..(74)
<223> OTHER INFORMATION: Kabat position 73; Xaa is T or K
<220> FEATURE:
<221> NAME/KEY: UNSURE
<222> LOCATION: (76)..(76)
<223> OTHER INFORMATION: Kabat position 75; Xaa is T or S

<400> SEQUENCE: 7

Gln Val Gln Leu Xaa Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met Asn Trp Val Arg Gln Ala Pro Gly Gln Gly Leu Glu Trp Met
            35                  40                  45

Gly Arg Ile Asp Pro Tyr Asp Ser Glu Thr His Tyr Ala Gln Lys Leu
    50                  55                  60

Gln Gly Arg Val Thr Xaa Thr Xaa Asp Xaa Ser Xaa Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser
        115                 120

<210> SEQ ID NO 8
<211> LENGTH: 124
<212> TYPE: PRT
<213> ORGANISM: Artificial
<220> FEATURE:
<223> OTHER INFORMATION: Humanized sequence
<220> FEATURE:
<221> NAME/KEY: UNSURE
<222> LOCATION: (5)..(5)
<223> OTHER INFORMATION: Xaa is V or Q
<220> FEATURE:
<221> NAME/KEY: UNSURE
<222> LOCATION: (61)..(61)
<223> OTHER INFORMATION: Kabat position 60; Xaa is S or A
<220> FEATURE:
<221> NAME/KEY: UNSURE
<222> LOCATION: (64)..(64)
<223> OTHER INFORMATION: Kabat position 63; Xaa is L or F
<220> FEATURE:
<221> NAME/KEY: UNSURE
<222> LOCATION: (65)..(65)
<223> OTHER INFORMATION: Kabat position 64; Xaa is Q or K
<220> FEATURE:
<221> NAME/KEY: UNSURE
<222> LOCATION: (66)..(66)
<223> OTHER INFORMATION: Kabat position 65; Xaa is G or D
<220> FEATURE:
<221> NAME/KEY: UNSURE
<222> LOCATION: (67)..(67)
<223> OTHER INFORMATION: Kabat position 66; Xaa is R or K
<220> FEATURE:
```

```
<221> NAME/KEY: UNSURE
<222> LOCATION: (68)..(68)
<223> OTHER INFORMATION: Kabat position 67; Xaa is V or A
<220> FEATURE:
<221> NAME/KEY: UNSURE
<222> LOCATION: (70)..(70)
<223> OTHER INFORMATION: Kabat position 69; Xaa is M or L
<220> FEATURE:
<221> NAME/KEY: UNSURE
<222> LOCATION: (72)..(72)
<223> OTHER INFORMATION: Kabat position 71; Xaa is T or V
<220> FEATURE:
<221> NAME/KEY: UNSURE
<222> LOCATION: (74)..(74)
<223> OTHER INFORMATION: Kabat position 73; Xaa is T or K
<220> FEATURE:
<221> NAME/KEY: UNSURE
<222> LOCATION: (76)..(76)
<223> OTHER INFORMATION: Kabat position 75; Xaa is T or S

<400> SEQUENCE: 8

Gln Val Gln Leu Xaa Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Arg Ile Asp Pro Tyr Asp Ser Glu Thr His Tyr Xaa Gln Lys Xaa
    50                  55                  60

Xaa Xaa Xaa Xaa Thr Xaa Thr Xaa Asp Xaa Ser Xaa Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser
        115                 120

<210> SEQ ID NO 9
<211> LENGTH: 107
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 10
<211> LENGTH: 117
<212> TYPE: PRT
```

<213> ORGANISM: Homo sapiens

<400> SEQUENCE: 10

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Asn Gly Asn Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Tyr Tyr Tyr Tyr Tyr Gly Met Asp Val Trp Gly Gln Gly Thr
            100                 105                 110
Thr Val Thr Val Ser
            115
```

<210> SEQ ID NO 11
<211> LENGTH: 233
<212> TYPE: PRT
<213> ORGANISM: Homo sapiens

<400> SEQUENCE: 11

```
Met Asp Asn Gln Gly Val Ile Tyr Ser Asp Leu Asn Leu Pro Pro Asn
1               5                   10                  15
Pro Lys Arg Gln Gln Arg Lys Pro Lys Gly Asn Lys Ser Ser Ile Leu
            20                  25                  30
Ala Thr Glu Gln Glu Ile Thr Tyr Ala Glu Leu Asn Leu Gln Lys Ala
        35                  40                  45
Ser Gln Asp Phe Gln Gly Asn Asp Lys Thr Tyr His Cys Lys Asp Leu
    50                  55                  60
Pro Ser Ala Pro Glu Lys Leu Ile Val Gly Ile Leu Gly Ile Ile Cys
65                  70                  75                  80
Leu Ile Leu Met Ala Ser Val Val Thr Ile Val Val Ile Pro Ser Thr
                85                  90                  95
Leu Ile Gln Arg His Asn Asn Ser Ser Leu Asn Thr Arg Thr Gln Lys
            100                 105                 110
Ala Arg His Cys Gly His Cys Pro Glu Glu Trp Ile Thr Tyr Ser Asn
        115                 120                 125
Ser Cys Tyr Tyr Ile Gly Lys Glu Arg Arg Thr Trp Glu Glu Ser Leu
    130                 135                 140
Leu Ala Cys Thr Ser Lys Asn Ser Ser Leu Leu Ser Ile Asp Asn Glu
145                 150                 155                 160
Glu Glu Met Lys Phe Leu Ser Ile Ile Ser Pro Ser Ser Trp Ile Gly
                165                 170                 175
Val Phe Arg Asn Ser Ser His His Pro Trp Val Thr Met Asn Gly Leu
            180                 185                 190
Ala Phe Lys His Glu Ile Lys Asp Ser Asp Asn Ala Glu Leu Asn Cys
        195                 200                 205
Ala Val Leu Gln Val Asn Arg Leu Lys Ser Ala Gln Cys Gly Ser Ser
    210                 215                 220
Ile Ile Tyr His Cys Lys His Lys Leu
```

```
225              230
```

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
gccagtggat agacagatgg                                                     20

<210> SEQ ID NO 13
<211> LENGTH: 21
<212> TYPE: DNA
<213> ORGANISM: Artificial
<220> FEATURE:
<223> OTHER INFORMATION: Primer

<400> SEQUENCE: 13
gatggataca gttggtgcag c                                                   21

<210> SEQ ID NO 14
<211> LENGTH: 381
<212> TYPE: DNA
<213> ORGANISM: Mus musculus

<400> SEQUENCE: 14
atgagtgtgc ccactcaggt cctggggttg ctgctgctgt ggcttacagg tgccagatgt         60
gacatccaga tgactcagtc tccagcctcc ctatctgcat ctgtgggaga aactgtcacc        120
atcacatgtc gagcaagtga aaatatttac agttatttag catggtatca gcagaaacag        180
ggaaaatctc ctcagttctt ggtctataat gcaaaaacct tagcagaagg tgtgccatca        240
aggttcagtg gcagtggatc aggcacacag ttttctctga agatcaacag cctgcagcct        300
gaagattttg ggagttatta ctgtcaacat cactatggta ctcctcggac gttcggtgga        360
ggcaccaagc tggaaatcaa a                                                  381

<210> SEQ ID NO 15
<211> LENGTH: 127
<212> TYPE: PRT
<213> ORGANISM: Mus musculus

<400> SEQUENCE: 15

Met Ser Val Pro Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
                20                  25                  30

Ala Ser Val Gly Glu Thr Val Thr Ile Thr Cys Arg Ala Ser Glu Asn
            35                  40                  45

Ile Tyr Ser Tyr Leu Ala Trp Tyr Gln Gln Lys Gln Gly Lys Ser Pro
        50                  55                  60

Gln Phe Leu Val Tyr Asn Ala Lys Thr Leu Ala Glu Gly Val Pro Ser
65                  70                  75                  80

Arg Phe Ser Gly Ser Gly Ser Gly Thr Gln Phe Ser Leu Lys Ile Asn
                85                  90                  95

Ser Leu Gln Pro Glu Asp Phe Gly Ser Tyr Tyr Cys Gln His His Tyr
            100                 105                 110

Gly Thr Pro Arg Thr Phe Gly Gly Gly Thr Lys Leu Glu Ile Lys
        115                 120                 125

<210> SEQ ID NO 16
<211> LENGTH: 432
<212> TYPE: DNA
<213> ORGANISM: Mus musculus

<400> SEQUENCE: 16

```
atgggatgga gctatatcat cctcttcttg ttagcaacag ctacatgtgt ccactcccag      60
gtccaactgc agcagcctgg ggctgagctg gtgaggcctg ggcttcagt gaagctgtcc      120
tgcaaggctt ctggctacac gttcaccagc tactggatga actgggttaa gcagaggcct    180
gagcaaggcc ttcagtggat tggaaggatt gatccttacg atagtgaaac tcactacagt    240
caaaagttca aggacaaggc cattgac gtagacaaat cctccagcac agcctacatg       300
cgactcagca gcctgacatc tgaggactct gcggtctatt actgtgcaag gggggctat     360
gatttcgacg taggaactct ctactggttc ttcgatgtct ggggcgcagg gaccacggtc    420
accgtctcct ca                                                        432
```

<210> SEQ ID NO 17
<211> LENGTH: 144
<212> TYPE: PRT
<213> ORGANISM: Mus musculus

<400> SEQUENCE: 17

```
Met Gly Trp Ser Tyr Ile Ile Leu Phe Leu Leu Ala Thr Ala Thr Cys
1               5                   10                  15
Val His Ser Gln Val Gln Leu Gln Gln Pro Gly Ala Glu Leu Val Arg
            20                  25                  30
Pro Gly Ala Ser Val Lys Leu Ser Cys Lys Ala Ser Gly Tyr Thr Phe
        35                  40                  45
Thr Ser Tyr Trp Met Asn Trp Val Lys Gln Arg Pro Glu Gln Gly Leu
    50                  55                  60
Gln Trp Ile Gly Arg Ile Asp Pro Tyr Asp Ser Glu Thr His Tyr Ser
65                  70                  75                  80
Gln Lys Phe Lys Asp Lys Ala Ile Leu Thr Val Asp Lys Ser Ser Ser
                85                  90                  95
Thr Ala Tyr Met Arg Leu Ser Ser Leu Thr Ser Glu Asp Ser Ala Val
            100                 105                 110
Tyr Tyr Cys Ala Arg Gly Gly Tyr Asp Phe Asp Val Gly Thr Leu Tyr
        115                 120                 125
Trp Phe Phe Asp Val Trp Gly Ala Gly Thr Thr Val Thr Val Ser Ser
    130                 135                 140
```

<210> SEQ ID NO 18
<211> LENGTH: 723
<212> TYPE: DNA
<213> ORGANISM: Artificial
<220> FEATURE:
<223> OTHER INFORMATION: Chimeric sequence

<400> SEQUENCE: 18

```
gaattcgcca ccatgagtgt gcccactcag gtcctggggt tgctgctgct gtggcttaca     60
ggtgccagat gtgacatcca gatgactcag tctccagcct ccctatctgc atctgtggga    120
gaaactgtca ccatcacatg tcgagcaagt gagaatattt acagttattt agcatggtat    180
cagcagaaac aggaaaatc tcctcagttc ttggtctata atgcaaaaac cttagcagaa    240
ggtgtgccat caaggttcag tggcagtgga tcaggcacac agttttctct gaagatcaac    300
```

```
agcctgcagc ctgaagattt tgggagttat tactgtcaac atcactatgg tactcctcgg      360
acgttcggtg gaggcaccaa gctggaaatc aaacgggctg atgctgcacc aactgtatcc      420
atcttcccac catccagtga gcagttaaca tctggaggtg cctcagtcgt gtgcttcttg      480
aacaacttct accccaaaga catcaatgtc aagtggaaga ttgatggcag tgaacgacaa      540
aatggcgtcc tgaacagttg gactgatcag acagcaaag acagcaccta cagcatgagc       600
agcaccctca cgttgaccaa ggacgagtat aacgacata acagctatac ctgtgaggcc       660
actcacaaga catcaacttc acccattgtc aagagcttca caggaatga gtgttaggct       720 agc                                                                   723

<210> SEQ ID NO 19
<211> LENGTH: 1419
<212> TYPE: DNA
<213> ORGANISM: Artificial
<220> FEATURE:
<223> OTHER INFORMATION: Chimeric sequence

<400> SEQUENCE: 19
gaattcgcca ccatgggatg gagctatatc atcctcttct tgttagcaac agctacatgt       60
gtccactccc aggtccaact gcagcagcct ggggctgagc tggtgaggcc tggggcttca      120
gtgaagctgt cctgcaaggc ttctggctac acgttcacca gctactggat gaactgggtt      180
aagcagaggc ctgagcaagg ccttcagtgg attggaagga ttgatcctta cgatagtgaa      240
actcactaca gtcaaaagtt caaggacaag gccatattga ctgtagacaa atcctccagc      300
acagcctaca tgcgactcag cagcctgaca tctgaggact ctgcggtcta ttactgtgca      360 agaggggct atgatttcga cgtaggaact ctctactggt tcttcgatgt ctggggcgca       420
gggaccacgg tcaccgtctc ctcagccaaa acgacacccc catctgtcta tccgctagcc      480
cctggatctg ctgcccaaac taactccatg gtgaccctgg gatgcctggt caagggctat      540
ttccctgagc cagtgacagt gacctggaac tctggatccc tgtccagcgg tgtgcacacc      600 ttccagctg tcctgcagtc tgacctctac actctgagca gctcagtgac tgtcccctcc       660
agcacctggc ccagcgagac cgtcacctgc aacgttgccc accggccag cagcaccaag       720 gtggacaaga aaattgtgcc cagggattgt ggttgtaagc cttgcatatg tacagtccca      780
gaagtatcat ctgtcttcat cttccccccca aagcccaagg atgtgctcac cattactctg     840
actcctaagg tcacgtgtgt tgtggtagac atcagcaagg atgatcccga ggtccagttc      900
agctggtttg tagatgatgt ggaggtgcac acagctcaga cgcaaccccg ggaggagcag      960
ttcaacagca ctttccgctc agtcagtgaa cttcccatca tgcaccagga ctggctcaat     1020
ggcaaggagt tcaaatgcag ggtcaacagt gcagctttcc ctgcccccat cgagaaaacc     1080
atctccaaaa ccaaaggcag accgaaggct ccacaggtgt acaccattcc acctcccaag     1140
gagcagatgg ccaaggataa agtcagtctg acctgcatga taacagactt cttccctgaa     1200
gacattactg tggagtggca gtggaatggg cagccagcgg agaactacaa gaacactcag     1260
cccatcatgg acacagatgg ctcttacttc gtctacagca agctcaatgt gcagaagagc     1320
aactgggagg caggaaatac tttcacctgc tctgtgttac atgagggcct gcacaaccac     1380
catactgaga agagcctctc ccactctcct ggtaaatga                            1419

<210> SEQ ID NO 20
<211> LENGTH: 723
<212> TYPE: DNA
```

```
<213> ORGANISM: Artificial
<220> FEATURE:
<223> OTHER INFORMATION: Chimeric sequence

<400> SEQUENCE: 20
gaattcgcca ccatgagtgt gcccactcag gtcctggggt tgctgctgct gtggcttaca      60
ggtgccagat gtgacatcca gatgactcag tctccagcct ccctatctgc atctgtggga     120
gaaactgtca ccatcacatg tcgagcaagt gagaatattt acagttattt agcatggtat     180
cagcagaaac agggaaaatc tcctcagttc ttggtctata atgcaaaaac cttagcagaa     240
ggtgtgccat caaggttcag tggcagtgga tcaggcacac agttttctct gaagatcaac     300
agcctgcagc ctgaagattt tgggagttat tactgtcaac atcactatgg tactcctcgg     360
acgttcggtg gaggcaccaa gctggaaatc aaacggactg tggcggcgcc atctgtcttc     420
atcttcccgc catctgatga gcagttgaaa tctggtaccg ctagcgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc     660
acccatcagg gcctgagctc gcccgtcaca aagagcttca caggggaga gtgttaggga     720
tcc                                                                  723

<210> SEQ ID NO 21
<211> LENGTH: 1434
<212> TYPE: DNA
<213> ORGANISM: Artificial
<220> FEATURE:
<223> OTHER INFORMATION: Chimeric sequence

<400> SEQUENCE: 21
gaattcgcca ccatgggatg gagctatatc atcctcttct tgttagcaac agctacatgt      60
gtccactccc aggtccaact gcagcagcct ggggctgagc tggtgaggcc tggggcttca     120
gtgaagctgt cctgcaaggc ttctggctac acgttcacca gctactggat gaactgggtt     180
aagcagaggc ctgagcaagg ccttcagtgg attggaagga ttgatcctta cgatagtgaa     240
actcactaca gtcaaaagtt caaggacaag gccatattga ctgtagacaa atcctccagc     300
acagcctaca tgcgactcag cagcctgaca tctgaggact ctgcggtcta ttactgtgca     360
agagggggct atgatttcga cgtaggaact ctctactggt tcttcgatgt ctggggcgca     420
gggaccacgg tcaccgtctc ctcagctagc accaagggcc catccgtctt ccccctggcg     480
ccctgctcca ggagcacctc cgagagcaca gccgccctgg gctgcctggt caaggactac     540
ttccccgaac cggtgacggt gtcgtggaac tcaggcgccc tgaccagcgg cgtgcacacc     600
ttcccggctg tcctacagtc ctcaggactc tactccctca gcagcgtggt gaccgtgccc     660
tccagcagct tgggcacgaa gacctacacc tgcaacgtag atcacaagcc cagcaacacc     720
aaggtggaca agagagttga gtccaaatat ggtccccat gcccaccatg cccagcacct     780
gagttcctgg gggaccatc agtcttcctg ttccccccaa acccaagga cactctcatg     840
atctcccgga cccctgaggt cacgtgcgtg gtggtggacg tgagccagga agaccccgag     900
gtccagttca actggtacgt ggatggcgtg gaggtgcata atgccaagac aaagccgcgg     960
gaggagcagt tcaacagcac gtaccgtgtg gtcagcgtcc tcaccgtcct gcaccaggac    1020
tggctgaacg gcaaggagta caagtgcaag gtctccaaca aaggcctccc gtcctccatc    1080
gagaaaacca tctccaaagc caaagggcag ccccgagagc cacaggtgta cacctgcccc    1140
```

| | |
|---|---|
| ccatcccagg aggagatgac caagaaccag gtcagcctga cctgcctggt caaaggcttc | 1200 |
| taccccagcg acatcgccgt ggagtgggag agcaatgggc agccggagaa caactacaag | 1260 |
| accacgcctc ccgtgctgga ctccgacggc tccttcttcc tctacagcag gctaaccgtg | 1320 |
| gacaagagca ggtggcagga ggggaatgtc ttctcatgct ccgtgatgca tgaggctctg | 1380 |
| cacaaccact acacacagaa gagcctctcc ctgtctctgg gtaaatgagg atcc | 1434 |

<210> SEQ ID NO 22
<211> LENGTH: 723
<212> TYPE: DNA
<213> ORGANISM: Artificial
<220> FEATURE:
<223> OTHER INFORMATION: Humanized sequence

<400> SEQUENCE: 22

| | |
|---|---|
| gaattcgcca ccatggacat gagggtcccc gctcagctcc tggggctcct gctactctgg | 60 |
| ctccgaggtg ccagatgtga catccagatg acccagtctc catcctccct gtctgcatct | 120 |
| gtaggagaca gagtcaccat cacttgccga gcaagtgaga atatttacag ttatttagca | 180 |
| tggtatcagc agaaaccagg gaaagcccct aagctcctga tctataatgc aaaaaccttt a | 240 |
| gcagaagggg tcccatcaag gttcagtggc agtggatctg ggacagattt cactctcacc | 300 |
| atcagcagtc tgcaacctga agattttgca acttactact gtcaacatca ctatggtact | 360 |
| cctcggacgt tcggcggagg gaccaaggtg gagatcaaac ggactgtggc tgcgccatct | 420 |
| gtcttcatct tcccgccatc tgatgagcag ttgaaatctg gtaccgctag cgttgtgtgc | 480 |
| ctgctgaata acttctatcc cagagaggcc aaagtacagt ggaaggtgga taacgccctc | 540 |
| caatcgggta actcccagga gagtgtcaca gagcaggaca gcaaggacag cacctacagc | 600 |
| ctcagcagca ccctgacgct gagcaaagca gactacgaga acacaaagt ctacgcctgc | 660 |
| gaagtcaccc atcagggcct gagctcgccc gtcacaaaga gcttcaacag gggagagtgt | 720 |
| tag | 723 |

<210> SEQ ID NO 23
<211> LENGTH: 1428
<212> TYPE: DNA
<213> ORGANISM: Artificial
<220> FEATURE:
<223> OTHER INFORMATION: Humanized sequence

<400> SEQUENCE: 23

| | |
|---|---|
| gaattcgcca ccatggactg gacctggagc atccttttct tggtggcagc agcaacaggt | 60 |
| gcccactccc aggttcagct ggtgcagtct ggagctgagg tgaagaagcc tggggcctca | 120 |
| gtgaaggtct cctgcaaggc ttctggttac acctttacca gctactggat gaactgggtg | 180 |
| cgacaggccc ctggacaagg gcttgagtgg atgggaagga ttgatcctta cgatagtgaa | 240 |
| actcactatg cacagaagct ccagggcaga gtcaccatga ccacagacac atccacgagc | 300 |
| acagcctaca tggagctgag gagcctgaga tctgacgaca cggccgtgta ttactgtgcg | 360 |
| agaggggct atgatttcga cgtaggaact ctctactggt tcttcgatgt ctggggccaa | 420 |
| gggacaacgg tcaccgtctc ttcagctagc accaagggcc catccgtctt ccccctggcg | 480 |
| ccctgctcca ggagcaccct cgagagcaca gccgccctgg gctgcctggt caaggactac | 540 |
| ttccccgaac cggtgacggt gtcgtggaac tcaggcgccc tgaccagcgg cgtgcacacc | 600 |
| ttcccggctg tcctacagtc ctcaggactc tactccctca gcagcgtggt gaccgtgccc | 660 |

-continued

```
tccagcagct tgggcacgaa gacctacacc tgcaacgtag atcacaagcc cagcaacacc    720
aaggtggaca agagagttga gtccaaatat ggtcccccat gcccaccatg cccagcacct    780
gagttcctgg ggggaccatc agtcttcctg ttccccccaa aacccaagga cactctcatg    840
atctcccgga cccctgaggt cacgtgcgtg gtggtggacg tgagccagga agaccccgag    900
gtccagttca actggtacgt ggatggcgtg gaggtgcata atgccaagac aaagccgcgg    960
gaggagcagt tcaacagcac gtaccgtgtg gtcagcgtcc tcaccgtcct gcaccaggac   1020
tggctgaacg gcaaggagta caagtgcaag gtctccaaca aaggcctccc gtcctccatc   1080
gagaaaacca tctccaaagc caaagggcag ccccgagagc cacaggtgta caccctgccc   1140
ccatcccagg aggagatgac caagaaccag gtcagcctga cctgcctggt caaaggcttc   1200
taccccagcg acatcgccgt ggagtgggag agcaatgggc agccggagaa caactacaag   1260
accacgcctc ccgtgctgga ctccgacggc tccttcttcc tctacagcag gctaaccgtg   1320
gacaagagca ggtggcagga ggggaatgtc ttctcatgct ccgtgatgca tgaggctctg   1380
cacaaccact acacacagaa gagcctctcc ctgtctctgg gtaaatga               1428
```

<210> SEQ ID NO 24
<211> LENGTH: 124
<212> TYPE: PRT
<213> ORGANISM: Artificial
<220> FEATURE:
<223> OTHER INFORMATION: Humanized sequence

<400> SEQUENCE: 24

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Arg Ile Asp Pro Tyr Asp Ser Glu Thr His Tyr Ser Gln Lys Phe
    50                  55                  60

Lys Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser
        115                 120
```

<210> SEQ ID NO 25
<211> LENGTH: 124
<212> TYPE: PRT
<213> ORGANISM: Artificial
<220> FEATURE:
<223> OTHER INFORMATION: Humanized sequence

<400> SEQUENCE: 25

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Lys Gln Ala Pro Gly Gln Gly Leu Gln Trp Ile
        35                  40                  45
```

```
Gly Arg Ile Asp Pro Tyr Asp Ser Glu Thr His Tyr Ser Gln Lys Phe
        50                  55                  60

Lys Asp Lys Ala Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser
            115                 120
```

<210> SEQ ID NO 26
<211> LENGTH: 124
<212> TYPE: PRT
<213> ORGANISM: Artificial
<220> FEATURE:
<223> OTHER INFORMATION: Humanized sequence

<400> SEQUENCE: 26

```
Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Ser Phe Thr Ser Tyr
                20                  25                  30

Trp Met Asn Trp Val Arg Gln Met Pro Gly Lys Gly Leu Glu Trp Met
            35                  40                  45

Gly Arg Ile Asp Pro Tyr Asp Ser Glu Thr His Tyr Ser Pro Ser Phe
        50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser
            115                 120
```

<210> SEQ ID NO 27
<211> LENGTH: 124
<212> TYPE: PRT
<213> ORGANISM: Artificial
<220> FEATURE:
<223> OTHER INFORMATION: Humanized sequence

<400> SEQUENCE: 27

```
Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                20                  25                  30

Trp Met Asn Trp Val Arg Gln Met Pro Gly Lys Gly Leu Glu Trp Met
            35                  40                  45

Gly Arg Ile Asp Pro Tyr Asp Ser Glu Thr His Tyr Ser Pro Ser Phe
        50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Gly Tyr Asp Phe Asp Val Gly Thr Leu Tyr Trp Phe Phe
            100                 105                 110
```

```
Asp Val Trp Gly Gln Gly Thr Thr Val Thr Val Ser
            115                 120

<210> SEQ ID NO 28
<211> LENGTH: 124
<212> TYPE: PRT
<213> ORGANISM: Artificial
<220> FEATURE:
<223> OTHER INFORMATION: Humanized sequence

<400> SEQUENCE: 28

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Asn Trp Val Gln Gln Ala Pro Gly Lys Gly Leu Glu Trp Met
            35                  40                  45

Gly Arg Ile Asp Pro Tyr Asp Ser Glu Thr His Tyr Ala Glu Lys Phe
        50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Tyr Asp Phe Asp Val Gly Leu Tyr Trp Phe Phe
            100                 105                 110

Asp Val Trp Gly Gln Gly Thr Thr Val Thr Val Ser
            115                 120

<210> SEQ ID NO 29
<211> LENGTH: 124
<212> TYPE: PRT
<213> ORGANISM: Artificial
<220> FEATURE:
<223> OTHER INFORMATION: Humanized sequence

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
            35                  40                  45

Gly Arg Ile Asp Pro Tyr Asp Ser Glu Thr His Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asp Phe Asp Val Gly Leu Tyr Trp Phe Phe
            100                 105                 110

Asp Val Trp Gly Gln Gly Thr Thr Val Thr Val Ser
            115                 120
```

ANTI-NKG2A ANTIBODIES AND USES THEREOF

CROSS-REFERENCE TO RELATED APPLICATIONS

This application is a divisional of U.S. application Ser. No. 13/477,888, filed May 22, 2012, now U.S. Pat. No. 8,901,283, which is a continuation of U.S. application Ser. No. 12/305,683, filed May 26, 2009 (now U.S. Pat. No. 8,206,709), which is a 35 U.S.C. §371 national stage application of International Patent Application PCT/EP2007/056485 (published as WO 2008/009545), filed Jun. 28, 2007, which claimed priority of European Patent Application 06116429.9, filed Jun. 30, 2006; this application further claims priority under 35 U.S.C. §119 of U.S. Provisional Application 60/818,550, filed Jul. 5, 2006; the contents of all above-named applications are incorporated herein by reference.

FIELD OF THE INVENTION

The present invention relates to anti-NKG2A antibodies, in particular humanized versions of murine anti-NKG2A antibody Z270, as well as methods of producing and using such antibodies.

BACKGROUND OF THE INVENTION

CD94/NKG2A is a cytotoxicity inhibitory receptor found on subsets of NK, NKT and T cells, which restricts their killing of cells expressing the CD94/NKG2A-ligand HLA-E (see, e.g., WO99/28748). Antibodies that inhibit CD94/NKG2A may increase the cytolytic activity of tumor-specific lymphocytes against tumor cells. Therefore, therapeutic antibodies that inhibit CD94/NKG2A in cancer patients without killing CD94/NKG2A-expressing cells may be able to control tumor-growth. In addition, certain lymphomas such as, e.g., NK-lymphomas, are characterized by CD94/NKG2A expression. In such patients, therapeutic antibodies that target and kill CD94/NKG2A-expressing cells may be able to eradicate tumor cells. Anti-NKG2A antibodies have also been suggested for use in treating autoimmune or inflammatory diseases (see, e.g., US20030095965A1, WO2006070286).

Various antibodies against CD94/NKG2A have been described in the art. For example, Sivori et al. (Eur J Immunol 1996; 26:2487-92) refers to the murine anti-NKG2A antibody Z270; Carretero et al. (Eur J Immunol 1997; 27:563-7) describes murine anti-NKG2A antibody Z199 (now commercially available via Beckman Coulter, Inc., Product No. IM2750, USA); Vance et al. (J Exp Med 1999; 190: 1801-12) refers to murine anti-NKG2-antibody 20D5 (now commercially available via BD Biosciences Pharmingen, Catalog No. 550518, USA); and U.S. patent application publication 20030095965 describes murine antibody 3S9, which purportedly binds to NKG2A, NKG2C and NKG2E.

Currently available anti-CD94/NKG2A antibodies are of non-human origin, which makes them unsuitable for most therapeutic applications in humans due to their immunogenicity. While simple humanization approaches such as, e.g., CDR-grafting, are available, individualized humanization approaches are typically needed to obtain an optimal humanized variant, minimizing immunogenicity while sufficiently retaining or improving functional properties. Accordingly, there is a need for anti-CD94/NKG2A antibodies that are suitable for treatment of human patients.

SUMMARY OF THE INVENTION

The present invention provides anti-NKG2A antibodies, as well as compositions comprising such antibodies, and methods of producing and using such antibodies. In one embodiment, the antibody is a humanized version of murine anti-NKG2A antibody Z270, herein denoted a "humZ270". In another embodiment, the antibody is a humanized version of an anti-NKG2A antibody having substantially identical variable heavy-chain (VH) and/or variable light-chain (VL) domains to those of Z270.

Exemplary complementarity-determining region (CDR) residues and/or sites for amino acid substitutions in framework region (FR) and/or of such antibodies to produce antibodies having improved properties such as, e.g., lower immunogenicity, improved antigen-binding or other functional properties, and/or improved physicochemical properties such as, e.g., better stability, are provided. In one aspect, the invention provides humanized antibodies in which at least a portion of a Kabat CDR is identical to the corresponding portion in the human acceptor sequence. In one embodiment, the human acceptor framework sequence does not comprise any amino acid substitutions or back-mutations. In another embodiment, the human framework sequence comprises at least one amino acid substitution. Kabat positions for such exemplary amino acid substitutions include 5, 66, 67, 69, 71, 73, and 75 in the framework region of the VH domain, 46 and 48 in the framework region of the VL domain, and 60, 63, 64, and 65 in CDR-H2.

In other aspects, the invention provides for pharmaceutical compositions comprising such antibodies and a carrier, and for immunoconjugates comprising such antibodies conjugated to a cytotoxic or detectable agent.

In other aspects, the invention provides for nucleic acids and vectors encoding such antibodies, and host cells containing such nucleic acids and/or vectors. Also provided for are recombinant methods of producing anti-NKG2A antibodies by culturing such host cells so that the nucleic acids are produced.

In other aspects, the invention provides for articles of manufacture comprising a container comprising such anti-NKG2A antibodies and instructions directing a user to treat a disorder such as cancer or a viral disease in a patient. Optionally, the article may comprise another container containing another agent, wherein the instructions direct the user to treat the disorder with the antibody in combination with the agent.

The invention also provides for methods of using such anti-NKG2A antibodies in the treatment of disorders such as cancer, a viral disease, an inflammatory disorder or an autoimmune disorder in a patient, optionally in conjunction with another anti-cancer, anti-viral disease agent, or anti-inflammatory agent.

DESCRIPTION OF THE DRAWINGS

FIG. 1 shows an alignment of Z270VL and Z270VH with selected germline V- and J-segments and exemplary humZ270VL1 (SEQ ID NO:4) and humZ270VH1 (SEQ ID NO:5) sequences, with amino acid residue numbering according to the Kabat scheme (Kabat et al, 1991, Sequences of Proteins of Immunological Interest, 5th Ed. Public Health Service, National Institutes of Health, Bethesda, Md.) Mask residues are shaded in the Kabat scheme; CDR residues are shown in bold in the Kabat scheme; mouse/germline differences are shaded in the VKI_02/JK4 (SEQ ID NO:9) and VH1_18/JH6 (SEQ ID NO:10) sequences; and potential back-mutation residues are shaded in the humZ270VH/VL sequences. The identified potential back-mutations in the VL were L46F and I48V. The identified potential back-mutations in the heavy chain were V5Q, M69L, T71V, T73K, and T75S. Also shown are the resulting humZ270VL consensus ("humZ270VL1 cons;" SEQ ID NO:6) and humZ270VH1 ("humZ270VH1 cons;" SEQ ID NO:7) consensus sequences. In humZ270VL1 cons, the amino acid at position 46 is L or F, and the amino acid at position 48 is I or V. In humZ270VH1 cons, the amino acid at position 5 is V or Q; the amino acid at position 69 is M or L; the amino acid at position 71 is T or V; the amino acid at position 73 is T or K; and/or the amino acid at position 75 is T or S. In an alternative humZ270VH1, humZ270VH1cons2 (SEQ ID NO:8), the amino acid at position 5 is V or Q; the amino acid at position 60 is S or A; the amino acid at position 63 is L or F; the amino acid at position 64 is Q or K; the amino acid at position 65 is G or D; the amino acid at position 66 is R or K; the amino acid at position 67 is V or A; the amino acid at position 69 is M or L; the amino acid at position 71 is T or V; the amino acid at position 73 is T or K; and/or the amino acid at position 75 is T or S.

FIG. 2 shows the CDRs of an exemplary humZ270 antibody, according to the Kabat definitions. The differences compared to murine Z270 CDRs are shown in bold. CDR_L1 corresponds to residues 24-34 of SEQ ID NO: 4. CDR_L2 corresponds to residues 50-56 of SEQ ID NO: 4. CDR_L3 corresponds to residues 89-97 of SEQ ID NO: 4. CDR_H1 corresponds to residues 31-35 of SEQ ID NO: 5. CDR_H2 corresponds to residues 50-66 of SEQ ID NO: 5. CDR_H3 corresponds to residues 99-114 of SEQ ID NO: 5. The residue numbering is referenced with respect to each SEQ ID NO recited.

FIGS. 4A-4J show different sequences derived from or based on Z270, (A) to (J), SEQ ID NOS:14-23, respectively. See Examples 2-5 for details.

FIG. 11 shows the strategy for standard CDR-grafting of murine Z270 Kabat CDRs H1-H3 into a VH1_18/JH6 heavy chain acceptor framework, without (humZ270H3) or with (humZ270VH4) back-mutations.

FIG. 12 shows an alignment between humZ270VH constructs in different human acceptor sequences, all with a partly human portion of CDR-H2.

FIG. 14 shows the selected residues for alanine-scan mutagenesis to identify critical paratope residues in the Z270 VL (SEQ ID NO: 1) and VH (SEQ ID NO: 2) segments.

DEFINITIONS

Figure 3A:
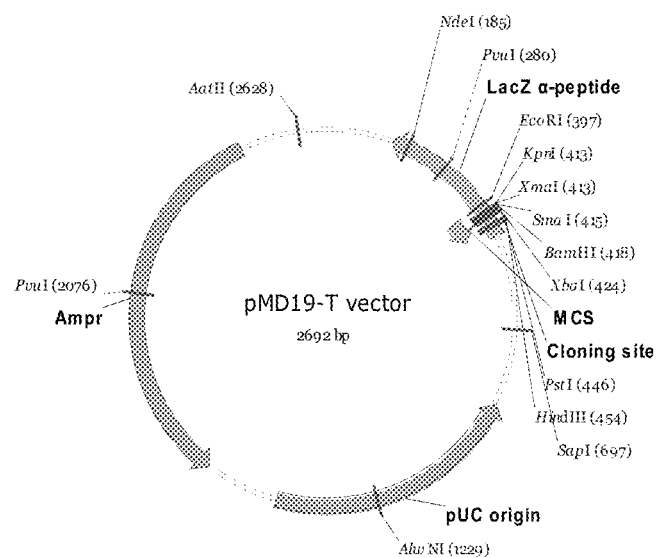
FIGS. 3A-H show plasmids referred to in the Examples. (A) pMD19-T vector map for TA cloning. (B) pJSV002 cloning vector map for transient expression. (C) Light chain is inserted into pJSV002 with murine kappa constant region. (D) pJSV002-mIgG1 variant containing murine IgG1 constant region. (E) pJSV002-mIgG1 Z270 H1 containing Z270 heavy chain variable region and IgG1 heavy chain constant region. (F) pJSV002-hKappa Z270 L11 containing light chain variable region and human kappa chain constant region. (G) pJSV002-IgG4-S241P. (H) pJSV002-IgG4-5241P Z270H1.

The term "antibody" herein is used in the broadest sense and specifically includes full-length monoclonal antibodies, polyclonal antibodies, multispecific antibodies (e.g., bispecific antibodies), and antibody fragments, so long as they exhibit the desired biological activity. Various techniques relevant to the production of antibodies are provided in, e.g., Harlow, et al., ANTIBODIES: A LABORATORY MANUAL, Cold Spring Harbor Laboratory Press, Cold Spring Harbor, N.Y. (1988).

An "antibody fragment" comprises a portion of a full-length antibody, preferably antigen-binding or variable regions thereof. Examples of antibody fragments include Fab, Fab', F(ab)$_2$, F(ab')$_2$, F(ab)$_3$, Fv (typically the VL and VH domains of a single arm of an antibody), single-chain Fv (scFv), dsFv, Fd fragments (typically the VH and CH1 domain), and dAb (typically a VH domain) fragments; VH, VL, VhH, and V-NAR domains; minibodies, diabodies, triabodies, tetrabodies, and kappa bodies (see, e.g., Ill et al., Protein Eng 1997; 10: 949-57); camel IgG; IgNAR; and multispecific antibody fragments formed from antibody fragments, and one or more isolated CDRs or a functional paratope, where isolated CDRs or antigen-binding residues or polypeptides can be associated or linked together so as to form a functional antibody fragment. Various types of antibody fragments have been described or reviewed in, e.g., Holliger and Hudson, Nat Biotechnol 2005; 23, 1126-1136;

WO2005040219, and published U.S. Patent Applications 20050238646 and 20020161201.

The term "antibody derivative", as used herein, comprises a full-length antibody or a fragment of an antibody, preferably comprising at least antigen-binding or variable regions thereof, wherein one or more of the amino acids are chemically modified, e.g., by alkylation, PEGylation, acylation, ester formation or amide formation or the like, e.g., for linking the antibody to a second molecule. This includes, but is not limited to, PEGylated antibodies, cysteine-PEGylated antibodies, and variants thereof.

An "immunoconjugate" comprises an antibody derivative associated with or linked to a second agent, such as a cytotoxic agent, a detectable agent, etc.

A "humanized" antibody is a human/non-human chimeric antibody that contains a minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit, or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody can optionally also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992), WO 92/02190, US Patent Application 20060073137, and U.S. Pat. Nos. 6,750,325, 6,632,927, 6,639,055, 6,548,640, 6,407,213, 6,180,370, 6,054,297, 5,929,212, 5,895,205, 5,886,152, 5,877,293, 5,869,619, 5,821,337, 5,821,123, 5,770,196, 5,777,085, 5,766,886, 5,714,350, 5,693,762, 5,693,761, 5,530,101, 5,585,089, and 5,225,539.

The term "hypervariable region" when used herein refers to the amino acid residues of an antibody that are responsible for antigen-binding. The hypervariable region generally comprises amino acid residues from a "complementarity-determining region" or "CDR" (residues 24-34 (L1), 50-56 (L2) and 89-97 (L3) in the light-chain variable domain and 31-35 (H1), 50-65 (H2) and 95-102 (H3) in the heavy-chain variable domain; Kabat et al. 1991, supra) and/or those residues from a "hypervariable loop" (residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol. 1987; 196:901-917). Typically, the numbering of amino acid residues in this region is performed by the method described in Kabat et al., supra. Phrases such as "Kabat position", "using Kabat numbering", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence. Unless otherwise indicated or contrary to context, the position of all amino acid residues in a VL or VH sequence described herein are according to Kabat.

"Framework region" or "FR" residues are those VH or VL residues other than the CDRs as herein defined.

A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

The term "substantially identical" in the context of two amino acid sequences means that the sequences, when optimally aligned, such as by the programs GAP or BEST-FIT using default gap weights, share at least about 50, at least about 60, at least about 70, at least about 80, at least about 90, at least about 95, at least about 98, or at least about 99 percent sequence identity. In one embodiment, residue positions that are not identical differ by conservative amino acid substitutions. Sequence identity is typically measured using sequence analysis software. Protein analysis software matches similar sequences using measures of similarity assigned to various substitutions, deletions and other modifications, including conservative amino acid substitutions. For instance, the publicly available GCG software contains programs such as "Gap" and "BestFit" which can be used with default parameters to determine sequence homology or sequence identity between closely related polypeptides, such as homologous polypeptides from different species of organisms or between a wild-type protein and a mutein thereof. See, e.g., GCG Version 6.1. Polypeptide sequences can also be compared using FASTA or ClustalW, applying default or recommended parameters. A program in GCG Version 6.1., FASTA (e.g., FASTA2 and FASTA3) provides alignments and percent sequence identity of the regions of the best overlap between the query and search sequences (Pearson, Methods Enzymol. 1990; 183:63-98; Pearson, Methods Mol. Biol. 2000; 132:185-219). Another preferred algorithm when comparing a sequence to a database containing a large number of sequences from various organisms, or when deducing the is the computer program BLAST, especially blastp, using default parameters. See, e.g., Altschul et al., J. Mol. Biol. 1990; 215:403-410; Altschul et al., Nucleic Acids Res. 1997; 25:3389-402 (1997); each herein incorporated by reference. "Corresponding" amino acid positions in two substantially identical amino acid sequences are those aligned by any of the protein analysis software mentioned herein, typically using default parameters.

An antibody having a "biological characteristic" of a reference antibody, (e.g., Z270), is one that possesses one or more of the biological characteristics of that antibody that distinguish it from other antibodies that bind to the same antigen (e.g. NKG2A). For example, an antibody with a biological characteristic of Z270 may block activation of NKG2A, and/or cross-compete with Z270 in binding the extracellular domain of NKG2A.

NKG2A (OMIM 161555, the entire disclosure of which is herein incorporated by reference) is a member of the NKG2 group of transcripts (Houchins, et al. (1991) J. Exp. Med. 173:1017-1020). NKG2A is encoded by 7 exons spanning 25 kb, showing some differential splicing. NKG2A is an inhibitory receptor found on the surface of subsets of NK cells, α/β T cells, γ/δ T cells, and NKT cells. Like inhibitory KIR receptors, it possesses an ITIM in its cytoplasmic domain. As used herein, "NKG2A" refers to any variant, derivative, or isoform of the NKG2A gene or encoded protein. Also encompassed are any nucleic acid or protein sequences sharing one or more biological properties or functions with wild type, full length NKG2A, and sharing at least 70%, 80%, 90%, 95%, 96%, 97%, 98%, 99%, or higher nucleotide or amino acid identity. Human NKG2A comprises 233 amino acids in 3 domains, with a cytoplasmic domain comprising residues 1-70, a transmembrane region comprising residues 71-93, and an extracellular region comprising residues 94-233, of the following sequence:

(SEQ ID NO: 11)
MDNQGVIYSDLNLPPNPKRQQRKPKGNKSSILATEQE-

ITYAELNLQKASQDFQGNDKTYHCKDLPSAPEKLIVGILGIICLILMASV

VTIVVIPSTLIQRHNNSSLNTRTQKARHCGHCPEEWITYSNSCY-

YIGKERRTWEESLLACTSKNSSLLSIDNEEEMKFLSIISPSS-

WIGVFRNSSHHPWVTMNGLAFKHEIKDSDNAELNCAVLQVNRLKSAQCGS

SIIYHCKHKL

NKG2C (OMIM 602891, the entire disclosure of which is herein incorporated by reference) and NKG2E (OMIM 602892, the entire disclosure of which is herein incorporated by reference) are two other members of the NKG2 group of transcripts (Gilenke, et al. (1998) Immunogenetics 48:163-173). NKG2C and NKG2E are activating receptors found on the surface of NK cells.

HLA-E (OMIM 143010, the entire disclosure of which is herein incorporated by reference) is a nonclassical MHC molecule that is expressed on the cell surface and regulated by the binding of peptides derived from the signal sequence of other MHC class I molecules. HLA-E binds natural killer (NK) cells and some T cells, binding specifically to CD94/NKG2A, CD94/NKG2B, and CD94/NKG2C (see, e.g., Braud et al. (1998) Nature 391:795-799, the entire disclosure of which is herein incorporated by reference). Surface expression of HLA-E is sufficient to protect target cells from lysis by CD94/NKG2A+NK, T, or NKT cell clones. As used herein, "HLA-E" refers to any variant, derivative, or isoform of the HLA-E gene or encoded protein. Also encompassed are any nucleic acid or protein sequences sharing one or more biological properties or functions with wild type, full length HLA-E, and sharing at least 70%, 80%, 90%, 95%, 96%, 97%, 98%, 99%, or higher nucleotide or amino acid identity.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome-binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

An "isolated" molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition). Commonly, a composition of an antibody molecule will exhibit 98%, 98%, or 99% homogeneity for antibody molecules in the context of all present peptide species in the composition or at least with respect to substantially active peptide species in the context of proposed use.

In the context of the present invention, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

DETAILED DESCRIPTION OF THE INVENTION

The present invention concerns antibodies binding to NKG2A. In one aspect, the antibody is a humanized version of antibody Z270, which is a murine monoclonal antibody that specifically binds NKG2A, but not to human NKG2C or NKG2E. Z270 can block the function of human CD94/NKG2A, and specifically induce killing of cells by CD94/NKG2A-restricted lymphocytes in a concentration-dependent fashion.

The invention provides, e.g., humZ270 variants in which at least a portion of a VH CDR such as the CDR-H2 is identical to the corresponding portion of the human VH acceptor sequence, thus reducing the immunogenicity of the humanized antibody. Surprisingly, such humanized variants can be more effective in potentiating the cytotoxicity of a CD94/NKG2A-expressing cytotoxic lymphocyte than the murine or a chimeric form of Z270. In other aspects, the invention provides antibodies having CDRs comprising certain antigen-binding residues corresponding to those in murine antibody Z270, and human framework sequences.

These and other aspects are described in more detail in the following sections and in the Examples.

Humanized Anti-NKG2A Antibodies

Methods for humanizing non-human antibodies have been described in the art. Generally, in a humanization process, nucleotides encoding the interaction-regions of a murine antibody can be cloned into a cDNA-vector encoding human IgG, which can be done such that a chimeric antibody is generated consisting of a human IgG backbone harbouring the murine CDRs. Such chimeric antibodies may exhibit a lower affinity, lower stability, or other undesired features in comparison with the original murine antibody, and may also be immunogenic. Therefore, individual amino acids in the chimeric Ab may need to be optimized to obtain a functional mAb of high quality for therapeutic applications in humans.

Typically, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al, Nature, 321: 522-525 (1986); Riechmann et al., Nature, 332: 323-327 (1988); Verhoeyen et al., Science, 239: 1534-1536 (1988)), by substituting hypervariable region sequences for the corresponding sequences of a human "acceptor" antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

Another method for making humanized antibodies is described in U.S. patent application publication 2003/0017534, wherein humanized antibodies and antibody preparations are produced from transgenic non-human animals. The non-human animals are genetically engineered to contain one or more humanized immunoglobulin loci that are capable of undergoing gene rearrangement and gene conversion in the transgenic non-human animals to produce diversified humanized immunoglobulins.

The choice of human variable domains, both light and heavy, to be used in making the humanized antibodies is very important to reduce antigenicity. According to the so-called "best-fit" method, the sequence of the variable domain of a rodent antibody is screened against a library of known human variable-domain sequences or a library of human germline sequences. The human sequence that is closest to that of the rodent can then be accepted as the human framework region for the humanized antibody (Sims et al., J. Immunol. 1993; 151:2296 et seq.; Chothia et al, Chothia and Lesk, J. Mol. Biol. 1987; 196:901-917). Another method uses a particular framework region derived from the consensus sequence of all human antibodies of a particular subgroup of light or heavy chains. The same framework may be used for several different humanized antibodies (Carter et al., PNAS USA, 1992; 89:4285 et seq.; Presta et al., J Immunol 1993; 151:2623 et seq.). Other methods designed to reduce the immunogenicity of the antibody molecule in a human patient include veneered antibodies (see, e.g., U.S. Pat. No. 6,797,492 and U.S. patent application publications 20020034765 and 20040253645) and antibodies that have been modified by T-cell epitope analysis and removal (see, e.g., U.S. patent application publications 20030153043 and U.S. Pat. No. 5,712,120).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Example 1 below describes the design of exemplary humanized anti-NKG2A antibodies that bind NKG2A, and the analysis is, at least in part, illustrated in FIG. 1. As shown in FIG. 1, in one humZ270 antibody of the invention, the C-terminal portion of CDR-H2 (corresponding to Kabat residues 61-65) are identical to the corresponding portion of the human acceptor sequence. Further, as described in the figure legend, a humZ270VL sequence (SEQ ID NO:4) may optionally comprise mutations in one or both of the indicated FR residues L46 and I48, and a humZ270VH sequence (SEQ ID NO:5) may optionally comprise mutations in one or more of the indicated FR residues V5, M69, T71, T73 and T75, with amino acid numbering according to Kabat. Table 1 describes exemplary humZ270VL and humZ270VH variants comprising exemplary human-to-murine back-mutations in the humZ270VH and humZ270VL FR sequences, as well as exemplary combinations of FR mutations. In Table 1 and elsewhere herein, the amino acid positions are designated according to Kabat, in which amino acids V5, M69, T71, T73, and T75 in the humZ270VH domain correspond to amino acids V5, M70, T72, T74, and T76 in SEQ ID NO:5, SEQ ID NO:7, SEQ ID NO:8, or other exemplary humZ270VH sequences described herein.

TABLE 1 humZ270VL and humZ270VH variants comprising exemplary FR back-mutations in native or consensus humZ270VL (SEQ ID NO: 4 or 6) and/or humZ270VH (SEQ ID NO: 5, 7, or 8) sequences.

| humZ270VL Variants | humZ270VH Variants |
|---|---|
| None | None |
| L46F | V5Q |
| I48V | M69L |
| L46F and I48V | T71V |
|  | T73K |
|  | T75S |
|  | V5Q and M69L |
|  | V5Q and T71V |
|  | V5Q and T73K |
|  | V5Q and T75S |
|  | M69L and T71V |
|  | M69L and T73K |
|  | M69L and T75S |
|  | T71V and T73K |

TABLE 1-continued humZ270VL and humZ270VH variants comprising exemplary FR back-mutations in native or consensus humZ270VL (SEQ ID NO: 4 or 6) and/or humZ270VH (SEQ ID NO: 5, 7, or 8) sequences.

| humZ270VL Variants | humZ270VH Variants |
|---|---|
| | T71V and T75S |
| | T73K and T75S |
| | V5Q, T73K and T75S |
| | V5Q, T71V and T75S |
| | V5Q, T71V and T73K |
| | V5Q, M69L and T75S |
| | V5Q, M69L and T73K |
| | V5Q, M69L and T71V |
| | T71V, T73K and T75S |
| | M69L, T73K and T75S |
| | M69L, T71V and T75S |
| | M69L, T71V and T73K, |
| | V5Q, M69L, T71V and T73K, |
| | V5Q, M69L, T71V and T75S, |
| | V5Q, M69L, T73K and T75S, |
| | V5Q, T71V, T73K and T75S, |
| | M69L, T71V, T73K and T75S, |
| | V5Q, M69L, T71V, T73K and T75S |

Accordingly, the present invention provides for humanized versions of an anti-NKG2A antibody produced by the Z270 hybridoma, as well as for humanized versions of non-human antibodies sharing biological characteristics and/or substantial sequence identity with Z270. In another embodiment, the monoclonal antibody or a fragment or derivative thereof is capable of binding to a non-human primate NKG2A.

The humanized antibody herein comprises non-human hypervariable region or CDR residues incorporated into human VH and VL domains.

In one aspect, the invention provides a humanized antibody comprising antigen-binding residues from the CDRs of murine antibody Z270 in a human acceptor framework, wherein at least the 6 C-terminal amino acid residues of the CDR-H2 are the same as those in the human acceptor sequence. Such humanized antibodies can be more effective than the original murine Z270 antibody or a chimeric version thereof in, e.g., potentiating the cytotoxic activity of a CD94/NKG2A-expressing cytotoxic lymphocyte, such as, e.g., an NK-cell, an NKT-cell, an α/β T-cell, and/or a γ/δ T-cell, or of a population of CD94/NKG2A-expressing cytotoxic lymphocytes.

Typical antibodies of the invention comprise antigen-binding residues corresponding to, or portions of the Z270 CDR-H2 and CDR-H3 that comprise, residues D52, D54, R94, F99, T(100C), and W(100F) of SEQ ID NO:2 or SEQ ID NO:5, which have been shown in the Examples to be critical for antigen-binding. Optionally, the antibodies also comprise VH residues N35, Y53, E56, D98, V(100A), and L(100D).

In another aspect, a humanized antibody comprises a CDR-H1 sequence corresponding to residues 31-35 of SEQ ID NO:5 and a CDR-H3 sequence corresponding to residues 95-102 of SEQ ID NO:5, wherein the CDR-H2 sequence comprises residues 50-59 of SEQ ID NO:5. In such humanized antibodies, the VH region can have, for example 50% or more sequence identity to SEQ ID NO:5, such as at least 60%, at least 70%, or at least 75% sequence identity. Exemplary humanized VH domains having such sequences are described in the examples and below.

In one embodiment, in such humanized antibodies, the amino acid at position 5 of the VH region can be V or Q; the amino acid at position 69 of the VH region can be M or L; the amino acid at position 71 of the VH region can be T or V; the amino acid at position 73 of the VH region can be T or K; and/or the amino acid at position 75 of the VH region can be T or S. In separate embodiments, the VH region comprises V5 or Q5, M69 or L69, T71 or V71, T73, or K71, and/or T75 or S75 residues. In another embodiment, the amino acid at position 69 is L. In another additional or alternative embodiment, the amino acid at position 71 is V.

The humanized antibody may comprise a VH human acceptor framework from a human acceptor sequence selected from, e.g., VH1_18, VH5_a, VH5_51, VH1J, and VH1_46, and the J-segment is JH6, such as, e.g., a VH1_18, VH5_a, VH5_51, or VH1_f, or other human germline VH framework sequences known in the art. In one embodiment, the VH segment is VH1_18. In a particular embodiment, the VH region comprises the sequence of SEQ ID NO:8. In another particular embodiment, the VH region comprises the sequence of SEQ ID NO:7. For example, the VH region may comprise the sequence of SEQ ID NO:5.

The VL region human acceptor sequence may be, e.g., VKI_02/JK4. In a particular embodiment, the VL region comprises SEQ ID NO:4.

In one aspect, a humanized antibody of the invention comprises a CDR-H2 comprising a murine portion consisting of residues 50-59 of SEQ ID NO:2 linked to a CDR-H3 consisting of residues 95-102 of SEQ ID NO:2 via suitable FR sequences.

As described herein, in one embodiment, the humanized antibody comprises no FR substitution in the VH domain. In another embodiment, the humanized antibody comprises a VH domain FR substitution at one or more positions selected from 5, 69, 71, 73 and 75, utilizing the variable domain numbering system according to Kabat. In another embodiment, the humanized antibody comprises VH domain FR substitutions at two or more of positions 5, 69, 71, 73 and 75; and in other embodiments, at three, four, or all of such positions. In separate and independent embodiments, the humanized antibody comprises one VH domain FR substitution at a position selected from 5, 69, 71, 73 and 75. In other separate and independent embodiments, the humanized antibody comprises VH domain FR substitutions at positions 5 and 69, or 5 and 71, or 5 and 73, or 5 and 75, or 69 and 71, 69 and 73, or 69 and 75, or 71 and 73, or 71 and 75, or 73 and 75, or 5, 69 and 71, or 5, 69 and 73, or 5, 69 and 75, or 69, 71 and 73, or 69, 71 and 75, or 71, 73, and 75, or 5, 69, 71, and 73, or 5, 69, 71, and 75, or 5, 71, 73, and 75, or 69, 71, 73, and 75, or 5, 69, 71, 73, and 75. Fewer rather than more framework substitutions can minimize immunogenicity, but binding efficacy may be an important consideration for some applications. Thus, preferred substitutions are back-mutations, i.e., mutations which replace an amino acid at a certain position in the human FR with the amino acid at the corresponding position in a non-human donor FR. Thus, in separate and independent embodiments, the VH domain amino acid substitution at position 5 is V5Q, the amino acid substitution at position 69 is M69L, the amino acid substitution at position 71 is T71V, the amino acid substitution at position 73 is T73K, and the amino acid substitution at position 75 is T75S. In a particular embodiment, the humanized antibody comprises a V at position 71 and/or an L at position 69.

The humanized antibody herein also comprises non-human hypervariable region residues incorporated into a human VL domain. In one embodiment, the humanized antibody comprises no FR substitution in the VL domain. In another embodiment, the humanized antibody comprises a VL domain FR substitution at one of positions 46 and 48, utilizing the variable domain numbering system according to Kabat. In another embodiment, the humanized antibody comprises VL domain FR substitutions both of positions 46 and 48. Preferred substitutions are back-mutations, i.e., mutations which replace an amino acid at a certain position in the human FR with the amino acid at the corresponding position in a non-human donor FR. Thus, in separate and independent embodiments, the VL domain amino acid substitution at position 46 is L46F, and the VL domain amino acid substitution at position 48 is I48V.

An exemplary humanized antibody comprises a VH domain comprising a CDR-H1 sequence corresponding to residues 31-35 of SEQ ID NOS:5 or 7, a CDR-H2 sequence corresponding to residues 50-66 of SEQ ID NOS:5 or 7, and a CDR-H3 sequence corresponding to residues 95-102 of SEQ ID NOS:5 or 7. The humanized antibody may further comprise an amino acid at Kabat position 5 which is V or Q, an amino acid at Kabat position 69 which is M or L, an amino acid at Kabat position 71 which is T or V, an amino acid at Kabat position 73 is T or K, and/or an amino acid at Kabat position 75 which is T or S, in the VH domain. In one embodiment, the VH domain comprises a framework region substitution in at least one Kabat position selected from the group consisting of 5, 69, 71, 73, and 75, e.g., corresponding to any of the VH FR substitutions, or combinations thereof, listed in Table 1. In one embodiment, the VH domain comprises the sequence of SEQ ID NO:7. In another embodiment, the VH domain comprises the sequence of SEQ ID NO:5.

An exemplary humanized antibody may also or alternatively comprise a VL domain comprising a CDR-L1 sequence corresponding to residues 24-34 of SEQ ID NO:4, a CDR-L2 sequence corresponding to residues 50-56 of SEQ ID NO:4, and an CDR-L3 sequence corresponding to residues 89-97 of SEQ ID NO:4. The humanized antibody may further comprise an amino acid at Kabat position 46 which is L or F and/or an amino acid at Kabat position 48 which is I or V. In one embodiment, the VL domain comprises a framework region substitution in at least one Kabat position selected from 46 and 48, e.g., corresponding to any of the VL FR substitutions, or combinations thereof, listed in Table 1. In one embodiment, the VL domain comprises the amino acid sequence of SEQ ID NO:4. In another embodiment, the VL domain comprises the sequence of SEQ ID NO:6.

In another aspect, the invention provides a humanized antibody that binds human NKG2A, the antibody comprising a VH domain that comprises the amino acid sequence of SEQ ID NO:5, optionally with one or more FR substitutions at Kabat positions 5, 69, 71, 73, and/or 75. The optional FR substitutions can be selected from, e.g., V5Q, M69L, T71V, T73K, and/or T75S, as well as any combination thereof. Such a humanized antibody may also or alternatively comprise a VL domain that comprises the amino acid sequence of SEQ ID NO:4, optionally with one or more FR substitutions at Kabat positions 46 and/or 48. The optional FR substitutions can be selected from, e.g., L46F and/or I48V.

Optionally, in a particular aspect, the VH domain comprises amino acid modifications of one or more CDR residues, e.g. where the modifications essentially maintain or improve affinity of the antibody. For example, the antibody variant may have one, two, three, or from one to about seven amino acid substitutions in the above VH CDR sequences.

In a particular aspect, amino acids in the humanized antibody VH CDRs which are different from the amino acids at the corresponding positions in the non-human donor VH CDRs can be substituted to improve the binding properties and/or stability of the humanized antibody. For example, one or more of these amino acids can be substituted for the amino acid at the corresponding position(s) in the non-human donor VH CDR. In one embodiment, the variant antibody comprises CDRH2 substitutions at one or more positions selected from 60, 63, 64, and 65, according to Kabat (corresponding to positions 61, 64, 65, and 66 in SEQ ID NO:5 or 7). In separate and independent embodiments, the antibody variant comprises a CDRH2 amino acid substitution at one position selected from 60, 63, 64, and 65. In other separate and independent embodiments, the antibody variant comprises CDRH2 amino acid substitution at positions 60 and 63, or 60 and 64, or 60 and 65, or 63 and 64, or 63 and 65, or 64 and 65, or 60, 63, and 64, or 60, 63, and 65, or 60, 64, and 65, or 63, 64, and 65, or 60, 63, 64, and 65. Preferred substitutions are back-mutations, i.e., mutations which replace an amino acid at a certain position in the humanized CDR with the amino acid at the corresponding position in a non-human donor CDR. Thus, in separate and independent embodiments, the CDRH2 amino acid substitution at position 60 is A60S, the amino acid substitution at position 63 is L63F, the amino acid substitution at position 64 is Q64K, and the amino acid substitution at position 65 is G65D. In aspects where the antibody variant comprises one or more of the CDRH2 amino acid substitutions A60S, L63F, Q64K, and G65D, the antibody variant comprises the VH FR amino acid substitutions at positions 66 and 67 according to Kabat, optionally in conjunction with one or more of the VH FR substitutions previously described. Preferably, the amino acid substitutions are R66K and V67A. For example, in one embodiment, the antibody variant comprises a VH domain comprising a CDR-H1 sequence corresponding to residues 31-35 of SEQ ID NO:5, a CDR-H2 sequence corresponding to residues 50-66 of SEQ ID NO:5, and a CDR-H3 sequence corresponding to residues 95-102 of SEQ ID NO:5, with A60S, L63F, Q64K, G65D, R66K and V67A "back-mutations," optionally in conjunction with additional amino acid modifications.

In another particular aspect, the invention provides for a humanized antibody that binds human NKG2A, the antibody comprising a VH domain that comprises non-human CDR residues incorporated into a human VH domain, the VH domain comprising a CDR-H1 sequence corresponding to residues 31-35 of SEQ ID NO:8, a CDR-H2 sequence corresponding to residues 50-66 of SEQ ID NO:8, and a CDR-H3 sequence corresponding to residues 95-102 of SEQ ID NO:8, wherein the amino acids at Kabat positions 63, 64, 65, 66, and 67 are F, K, D, K, A, respectively. In one embodiment, the VH domain comprises the amino acid sequence of SEQ ID NO:8. In another embodiment, the residue at Kabat position 60 is A. In another embodiment, the residue at Kabat position 60 is S, and the humanized antibody comprises the CDR-H1, —H2, and H3 sequences of Z270, with FR back-mutations in the two amino acids adjacent to the C-terminal end of CDR-H2. The humanized antibodies described in this section may further comprise FR back-mutations in other residues, e.g., at Kabat positions 5, 69, 71, 73, and/or 75, as described herein.

In another aspect, the invention provides for a humanized antibody wherein the Kabat CDRs in the VH region all derive from the murine Z270VH (SEQ ID NO:2), further comprising S60A, F63L, $K_{64}Q$, and/or D65G mutations. In one embodiment, the humanized antibody comprises all of the mutations S60A, F63L, $K_{64}Q$, and/or D65G.

The humanized antibody can also comprise a VL domain comprising a CDR-L1 sequence corresponding to residues 24-34 of SEQ ID NO:6, a CDR-L2 sequence corresponding to residues 50-56 of SEQ ID NO:6, and an CDR-L3 sequence corresponding to residues 89-97 of SEQ ID NO:6, e.g., in addition to the VH domain CDRs described above. In one embodiment, the VL domain of the humanized antibody comprises the amino acid sequence of SEQ ID NO:6. In another embodiment, the VL domain of the humanized antibody comprises the amino acid sequence of SEQ ID NO:4. Optionally, such a humanized antibody comprises amino acid modifications of one or more VL CDR residues, e.g., where the modifications essentially maintain or improve affinity of the antibody. For example, the antibody variant may have one, two, three, or from one to about seven amino acid substitutions in the above VL CDR sequences.

The present application also contemplates affinity-matured antibodies that bind anti-NKG2A, containing additional CDR or FR mutations that improve the affinity of the humanized antibody for the antigen. Methods for preparing such affinity-matured antibodies are known in the art. The parent antibody may be a humanized antibody, e.g., one comprising the VL/VH sequences of SEQ ID NOS:4 and 5 (optionally with one or more of the CDRH2 and/or FR substitutions described herein), or one comprising the consensus VL/VH sequences of SEQ ID NOS:6 and 7, respectively. The affinity-matured antibody preferably binds to NKG2A with an affinity comparable or superior to that of murine Z270, e.g. from at least about one-, about two- or about four-fold to about 100-fold or about 1000-fold improved affinity, e.g. as assessed using a binding assay as described below.

In another aspect, the invention provides humanized antibodies that comprise a VH domain having at least about 50%, at least about 70%, at least about 80% sequence identity (e.g., at least about 85%, 90%, 95%, 97%, or more identity) to the VH domain of Z270, humZ270, humZ270cons, and/or humZ270cons2 (SEQ ID NOS:2, 5, 7, and 8, respectively). In another particular aspect, the invention provides a humanized antibody that binds NKG2A, comprising a VH domain that comprises non-human CDR residues incorporated into a human VH domain, wherein the VH domain is at least about 50% identical to humZ270VH1 (SEQ ID NO:5). In one embodiment, the VH domain is at least 90% identical to SEQ ID NO:5. For example, the humanized antibody may comprise a CDR-H1 sequence corresponding to residues 31-35 of SEQ ID NO:5, a CDR-H2 sequence corresponding to residues 50-66 of SEQ ID NO:5, and a CDR-H3 sequence corresponding to residues 95-102 of SEQ ID NO:5. The humanized antibody may also or alternatively comprise a V or Q at Kabat position 5, an M or L at Kabat position 69, a T or V at Kabat position 71, a T or K at Kabat position 73, and a T or S at Kabat position 75, in the VH domain.

In another aspect, the invention provides an antibody molecule that also or alternatively comprises a VL domain having at least about 50%, at least about 70%, or at least about 80% sequence identity (e.g., at least about 85%, 90%, 95%, 97%, or more identity) to the VL domain of Z270, humZ270, and/or humZ270 cons (SEQ ID NOS:1, 4, and 6, respectively). In another particular aspect, the invention provides a humanized antibody that binds NKG2A, comprising a VL region that comprises non-human CDR residues incorporated into a human VL domain, wherein the VL domain is at least 50% identical to SEQ ID NO:4. In one embodiment, the VL region is at least 90% identical to SEQ ID NO:4. For example, the humanized antibody may comprise a CDR-L1 sequence corresponding to residues 24-34 of SEQ ID NO:4, a CDR-L2 sequence corresponding to residues 50-56 of SEQ ID NO:4, and an CDR-L3 sequence corresponding to residues 89-97 of SEQ ID NO:4. The humanized antibody may also or alternatively comprise a L or F at Kabat position 46 and/or an I or V at Kabat position 48, in the VL domain.

In another aspect, the invention provides an isolated humanized antibody that specifically binds NKG2A and that comprises either (a) CDR-L1, CDR-L2, and/or CDR-L3 sequences of Z270 VL (SEQ ID NO:1), humZ270 VL (SEQ ID NO:4), or humZ270 VL cons (SEQ ID NO:6) or (b) CDR-H1, CDR-H2, and/or CDR-H3 sequences of Z270 VH (SEQ ID NO:2), humZ270 (SEQ ID NO:5), humZ270 cons (SEQ ID NO:7), or humZ270 cons2 (SEQ ID NO:8). In another aspect, the invention provides an antibody molecule that comprises at least a complete set of VH CDRs from Z270, humZ270, or humZ270 cons, wherein the 6 C-terminal amino acids are identical to those of the human acceptor sequence. In a particular aspect, the invention provides an antibody molecule that comprises CDR-H1, CDR-H2 (or an N-terminal portion thereof), and CDR-H3 of Z270, humZ270, or humZ270 cons and at least some of CDR-L1, CDR-L2, and CDR-L3 of Z270, humZ270, or humZ270 cons. In a more particular aspect, the invention provides an antibody molecule wherein the antibody molecule comprises CDR-L1, CDR-L2, and CDR-L3, CDR-H1, CDR-H2, and CDR-H3 of Z270, humZ270, or humZ270 cons, wherein CDR-L1 is linked to CDR-L2, CDR-L2 is linked to CDR-L3, CDR-H1 is linked to CDR-H2, and CDR-H2 is linked to CDR-H3, via suitable FR sequences.

In a particular aspect, the invention provides antibody molecules that comprise essentially all of the VH and/or VL domains of humZ270, humZ270 cons, or humZ270 cons2.

A humanized anti-NKG2A antibody according to the invention may comprise any full-length or partial heavy-chain (HC) comprising a humZ270VH described herein and/or any full-length or partial HC comprising a humZ270VH may be combined with any humZ270VL described herein in, and the resulting antibody or fragment tested for antigen binding, functional effects on CD94/NKG2A-expressing cells, and/or immunogenicity.

Various forms of the humanized antibody are contemplated. For example, the humanized antibody may be an antibody fragment, such as a Fab or other type of fragment described herein. Alternatively, the humanized antibody may be a full-length or intact antibody, such as a full-length or intact IgG1 or IgG4 antibody. In one embodiment, the humanized antibody is a full-length IgG4 antibody or a fragment thereof.

In one aspect, the present invention provides a humanized antibody characterized by: a) specifically binding to NKG2A; b) not specifically binding to an Fc receptor; and c) when bound to NKG2A on a human NK cell, causing said NK cell to lyse a target human cell bearing HLA-E on the target cell surface, when said target cell comes into contact with said NK cell. In one embodiment, the humanized antibody comprises a mouse or human IgG1 constant region that has been modified to prevent binding to an Fc receptor, or a human IgG4 constant region. Such antibodies, as well as antibody fragments that do not bind an Fc receptor, are particularly useful in applications where it is desired to activate NK cells (e.g. cancer, infectious disease), without leading to the depletion of the NK cell themselves, as might be mediated by antibody dependent cell cytotoxicity, and can be referred to as "nondepleting" antibodies.

In another aspect, the humanized antibody comprises a mouse or human IgG1 constant region that binds an Fc receptor, or a human IgG1, 2, 3 or 4 constant region has been modified to bind an Fc receptor or increase binding to an Fc receptor, or a human IgG$_4$ constant region. In another embodiment, the monoclonal antibody or a fragment thereof is linked to a moiety that is toxic to a cell to which the antibody is bound. Such antibodies are particularly useful in applications where it is desired to deplete an NK cell, useful in certain applications such as NK-LDGL (NK-type lymphoproliferative disease of granular lymphocytes; alternatively called NK-LGL), and can be referred to as "depleting" antibodies.

For recombinant production of humanized antibodies, humanized VH and VL regions, or variant versions thereof, can be cloned into expression vectors encoding full-length or truncated constant regions from a human antibody according to standard recombinant methods (see, e.g., Sambrook et al., Molecular Cloning: A Laboratory Manual, 2$^{nd}$ Ed., Cold Spring Harbor Laboratory, Cold Spring Harbor, N.Y., 1989). The result is a transfected cell line that expresses and secretes the humanized antibody molecule of interest, comprising the selected VH and VL regions and constant regions. cDNA sequences encoding the constant regions of human antibodies are known. Exemplary cDNA sequences available via, e.g., GenBank, each of which incorporated by reference in its entirety, are as follows:

Human IgG1 constant heavy chain region: GenBank accession No.: J00228;

Human IgG2 constant heavy chain region: GenBank accession No.: J00230;

Human IgG3 constant heavy chain region: GenBank accession No.: X04646;

Human IgG4 constant heavy chain region: GenBank accession No.: K01316; and

Human kappa light chain constant region: GenBank accession No.: J00241.

If desired, the class of a humanized antibody may also be "switched" by known methods. For example, an antibody that was originally produced as an IgM molecule may be class switched to an IgG antibody. Class switching techniques also may be used to convert one IgG subclass to another, e.g., from IgG1 to IgG2. Thus, the effector function of the antibodies of the invention may be changed by isotype switching to, e.g., an IgG1, IgG2, IgG3, IgG4, IgD, IgA, IgE, or IgM antibody for various therapeutic uses.

The constant region may further be modified according to known methods. For example, in an IgG4 constant region, residue S241 may be mutated to a proline (P) residue to allow complete disulphide bridge formation at the hinge (see, e.g., Angel et al., Mol. Immunol. 1993; 30:105-8).

Antibody Fragments

The humanized antibodies of the invention may be prepared as antibody fragments, or antibody fragments may be prepared from humanized full-length antibodies.

Various techniques have been developed for the production of antibody fragments of humanized antibodies. Traditionally, these fragments were derived via proteolytic digestion of full-length antibodies (see, e.g., Morimoto et al., Journal of Biochemical and Biophysical Methods, 24:107-117 (1992); and Brennan et al., Science, 229:81 (1985)). However, these fragments can now be produced directly by recombinant host cells. Alternatively, Fab'-SH fragments can be directly recovered from *E. coli* and chemically coupled to form F(ab')2 fragments (Carter et al., Bio/Technology, 10:163-167 (1992)). According to another approach, F(ab')2 fragments can be isolated directly from recombinant host cell culture. Other techniques for the production of antibody fragments will be apparent to the skilled practitioner. In other embodiments, the antibody of choice is a single-chain Fv fragment (scFv). See WO 1993/16185; U.S. Pat. Nos. 5,571,894; and 5,587,458. The antibody fragment may also be a "linear antibody", e.g., as described in U.S. Pat. No. 5,641,870, for example. Such linear antibody fragments may be monospecific or bispecific.

Bispecific antibodies are antibodies that have binding specificities for at least two different epitopes. Methods for making bispecific antibodies are known in the art, and traditional production of full-length bispecific antibodies is usually based on the coexpression of two immunoglobulin heavy-chain-light-chain pairs, where the two chains have different specificities (Millstein et al., Nature, 305: 537-539 (1983)). In the bispecific antibodies according to the present invention, at least one binding epitope is on the NKG2A protein. The anti-NKG2A-binding "arm" may be combined with an "arm" that binds to a triggering molecule on a leukocyte such as a T-cell receptor molecule (e.g. CD2 or CD3), or Fc receptors for IgG (Fcgamma-R), such as Fc-gamma-RI (CD64), Fc-gamma-RII (CD32) and Fc-gamma-RIII (CD16), so as to focus cellular defense mechanisms to the NKG2A-expressing cell. Bispecific antibodies may also be used to localize cytotoxic agents to cells that express NKG2A. These antibodies possess a NKG2A-binding arm and an arm that binds the cytotoxic agent (e.g. saporin, anti-interferon-alpha, vinca alkaloid, ricin A chain, methotrexate, or radioactive isotope hapten). Bispecific antibodies can be prepared as full-length antibodies or antibody fragments (e.g. F(ab')2 bispecific antibodies). Antibodies with more than two valencies are contemplated. For example, trispecific antibodies can be prepared. Tutt et al., J. Immunol, 147: 60 (1991).

Typical antibodies, antibody fragments and multispecific antibodies of the invention comprise portions of the CDR-H2 and CDR-H3 that comprise residues D52, D54, R94, F99, T(100C), and W(100F) of SEQ ID NO:2 or SEQ ID NO:5, which have been shown to be critical for antigen-binding (see Examples). Optionally, the humanized antibody fragments and multispecific antibodies also comprise Z270 heavy chain residues N35, Y53, E56, D98, V(100A), and L(100D). In one aspect, a humanized antibody fragment or multispecific antibody of the invention comprises residues 50-59 of the CDR-H2 and residues 95-102 of the CDR-H3 of SEQ ID NO:2 or SEQ ID NO:5. In one embodiment, the humanized antibody fragment or multispecific antibody does not comprise one, two, or all of Z270 CDR-L1, CDR-L2, and CDR-L3. In an additional or alternative embodiment, the antibody fragment or multispecific antibody does not comprise the Z270 CDR-H1.

Antibody Derivatives

Antibody derivatives within the scope of this invention include humanized antibodies conjugated or covalently bound to a second agent.

For example, in one aspect, the invention provides immunoconjugates comprising a humanized antibody conjugated or covalently bonded to a cytotoxic agent. The term "cytotoxic agent" as used herein is a molecule that is capable of killing a cell bearing a NKG2A receptor on its cell surface. Any type of moiety with a cytotoxic or cytoinhibitory effect can be conjugated to the present antibodies to form a cytotoxic conjugate of the present invention and to inhibit or kill specific NK receptor expressing cells, including therapeutic radioisotopes, toxic proteins, toxic small molecules, such as drugs, toxins, immunomodulators, hormones, hormone antagonists, enzymes, oligonucleotides, enzyme inhibitors, therapeutic radionuclides, angiogenesis inhibitors, chemotherapeutic drugs, vinca alkaloids, anthracyclines, epidophyllotoxins, taxanes, antimetabolites, alkylating agents, antibiotics, COX-2 inhibitors, SN-38, antimitotics, antiangiogenic and apoptotoic agents, particularly doxorubicin, methotrexate, taxol, CPT-11, camptothecans, nitrogen mustards, gemcitabine, alkyl sulfonates, nitrosoureas, triazenes, folic acid analogs, pyrimidine analogs, purine analogs, platinum coordination complexes, *Pseudomonas* exotoxin, ricin, abrin, 5-fluorouridine, ribonuclease (RNase), DNase I, Staphylococcal enterotoxin-A, pokeweed antiviral protein, gelonin, diphtherin toxin, *Pseudomonas* exotoxin, and *Pseudomonas* endotoxin and others (see, e.g., Remington's Pharmaceutical Sciences, 19th Ed. (Mack Publishing Co. 1995); Goodman and Gilman's The Pharmacological Basis of Therapeutics (McGraw Hill, 2001); Pastan et al. (1986) Cell 47:641; Goldenberg (1994) Cancer Journal for Clinicians 44:43; U.S. Pat. No. 6,077,499; the entire disclosures of which are herein incorporated by reference). It will be appreciated that a toxin can be of animal, plant, fungal, or microbial origin, or can be created de novo by chemical synthesis.

In another embodiment, the antibody is derivatized with a radioactive isotope, such as a therapeutic radionuclide or a radionuclide suitable for detection purposes. Any of a number of suitable radioactive isotopes can be used, including, but not limited to, 1-131, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-105, Palladium-109, Praseodymium-143, Promethium-149, Erbium-169, Iridium-194, Gold-198, Gold-199, and Lead-211. In general, the radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Also preferred are radionuclides that substantially decay with generation of alpha-particles.

In other embodiments, the second agent is a detectable moiety, which can be any molecule that can be quantitatively or qualitatively observed or measured. Examples of detectable markers useful in the conjugated antibodies of this invention are radioisotopes, fluorescent dyes, or a member of a complementary binding pair, such as a member of any one of: and antigen/antibody (other than an antibody to NKG2A), lectin/carbohydrate; avidin/biotin; receptor/ligand; or molecularly imprinted polymer/print molecule systems.

The second agent may also or alternatively be a polymer, intended to increase the circulating half-life of the humanized antibody, for example. Exemplary polymers and methods to attach such polymers to peptides are illustrated in, e.g., U.S. Pat. Nos. 4,766,106; 4,179,337; 4,495,285; and 4,609,546. Additional illustrative polymers include polyoxyethylated polyols and polyethylene glycol (PEG) moieties (e.g., a full-length antibody or antibody fragment can be conjugated to one or more PEG molecules with a molecular weight of between about 1,000 and about 40,000, such as between about 2000 and about 20,000, e.g., about 3,000-12,000).

The cytotoxic agents or other compounds can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (see, e.g., Yu et al. (1994) Int. J. Cancer 56: 244; Wong, Chemistry of Protein Conjugation and Cross-linking (CRC Press 1991); Upeslacis et al., "Modification of Antibodies by Chemical Methods," in Monoclonal antibodies: principles and applications, Birch et al. (eds.), pages 187-230 (Wiley-Liss, Inc. 1995); Price, "Production and Characterization of Synthetic Peptide-Derived Antibodies," in Monoclonal antibodies: Production, engineering and clinical application, Ritter et al. (eds.), pages 60-84 (Cambridge University Press 1995), Cattel et al. (1989) Chemistry today 7:51-58, Delprino et al. (1993) J. Pharm. Sci 82:699-704; Arpicco et al. (1997) Bioconjugate Chemistry 8:3; Reisfeld et al. (1989) Antibody, Immunicon. Radiopharm. 2:217; the entire disclosures of each of which are herein incorporated by reference).

Alternatively, a fusion protein comprising the anti-NKG2A antibody and a second (cytotoxic or other) polypeptide agent may be made, e.g. by recombinant techniques or peptide synthesis.

Binding Assays

The present invention provides for antibodies that bind human NKG2A, in particular humanized versions of an anti-NKG2A antibody produced by the Z270 hybridoma.

Any of a wide variety of assays can be used to assess binding of an antibody to human NKG2A. Protocols based upon ELISAs, radioimmunoassays, Western blotting, BIA-CORE, and other competition assays, inter alia, are suitable for use and are well known in the art.

For example, simple binding assays can be used, in which a test antibody is incubated in the presence of a target protein or epitope (e.g., NKG2A or a portion thereof), unbound antibodies are washed off, and the presence of bound antibodies is assessed using, e.g., radiolabels, physical methods such as mass spectrometry, or direct or indirect fluorescent labels detected using, e.g., cytofluorometric analysis (e.g. FACScan). Such methods are well known to those of skill in the art. Any amount of binding above the amount seen with a control, non-specific antibody indicates that the antibody binds specifically to the target.

In such assays, the ability of the test antibody to bind to the target cell or human NKG2A can be compared with the ability of a (negative) control protein, e.g. an antibody raised against a structurally unrelated antigen, or a non-Ig peptide or protein, to bind to the same target. Antibodies or fragments that bind to the target cells or NKG2A using any suitable assay with 25%, 50%, 100%, 200%, 1000%, or higher increased affinity relative to the control protein, are said to "specifically bind to" or "specifically interact with" the target, and are preferred for use in the therapeutic methods described below. The ability of a test antibody to affect the binding of a (positive) control antibody against NKG2A, e.g. Z270, or derivatives thereof, may also be assessed.

The humanized anti-NKG2A antibodies may or may not bind human NKG2C, may or may not bind human NKG2E, or may or may not bind any of human NKG2C and E. In a particular embodiment, the monoclonal antibody or fragment does not bind to other human NKG2 receptors, specifically the activating receptors NKG2C or NKG2E. The NKG2C— and NKG2E-binding properties of the antibodies of the invention can be evaluated in similar assays as those described above, simply exchanging NKG2A for the molecule of interest.

In one aspect, the invention provides for humanized versions of non-human antibodies sharing biological characteristics and/or substantial sequence identity with Z270. One exemplary biological characteristic is the binding to the Z270 epitope, i.e., the region in the extracellular domain of NKG2A to which the Z270 antibody binds. To screen for antibodies that bind to the Z270 epitope, a routine cross-blocking assay, such as that described in Antibodies, A Laboratory Manual, Cold Spring Harbor Laboratory, Ed Harlow and David Lane (1988), can be performed.

In an exemplary cross-blocking or competition assay, Z270 (control) antibody and a test antibody are admixed (or pre-adsorbed) and applied to a sample containing NKG2A. In certain embodiments, one would pre-mix the control antibodies with varying amounts of the test antibody (e.g., 1:10 or 1:100) for a period of time prior to applying to the NKG2A-containing sample. In other embodiments, the control and varying amounts of test antibody can simply be admixed during exposure to the antigen/target sample. As long as one can distinguish bound from free antibodies (e.g., by using separation or washing techniques to eliminate unbound antibodies) and the control antibody from test antibody (e.g., by using species- or isotype-specific secondary antibodies, by specifically labeling the control antibody with a detectable label, or by using physical methods such as mass spectrometry to distinguish between different compounds) one will be able to determine if the test antibody reduces the binding of the control antibody to the antigen, indicating that the test antibody recognizes substantially the same epitope as the control. In this assay, the binding of the (labeled) control antibody in the presence of a completely irrelevant antibody is the control high value. The control low value is be obtained by incubating the labeled (positive) control antibody (Z270) with unlabeled control antibody, where competition would occur and reduce binding of the labeled antibody.

In a test assay, a significant reduction in labeled antibody reactivity in the presence of a test antibody is indicative of a test antibody that recognizes the same epitope, i.e., one that "cross-reacts" with the labeled control antibody. Any test antibody or compound that reduces the binding of the labeled control to the antigen/target by at least 50% or more preferably 70%, at any ratio of control:test antibody or compound between about 1:10 and about 1:100 is considered to be an antibody or compound that binds to substantially the same epitope or determinant as the control. Preferably, such test antibody or compound will reduce the binding of the control to the antigen/target by at least 90%. Nevertheless, any compound or antibody that reduces the binding of a control antibody or compound to any measurable extent can be used in the present invention.

Similar cross-blocking assays can also be used to evaluate whether a test (humanized) antibody affects the binding of the natural ligand for human NKG2A, HLA-E, to NKG2A, by exchanging Z270 for a suitable form of HLA-E. For example, to determine whether a humanized anti-NKG2A antibody preparation reduces or blocks CD94/NKG2A interactions with HLA-E, the following test can be performed: A cell line expressing CD94/NKG2A, such as Ba/F3-CD94/NKG2A, NKL or NK92, is incubated for 30 min on ice, with increasing concentrations of a test anti-NKG2A antibody. The cells are then incubated with PE-labeled HLA-E tetramers for 30 minutes on ice, washed again, and HLA-E tetramer binding analyzed on a flow cytometer (FACScalibur, Beckton Dickinson), by standard methods. In the absence of test antibodies, the HLA-E tetramer binds to the cells. In the presence of an antibody preparation that blocks CD94/NKG2A-binding to HLA-E, there is a reduced binding of HLA-E tetramers to the cells, and such mAbs are designated "blocking antibodies".

In some aspects of the invention, e.g., where it is not desired to kill NKG2A-expressing cells, the humanized antibodies of this invention preferably do not demonstrate substantial specific binding to Fc receptors. Such antibodies may comprise constant regions of various heavy chains that are known not to bind Fc receptors. One such example is an IgG4 constant region. Alternatively, antibody fragments that do not comprise constant regions, such as Fab or F(ab')2 fragments, can be used to avoid Fc receptor binding. Fc recepfor binding can be assessed according to methods known in the art, including for example testing binding of an antibody to Fc receptor protein in a BIACORE assay. Also, any other antibody type can be used in which the Fc portion is modified to minimize or eliminate binding to Fc receptors (see, e.g., WO03101485, the disclosure of which is herein incorporated by reference). Assays such as, e.g., cell based assays, to assess Fc receptor binding are well known in the art, and are described in, e.g., WO03101485.

Cytotoxicity Assays

If an anti-NKG2A antibody reduces or blocks CD94/NKG2A interactions with HLA-E, it may increase the cytotoxicity of CD94/NKG2A-restricted lymphocytes. This can be evaluated by a typical cytotoxicity assay, examples of which are described below.

The ability of an antibody to reduce CD94/NKG2A-mediated signaling can be tested in a standard 4-hour in vitro cytotoxicity assay using, e.g., NKL cells that express CD94/NKG2A, and target cells that express HLA-E. Such NKL cells do not efficiently kill targets that express HLA-E because CD94/NKG2A recognizes HLA-E, leading to initiation and propagation of inhibitory signaling that prevents lymphocyte-mediated cytolysis. Such an in vitro cytotoxicity assay can be carried out by standard methods that are well known in the art, as described for example in Coligan et al., eds., Current Protocols in Immunology, Greene Publishing Assoc. and Wiley Interscience, N.Y., (1992, 1993). The target cells are labeled with $^{51}Cr$ prior to addition of NKL cells, and then the killing is estimated as proportional to the release of $^{51}Cr$ from the cells to the medium, as a result of killing. The addition of an antibody that prevents CD94/NKG2A from binding to HLA-E results in prevention of the initiation and propagation of inhibitory signaling via CD94/NKG2A. Therefore, addition of such agents results in increases in lymphocyte-mediated killing of the target cells. This step thereby identifies agents that prevent CD94/NKG2A-induced negative signaling by, e.g., blocking ligand binding. In a particular $^{51}Cr$-release cytotoxicity assay, CD94/NKG2A-expressing NKL effector-cells can kill HLA-E-negative LCL 721.221 target cells, but less well HLA-E-expressing LCL 721.221-Cw3 control cells. In contrast, YTS effector-cells that lack CD94/NKG2A kill both cell-lines efficiently. Thus, NKL effector cells kill less efficiently HLA-E$^+$ LCL 721.221-Cw3 cells due to HLA-E-induced inhibitory signaling via CD94/NKG2A. When NKL cells are pre-incubated with blocking anti-CD94/NKG2A antibodies according to the present invention in such a $^{51}Cr$-release cytotoxicity assay, HLA-E-expressing LCL 721.221-Cw3 cells are more efficiently killed, in an antibody-concentration-dependent fashion.

The inhibitory or potentiating activity of an antibody of this invention can also be assessed in any of a number of other ways, e.g., by its effect on intracellular free calcium as described, e.g., in Sivori et al., J. Exp. Med. 1997; 186: 1129-1136, the disclosure of which is herein incorporated by reference. NK, T, or NKT cell activity can also be assessed using a cell based cytotoxicity assays, e.g., measuring chromium release or other parameter to assess the ability of the antibody to stimulate NK cells to kill target cells such as P815, K562 cells, or appropriate tumor cells as disclosed in Sivori et al., J. Exp. Med. 1997; 186:1129-1136; Vitale et al., J. Exp. Med. 1998; 187:2065-2072; Pessino et al. J. Exp. Med. 1998; 188:953-960; Neri et al. Clin. Diag. Lab. Immun. 2001; 8:1131-1135; Pende et al. J. Exp. Med. 1999; 190:1505-1516, the entire disclosures of each of which are herein incorporated by reference.

In one embodiment, an antibody preparation causes at least a 10% augmentation in the cytotoxicity of a CD94/NKG2A-restricted lymphocyte, preferably at least a 40% or 50% augmentation in NK cytotoxicity, or more preferably at least a 70% augmentation in NK cytotoxicity.

The activity of a cytotoxic lymphocyte can also be addressed using a cytokine-release assay, wherein NK cells are incubated with the antibody to stimulate the cytokine production of the NK cells (for example IFN-γ and TNF-α production). In an exemplary protocol, IFN-γ production from PBMC is assessed by cell surface and intracytoplasmic staining and analysis by flow cytometry after 4 days in culture. Briefly, Brefeldin A (Sigma Aldrich) is added at a final concentration of 5 μg/ml for the last 4 hours of culture. The cells are then incubated with anti-CD3 and anti-CD56 mAb prior to permeabilization (IntraPrep™; Beckman Coulter) and staining with PE-anti-IFN-γ or PE-IgG1 (Pharmingen). GM-CSF and IFN-γproduction from polyclonal activated NK cells are measured in supernatants using ELISA (GM-CSF: DuoSet Elisa, R&D Systems, Minneapolis, MN, IFN-: OptElA set, Pharmingen).

In a particular aspect, the invention provides antibodies that are more capable of, or more effective in, increasing the cytotoxicity of CD94/NKG2A-restricted lymphocytes, potentiating cytotoxic activity of a CD94/NKG2A-restricted lymphocyte, or reducing or inhibiting CD94/NKG2A-mediated signaling, than the original, non-humanized antibody and/or a chimeric version thereof. Such antibodies can be, for example, at least 2%, at least 5%, at least 10%, at least 15%, or at least 20% more capable or effective an original, non-humanized antibody or chimeric version thereof.

Recombinant Methods

The invention also provides isolated nucleic acids encoding the anti-NKG2A antibodies described herein, as well as vectors and host cells comprising such nucleic acids. Also provided for are methods of producing such anti-NKG2A antibodies using recombinant techniques such as, e.g., culturing suitable host cells comprising such nucleic acids or vectors so that the nucleic acid is expressed and the humanized antibody produced. Before culturfing, the host cell may, for example, be co-transfected with a vector comprising nucleic acids encoding a variable heavy domain and with a vector comprising nucleic acid encoding a variable light domain. Additionally, the antibody may be recovered and/or purified from the host cell culture using known techniques. Useful vectors, host cells, and techniques are further described below and in the Examples. Additionally, strategies for expressing humanized anti-NKG2A antibodies are outlined in FIGS. 4-6.

Generally, for recombinant production of the antibody, a nucleic acid encoding it is isolated and inserted into a replicable vector for further cloning (amplification of the DNA) or for expression, typically operably linked to one or more expression control elements. DNA encoding the monoclonal antibody is readily isolated and sequenced using conventional procedures (e.g., by using oligonucleotide probes that are capable of binding specifically to genes encoding the heavy and light chains of the antibody). Many vectors are known and available. The vector components generally include, but are not limited to, one or more of the following: a signal sequence, an origin of replication, one or more marker genes, an enhancer element, a promoter, and a transcription-termination sequence.

Signal Sequence Component

The anti-NKG2A antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. See, e.g., Example 2 for exemplary signal sequences for expression of humanized heavyand/or light chains of anti-NKG2A antibodies such as humanized Z270 antibodies.

For prokaryotic host cells that do not recognize and process the native anti-NKG2A antibody signal sequence, the signal sequence is substituted by a prokaryotic signal sequence selected, for example, from the group of the alkaline phosphatase, penicillinase, Ipp, or heat-stable enterotoxin II leaders. For yeast secretion the native signal sequence may be substituted by, e.g., the yeast invertase leader, alpha-factor leader (including *Saccharomyces* and *Kluyveromyces* alpha-factor leaders), acid-phosphatase leader, the *C. albicans* glucoamylase leader, or the signal described in WO 1990/13646. In mammalian cell expression, mammalian signal sequences as well as viral secretory leaders, for example, the herpes simplex gD signal, are available.

The DNA for such precursor region is ligated in reading frame to DNA encoding the anti-NKG2A antibody.

Origin of Replication Component

Both expression and cloning vectors contain a nucleic acid sequence that enable the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2p plasmid origin is suitable for yeast, and various viral origins (SV40, polyoma, adenovirus, VSV, EBV, or BPV) are useful for cloning vectors in mammalian cells. Generally, the origin of replication component is not needed for mammalian expression vectors (the SV40 origin may typically be used only because it contains the early promoter).

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the anti-NKG2A antibody-encoding nucleic acid, such as DHFR, thymidine kinase, metallothionein-I and -II, preferably primate metallothionein genes, aderosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding anti-NKG2A antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6-μm circular plasmid pKD1 can be used for transformation of Kluyveromyces yeasts. Alternatively, an expression system for large-scale production of recombinant calf chymosin was reported for K. lactis (Van den Berg, Bio/Technology, 8:135 (1990). Stable multi-copy expression vectors for secretion of mature recombinant human serum albumin by industrial strains of Kluyveromyces have also been disclosed. Fleer et al., Bio/Technolog, 9: 968-975 (1991).

Promoter Component

Expression and cloning vectors usually contain a promoter that is recognized by the host organism and is operably linked to the anti-NKG2A antibody-encoding nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-NKG2A antibody.

Various promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly-A tail to the 3' end of the coding sequence. All of these sequences are suitably inserted into eukaryotic expression vectors. Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP73657. Yeast enhancers also are advantageously used with yeast promoters.

Anti-NKG2A antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus (CMV), a retrovirus, hepatitis-B virus and most preferably Simian Virus 40 (SV40), heterologous mammalian promoters, e.g., the actin promoter or an immunoglobulin promoter, and heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature, 297:598-601 (1982) on expression of human .beta.-interferon cDNA in mouse cells under the control of a thymidine kinase promoter from herpes simplex virus. Alternatively, the rous sarcoma virus long-terminal repeat can be used as the promoter.

Enhancer Element Component

Transcription of a DNA encoding the anti-NKG2A antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early-promoter enhancer, the polyoma enhancer on the late side of the replication origin, and adenovirus enhancers. See also Yaniv, Nature, 297:17-18 (1982) on enhancing elements for activation of eukaryotic promoters. The enhancer may be spliced into the vector at a position 5' or 3' to the anti-NKG2A antibody-encoding sequence, but is preferably located at a site 5' from the promoter.

Transcription Termination Component

Expression vectors used in eukaryotic host cells (for example, yeast, fungi, insect, plant, animal, human, or nucleated cells from other multicellular organisms) will also contain sequences necessary for the termination of transcription and for stabilizing the mRNA. Such sequences are commonly available from the 5' end, occasionally 3' end, of untranslated regions of eukaryotic or viral DNAs or cDNAs. These regions contain nucleotide segments transcribed as polyadenylated fragments in the untranslated portion of the mRNA encoding anti-NKG2A antibody. One useful transcription termination component is the bovine growth hormone polyadenylation region. See WO 1994/11026 and the expression vector disclosed therein.

Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g. *B. licheniformis* 41 P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-NKG2A antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated anti-NKG2A antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g. the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney (HEK) line (293 or 293 cells subcloned for growth in suspension culture, Graham et al., J. Gen Virol., 36:59 (1977)); baby hamster kidney cells (BHK, ATCC CCL 10); Chinese hamster ovary cells/–DHFR (CHO, Urlaub et al., Proc. Natl. Acad. Sci. USA, 77:4216 (1980), including DG44 (Urlaub et al., Som. Cell and Mol. Gen., 12: 555-566 (1986)) and DP12 cell lines); mouse sertoli cells (TM4, Mather, Biol. Reprod., 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci., 383:44-68 (1982)); MRC 5 cells; FS4 cells; and a human hepatoma line (Hep G2).

Host cells are transformed with the above-described expression or cloning vectors for anti-NKG2A antibody production and cultured in conventional nutrient media modified as appropriate for inducing promoters, selecting transformants, or amplifying the genes encoding the desired sequences.

Culturing the Host Cells

The host cells used to produce the anti-NKG2A antibody of this invention may be cultured in a variety of media. Commercially available media such as Ham's F10 (Sigma), Minimal Essential Medium ((MEM), (Sigma), RPMI-1640 (Sigma), FreeStyle™ (Cibco) and Dulbecco's Modified Eagle's Medium ((DMEM), Sigma) are suitable for culturing the host cells. In addition, any of the media described, for example, in Ham et al., Meth. Enz. 58:44 (1979); Barnes et al., Anal. Biochem., 102:255 (1980); U.S. Pat. No. 4,767, 704; 4,657,866; 4,927,762; 4,560,655; or 5,122,469; WO 1990/03430; WO 1987/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Purification of Anti-NKG2A Antibody

When using recombinant techniques, the antibody can be produced intracellularly or in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology, 10: 163-167 (1992) describes a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an AMICON™ or MILLIPORE PELLICON™ ultrafiltration unit. A protease inhibitor such as phenylmethylsulphonyl fluoride (PMSF) may be included in any of the foregoing steps to inhibit proteolysis, and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human gamma1, gamma, or gamma4 heavy chains (Lindmark et al., J. Immunol. Meth., 62:1-13 (1983)). Protein G is recommended for all mouse isotypes and for human y3 (Guss et al., EMBO J., 5:15671575 (1986)). The matrix to which the affinity ligand is attached is most often agarose, but other matrices are available. Mechanically stable matrices such as controlled-pore glass or poly(styrenedivinyl)benzene allow for faster flow rates and shorter processing times than can be achieved with agarose. Where the antibody comprises a CH3 domain, the BAKERBOND ABX™ resin (J. T. Baker, Phillipsburg, N.J.) is useful for purification. Other techniques for protein purification such as fractionation on an ion-exchange column, ethanol precipitation, reverse-phase HPLC, chromatography on silica, chromatography on heparin SEPHAROSE™, chromatography on an anion- or cation-exchange resin (such as a polyaspartic acid column), chromatofocusing, SDS-PAGE, and ammonium-sulfate precipitation are also available depending on the antibody to be recovered.

An exemplary Protein A-based purification method for Z270 or humanized versions thereof is described in Example 6.

Pharmaceutical Formulations

In one embodiment, the present invention provides pharmaceutical composition comprising antibodies as described herein together with one or more carriers.

Accordingly, one object of the invention is to provide a pharmaceutical formulation comprising such an antibody which is present in a concentration from 1 mg/ml to 500 mg/ml, and wherein said formulation has a pH from 2.0 to 10.0. The formulation may further comprise a buffer system, preservative(s), tonicity agent(s), chelating agent(s), stabilizers and surfactants. In one embodiment, the pharmaceutical formulation is an aqueous formulation, i.e., formulation comprising water. Such formulation is typically a solution or a suspension. In a further embodiment, the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, whereto the physician or the patient adds solvents and/or diluents prior to use.

In another embodiment, the pharmaceutical formulation is a dried formulation (e.g. freeze-dried or spray-dried) ready for use without any prior dissolution.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

In a another embodiment, the pH of the formulation is in the range selected from the list consisting of from about 2.0 to about 10.0, about 3.0 to about 9.0, about 4.0 to about 8.5, about 5.0 to about 8.0, and about 5.5 to about 7.5.

In a further embodiment, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment, the formulation further comprises a pharmaceutically acceptable preservative. The preservative may be selected from, e.g., the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. The preservative may, e.g., be present in a concentration from 0.1 mg/ml to 20 mg/ml, from 0.1 mg/ml to 5 mg/ml, from 5 mg/ml to 10 mg/ml, or from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19$^{th}$ edition, 1995.

In a further embodiment, the formulation further comprises an isotonic agent. The isotonic agent may be, e.g., selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment, the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. The sugar or sugar alcohol concentration can, e.g., be between about 1 mg/ml and about 150 mg/ml. The isotonic agent can be present in a concentration from, e.g., 1 mg/ml to 50 mg/ml, from 1 mg/ml to 7 mg/ml, from 8 mg/ml to 24 mg/ml, or from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 19$^{th}$ edition, 1995.

In a further embodiment, the formulation also comprises a chelating agent. The chelating agent can, for example, be selected from salts of ethylenediaminetetraacetic acid (EDTA), citric acid, and aspartic acid, and mixtures thereof. The chelating agent may, for example, be present in a concentration from 0.1 mg/ml to 5 mg/ml, from 0.1 mg/ml to 2 mg/ml, or from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a stabilizer. The use of a stabilizer in pharmaceutical compositions is well-known to the skilled person. For convenience reference is made to Remington: *The Science and Practice of Pharmacy*, 19th edition, 1995. More particularly, compositions of the invention can be stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or a mixture thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L or D) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment, the formulation further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freezethawing or mechanical shearing.

In a further embodiment, the formulation further comprises a surfactant. The surfactant may, for example, be selected from a detergent, ethoxylated castor oil, polyglycolyzed glycerides, acetylated monoglycerides, sorbitan fatty acid esters, polyoxypropylenepolyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives—(e.g. sodium tauro-dihydrofusidate etc.), long-chain fatty acids and salts thereof C6-C12 (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, $N^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), non-ionic surfactants (eg. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 19$^{th}$ edition, 1995.

In a further embodiment, the formulation further comprises protease inhibitors such as EDTA (ethylenediamine tetraacetic acid) and benzamidineHCl, but other commercially available protease inhibitors may also be used. The use of a protease inhibitor is particular useful in pharmaceutical compositions comprising zymogens of proteases in order to inhibit autocatalysis.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing an antibody according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, subcutaneous, intramuscular, intraperitoneal, intravenous, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the antibody, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block copolymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, selfemulsifying, selfmicroemulsifying, cyclodextrins and derivatives thereof, and dendrimers.

Compositions of the current invention are useful in the formulation of solids, semisolids, powder and solutions for pulmonary administration of an antibody, using, for example a metered dose inhaler, dry powder inhaler and a nebulizer, all being devices well known to those skilled in the art.

Compositions of the current invention are also useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the antibody compound in the form of a nasal or pulmonal spray. As a still further option, the pharmaceutical compositions containing an antibody of the invention can also be adapted to transdermal administration, e.g. by needle-free injection or from a patch, optionally an iontophoretic patch, or transmucosal, e.g. buccal, administration.

The antibody can be administered via the pulmonary route in a vehicle, as a solution, suspension or dry powder using any of known types of devices suitable for pulmonary drug delivery. Examples of these comprise of, but are not limited to, the three general types of aerosol-generating for pulmonary drug delivery, and may include jet or ultrasonic nebulizers, metered-dose inhalers, or dry powder inhalers (Cf. Yu J, Chien YW. Pulmonary drug delivery: Physiologic and mechanistic aspects. Crit. Rev Ther Drug Carr Sys 14(2) (1997) 395-453).

Based on standardized testing methodology, the aerodynamic diameter ($d_a$) of a particle is defined as the geometric equivalent diameter of a reference standard spherical particle of unit density (1 g/cm$^3$). In the simplest case, for spherical particles, $d_a$ is related to a reference diameter (d) as a function of the square root of the density ratio as described by:

$$d_a = \sqrt{\frac{\rho}{\rho_a}} d$$

Modifications to this relationship occur for non-spherical particles (cf. Edwards D A, Ben-Jebria A, Langer R. Recent advances in pulmonary drug delivery using large, porous inhaled particles. J Appl Physiol 84(2) (1998) 379-385). The terms "MMAD" and "MMEAD" are well-described and known to the art (cf. Edwards D A, Ben-Jebria A, Langer R and represents a measure of the median value of an aerodynamic particle size distribution. Recent advances in pulmonary drug delivery using large, porous inhaled particles. J Appl Physiol 84(2) (1998) 379-385). Mass median aerodynamic diameter (MMAD) and mass median effective aerodynamic diameter (MMEAD) are used inter-changeably, are statistical parameters, and empirically describe the size of aerosol particles in relation to their potential to deposit in the lungs, independent of actual shape, size, or density (cf. Edwards D A, Ben-Jebria A, Langer R. Recent advances in pulmonary drug delivery using large, porous inhaled particles. J Appl Physiol 84(2) (1998) 379-385). MMAD is normally calculated from the measurement made with impactors, an instrument that measures the particle inertial behaviour in air.

In a further embodiment, the formulation could be aerosolized by any known aerosolisation technology, such as nebulisation, to achieve a MMAD of aerosol particles less than 10 μm, more preferably between 1-5 μm, and most preferably between 1-3 μm. The preferred particle size is based on the most effective size for delivery of drug to the deep lung, where protein is optimally absorbed (cf. Edwards D A, Ben-Jebria A, Langer A, Recent advances in pulmonary drug delivery using large, porous inhaled particles. J Appl Physiol 84(2) (1998) 379-385).

Deep lung deposition of the pulmonal formulations comprising the antibody may optional be further optimized by using modifications of the inhalation techniques, for example, but not limited to: slow inhalation flow (eg. 30 L/min), breath holding and timing of actuation.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as antrhacene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention the pharmaceutical formulation comprising the antibody is stable for more than 6 weeks of usage and for more than 3 years of storage.

In another embodiment of the invention the pharmaceutical formulation comprising the antibody is stable for more than 4 weeks of usage and for more than 3 years of storage.

In a further embodiment of the invention the pharmaceutical formulation comprising the antibody is stable for more than 4 weeks of usage and for more than two years of storage.

In an even further embodiment of the invention the pharmaceutical formulation comprising the antibody is stable for more than 2 weeks of usage and for more than two years of storage.

Suitable antibody formulations can also be determined by examining experiences with other already developed therapeutic monoclonal antibodies. Several monoclonal antibodies have been shown to be efficient in clinical situations, such as Rituxan (Rituximab), Herceptin (Trastuzumab) Xolair (Omalizumab), Bexxar (Tositumomab), Campath (Alemtuzumab), Zevalin, Oncolym and similar formulations may be used with the antibodies of this invention. For example, a monoclonal antibody can be supplied at a concentration of 10 mg/mL in either 100 mg (10 mL) or 500 mg (50 mL) single-use vials, formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. In another embodiment, the antibody is supplied in a formulation comprising about 20 mM Na-Citrate, about 150 mM NaCl, at pH of about 6.0.

Therapeutic Applications

Methods of treating a patient using an anti-NKG2A antibody as described herein are also provided for. In one embodiment, the invention provides for the use of an antibody as described herein in the preparation of a pharmaceutical composition for administration to a human patient. Typically, the patient suffers from, or is at risk for, cancer, a viral disease, an inflammatory disorder, or an autoimmune disorder. Alternatively, the antibody of the invention is used to improve bone marrow transplantation in a patient.

For example, in one aspect, the invention provides a method of potentiating the activity of CD94/NKG2A-restricted lymphocytes in a patient in need thereof, comprising the step of administering a human or humanized anti-NKG2A antibody to said patient, which antibody reduces or prevents HLA-E-mediated activation of the CD94/NKG2A receptor. In one embodiment, the method directed at increasing the activity of such lymphocytes in patients having a disease in which increased NK, T, and/or NKT cell activity is beneficial, which involves, affects or is caused by cells susceptible to lysis by NK, T, or NKT cells, or which is caused or characterized by insufficient NK, T, or NKT cell activity, such as a cancer, an infectious disease or an immune disorder.

More specifically, the methods and compositions of the present invention are utilized for the treatment of a variety of cancers and other proliferative diseases including, but not limited to: carcinoma, including that of the bladder, breast, colon, kidney, liver, lung, ovary, prostate, pancreas, stomach, cervix, thyroid and skin, including squamous cell carcinoma; hematopoietic tumors of lymphoid lineage, including leukemia, acute lymphocytic leukemia, chronic lymphocytic leukemia, acute lymphoblastic leukemia, B-cell lymphoma, T-cell lymphoma, Hodgkin's lymphoma, non-Hodgkin's lymphoma, hairy cell lymphoma and Burkitt's lymphoma, and multiple myeloma; hematopoietic tumors of myeloid lineage, including acute and chronic myelogenous leukemias, promyelocytic leukemia, and myelodysplastic syndrome; tumors of mesenchymal origin, including fibrosarcoma and rhabdomyosarcoma; other tumors, including melanoma, seminoma, terato-carcinoma, neuroblastoma and glioma; tumors of the central and peripheral nervous system, including astrocytoma, neuroblastoma, glioma, and schwannomas; tumors of mesenchymal including fibrosarcoma, rhabdomyosarcoma, and osteosarcoma; and other tumors, including melanoma, xeroderma pigmentosum, keratoacanthoma, seminoma, thyroid follicular cancer and teratocarcinoma.

Particular disorders that can be treated according to the invention include hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; Sezary syndrome (SS); adult T-cell leukemia lymphoma (ATLL); T-NHL hepatosplenic lymphoma; peripheral/post-thymic T cell lymphoma (pleomorphic and immunoblastic subtypes); angio immunoblastic T-cell lymphoma; angiocentric (nasal) T-cell lymphoma; anaplastic (Ki 1+) large cell lymphoma; intestinal T-cell lymphoma; T-lymphoblastic; lymphoma/leukaemia (T-Lbly/T-ALL), multiple myeloma. Other proliferative disorders can also be treated according to the invention, including for example hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty.

In a particular aspect, antibodies of the invention are used to treat NK-type lymphoproliferative disease of granular lymphocytes; alternatively called NK-LGL), referring to a class of proliferative disorders that is caused by the clonal expansion of NK cells or NK-like cells, i.e., large granular lymphocytes showing a characteristic combination of surface antigen expression (e.g., CD3−, CD56+, CD16+, etc.; see, e.g., Loughran (1993) Blood 82:1). The cell proliferation underlying these disorders can have variable effects, ranging from the mild symptoms seen in some patients to the aggressive, often-fatal form of the disease called NK-LDGL leukemia. Symptoms of this class of disorders can include fever, mild neutropenia, thrombocytopenia, anemia, lymphocytosis, splenomegaly, hepatomegaly, lymphadenopathy, marrow infiltration, and others (see, e.g., Zambello et al. (2003) Blood 102:1797; Loughran (1993) Blood 82:1; Epling-Burnette et al. (2004) Blood-2003-02-400).

The CD94/NKG2A antibody based treatment can also be used to treat or prevent infectious diseases, including preferably any infections caused by infection by viruses, bacteria, protozoa, molds or fungi. Such viral infectious organisms include, but are not limited to, hepatitis type A, hepatitis type B, hepatitis type C, influenza, varicella, adenovirus, herpes simplex type I (HSV-1), herpes simplex type 2 (HSV-2), rinderpest, rhinovirus, echovirus, rotavirus, respiratory syncytial virus, papilloma virus, cytomegalovirus, echinovirus, arbovirus, huntavirus, coxsackie virus, mumps virus, measles virus, rubella virus, polio virus and human immunodeficiency virus type I or type 2 (HIV-1, HIV-2). Bacteria constitute another preferred class of infectious organisms including but are not limited to the following: *Staphylococcus; Streptococcus*, including *S. pyogenes*; Enterococci; *Bacillus*, including *Bacillus anthracis*, and *Lactobacillus; Listeria; Corynebacterium diphtheriae*; Gardnerella including *G. vaginalis; Nocardia; Streptomyces; Thermoactinomyces vulgaris; Treponerna; Camplyobacter, Pseudomonas* including *P. aeruginosa; Legionella; Neisseria* including *N. gonorrhoeae* and *N. meningitides; Flavobacterium* including *F. meningosepticum* and *F. odoraturn; Brucella; Bordetella* including *B. pertussis* and *B. bronchiseptica; Escherichia* including *E. coli, Klebsiella; Enterobacter, Serratia* including *S. marcescens* and *S. liquefaciens; Edwardsiella; Proteus* including *P. mirabilis* and *P. vulgaris; Streptobacillus; Rickettsiaceae* including *R. fickettsfi, Chlamydia* including *C. psittaci* and *C. trachornatis; Mycobacterium* including *M tuberculosis, M intracellulare, M folluiturn, M laprae, M avium, M bovis, M africanum, M kansasii, M intracellulare*, and *M lepraernurium*; and *Nocardia*. Protozoa may include but are not limited to, leishmania, kokzidioa, and trypanosoma. Parasites include but are not limited to, chlamydia and rickettsia. A complete list of infectious diseases can be found on the website of the National Center for Infectious Disease (NCID) at the Center for Disease Control (CDC) (World-Wide Web (www) address cdc.gov/ncidod/diseases/), which list is incorporated herein by reference. All of these diseases are candidates for treatment using the inhibitory anti-CD94/NKG2A antibodies of the invention.

In an alternative aspect, the anti-NKG2A antibodies are used to target and kill NKG2A-expressing cells in, e.g., a patient suffering from a cancer characterized by CD94/NKG2A expression on cancerous cells, for example an NK-lymphoma. In one embodiment, the humanized antibody is administered in the form of an immunoconjugate comprising the humanized antibody and a cytotoxic agent.

In alternative aspect, the anti-NKG2A antibodies are used to treat or prevent an autoimmune or inflammatory disorder. Exemplary autoimmune disorders treatable using the present methods include, inter alia, hemolytic anemia, pernicious anemia, polyarteritis nodosa, systemic lupus erythematosus, Wegener's granulomatosis, autoimmune hepatitis, Behcet's disease, Crohn's disease, primary bilary cirrhosis, scleroderma, ulcerative colitis, Sjogren's syndrome, Type 1 diabetes mellitus, uveitis, Graves' disease, Alzheimer' s disease, thyroiditis, myocarditis, rheumatic fever, scleroderma, ankylosing spondylitis, rheumatoid arthritis, glomerulonephritis, sarcoidosis, dermatomyositis, myasthenia gravis, polymyositis, Guillain-Barré syndrome, multiple sclerosis, alopecia areata, pemphigus/pemphigoid, Bullous pemphigoid, Hashimoto's thyroiditis, psoriasis, and vitiligo.

Examples of inflammatory disorders that can be treated by these methods include, but not limited to, adrenalitis, alveolitis, angiocholecystitis, appendicitis, balanitis, blepharitis, bronchitis, bursitis, carditis, cellulitis, cervicitis, cholecystitis, chorditis, cochlitis, colitis, conjunctivitis, cystitis, dermatitis, diverticulitis, encephalitis, endocarditis, esophagitis, eustachitis, fibrositis, folliculitis, gastritis, gastroenteritis, gingivitis, glossitis, hepatosplenitis, keratitis, labyrinthitis, laryngitis, lymphangitis, mastitis, media otitis, meningitis, metritis, mucitis, myocarditis, myositis, myringitis, nephritis, neuritis, orchitis, osteochondritis, otitis, pericarditis, peritendonitis, peritonitis, pharyngitis, phlebitis, poliomyelitis, prostatitis, pulpitis, retinitis, rhinitis, salpingitis, scleritis, selerochoroiditis, scrotitis, sinusitis, spondylitis, steatitis, stornatitis, synovitis, syringitis, tendonitis, tonsillitis, urethritis, and vaginitis.

It has also been shown that alloreactive NK cell killing of dendritic cells improved engraftment of hematopoietic cells in a bone marrow transplant (L. Ruggeri et al., Science, 2002, 295:2097-2 100). Thus, in another embodiment, the invention provides a method of improving the engraftment of hematopoietic cells in a patient comprising the step administering to said patient a composition of this invention comprising an activating antibody. Improvement in grafting is manifest by any one of reduced incidience or severity of graft versus host disease, prolonged survival of the graft, or a reduction in or elimination of the symptoms of the disease being treated by the graft (e.g., a hematopoietic cancer). This method is preferably used in the treatment of leukemia.

Combinations

A number of therapeutic agents are available for the treatment of cancers. The antibody compositions and methods of the present invention may thus also be combined with any other methods generally employed in the treatment of the particular disease, particularly a tumor, cancer disease, or other disease or disorder that the patient exhibits. So long as a particular therapeutic approach is not known to be detrimental to the patient's condition in itself, and does not significantly counteract the anti-CD94/NKG2A antibody-based treatment, its combination with the present invention is contemplated.

In connection with solid tumor treatment, the present invention may be used in combination with classical approaches, such as surgery, radiotherapy, chemotherapy, and the like. The invention therefore provides combined therapies in which anti-CD94/NKG2A antibodies according to the invention are used simultaneously with, before, or after surgery or radiation treatment; or are administered to patients with, before, or after administration of another anti-cancer agent. One would ensure that the surgery, radiotherapy, or anti-cancer agent in combination with the active agent in the composition of this invention exert an advantageously combined effect on the cancer.

Exemplary anti-cancer agents include chemotherapeutic agents, hormonal agents, anti-angiogenic agents, anti-metastatic agents, anti-cancer antibodies (e.g., Rituximab), antibodies against inhibitory KIR-molecules, growth-factor inhibitors, apoptosis-promoting compounds, cytokines and other immunomodulatory agents, tumor-targeting agents conjugated to toxins or radionuclides, compounds that interfere with DNA replication, mitosis and chromosomal segregation, and agents that disrupt the synthesis and fidelity of polynucleotide precursors.

For autoimmune or inflammatory disorders, any other compound known to be effective for one or more types of autoimmune or inflammatory disorders, or any symptom or feature of autoimmune or inflammatory disorders, including inter alia, immunosuppressants, e.g., azathioprine (e.g., Imuran), chlorambucil (e.g., Leukeran), cyclophosphamide (e.g., Cytoxan), cyclosporine (e.g., Sandimmune, Neoral), methotrexate (e.g., Rheumatrex), corticosteroids, prednisone (e.g., Deltasone, Meticorten), Etanercept (e.g., Enbrel), infliximab (e.g., Remicade), inhibitors of TNF, FK-506, raparnycin, mycophenolate mofetil, leflunomide, anti-lymphocyte globulin, deoxyspergualin or OKT.

Preferred examples of immunomodulatory compounds include cytokines. Other examples include compounds that have an effect, preferably an effect of activation or potentiation NK cell activity, or of inducing or supporting the proliferation of NK cells. Other compounds for administration before, simultaneously with, or after compositions comprising the agents of the invention are adjunct compounds (e.g., anti-emetics and analgesic agents) and antiviral agents.

As will be understood by those of ordinary skill in the art, the appropriate doses of anti-cancer agents will approximate those already employed in clinical therapies wherein the anti-cancer agents are administered alone or in combination with other agents. Variation in dosage will likely occur depending on the condition being treated. The physician administering treatment will be able to determine the appropriate dose for the individual subject.

Articles of Manufacture

In another embodiment of the invention, an article of manufacture containing materials useful for the treatment of the disorders described above is provided. For example, the article of manufacture can comprise a container containing an antibody as described herein together with instructions directing a user to treat a disorder such as a cancer or a viral disease in a mammal with the antibody in an effective amount. In a preferred embodiment, the mammal is a human. The article of manufacture typically comprises a container and a label or package insert on or associated with the container. Suitable containers include, for example, bottles, vials, syringes, etc. The containers may be formed from a variety of materials such as glass or plastic. The container holds a composition that is effective for treating the condition and may have a sterile access port (for example, the container may be an intravenous solution bag or a vial having a stopper pierceable by a hypodermic injection needle). At least one active agent in the composition is the humanized anti-NKG2A antibody herein, or an antibody derivative (e.g., an immunoconjugate) comprising such a humanized antibody. The label or package insert indicates that the composition is used for treating the condition of choice, such as cancer or a viral disease.

Moreover, the article of manufacture may comprise (a) a first container with a composition contained therein, wherein the composition comprises the antibody described herein, and (b) a second container with a composition contained therein, wherein the composition comprises a therapeutic agent other than the first antibody. The article of manufacture in this embodiment of the invention may further comprise a package insert indicating that the first and second compositions can be used in combination to treat a cancer or viral disease. Such therapeutic agent may be any of the adjunct therapies described in the preceding section (e.g., a chemotherapeutic agent, an anti-angiogenic agent, an anti-hormonal compound, a cardioprotectant, and/or a regulator of immune function in a mammal, including a cytokine). Alternatively, or additionally, the article of manufacture may further comprise a second (or third) container comprising a pharmaceutically acceptable buffer, such as bacteriostatic water for injection (SWFI), phosphate-buffered saline, Ringer's solution and dextrose solution. It may further include other materials desirable from a commercial and user standpoint, including other buffers, diluents, filters, needles, and syringes.

Administration

As described above, several monoclonal antibodies have been shown to be efficient in clinical situations (such as, e.g., Rituxan (Rituximab) and others), and similar administration regimens (i.e., doses and/or administration protocols) may be used with the antibodies of this invention. Schedules and dosages for administration can be determined in accordance with known methods for these products, for example using the manufacturers' instructions. For example, an antibody preparation can be supplied at a concentration of 10 mg/mL in either 100 mg (10 mL) or 500 mg (50 mL) single-use vials. An exemplary suitable dosage range for an antibody of the invention may between about 10 mg/m$^2$ and 500 mg/m$^2$. Quantities and schedule of injection of anti-NKG2A antibodies that, e.g., saturate cells for 24 hours, 48 hours, 72 hours or a week or a month can be determined considering the affinity of the antibody and its pharmacokinetic parameters. However, it will be appreciated that these schedules are exemplary and that optimal schedule and regimen and the tolerability of the antibodies must be determined in clinical trials.

Non-Therapeutic Applications

The antibodies (e.g. the humanized anti-NKG2A antibodies) of the invention also have non-therapeutic applications.

For example, the antibodies may be used as affinity-purification agents. In this process, the antibodies are immobilized on a solid phase such as a SEPHADEX™ resin or filter paper, using methods well known in the art. The immobilized antibody is contacted with a sample containing the NKG2A protein (or fragment thereof) to be purified, and thereafter the support is washed with a suitable solvent that will remove substantially all the material in the sample except the NKG2A protein, which is bound to the immobilized antibody. Finally, the support is washed with another suitable solvent, such as glycine buffer, pH 5.0, that will release the NKG2A protein from the antibody.

Anti-NKG2A antibodies may also be useful in diagnostic assays for NKG2A protein, e.g. detecting its expression in specific cells, tissues, or serum.

For diagnostic applications, the antibody typically will be labeled with a detectable moiety. Numerous labels are available that can be generally grouped into the following categories:

(a) Radioisotopes, such as $^{35}$S, $^{14}$C, $^{125}$I, $^{3}$H, and $^{131}$I. The antibody can be labeled with the radioisotope using the techniques described in Current Protocols in Immunology, Volumes 1 and 2, Coligen et al., Ed. Wiley-Interscience, New York, N.Y., Pubs. (1991), for example, and radioactivity can be measured using scintillation counting.

(b) Fluorescent labels such as rare-earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, .beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al, "Methods for the Preparation of Enzyme-Antibody Conjugates for use in Enzyme Immunoassay," in Methods in Enzym. (Ed., J. Langone & H. Van Vunakis), Academic Press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-nitrophenyl phosphate as chromogenic substrate; and (iii) beta-D-galactosidase (beta-D-Gal) with a chromogenic substrate (e.g., pnitrophenyl-beta-D-galactosidase) or fluorogenic substrate 4-methylumbelliferyl-p-betagalactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin, and any of the three broad categories of labels mentioned above can be conjugated with avidin, or vice versa. Biotin binds selectively to avidin, and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the anti-NKG2A antibody need not be labeled, and the presence thereof can be detected using a labeled secondary antibody that binds to the NKG2A antibody.

The antibodies of the present invention may be employed in any known assay method, such as competitive-binding assays, direct and indirect sandwich assays, and immunoprecipitation assays. Zola, Monoclonal Antibodies: A Manual of Techniques, pp. 147-158 (CRC Press, Inc. 1987).

For immunohistochemistry, the tumor sample may be fresh or frozen or may be embedded in paraffin and fixed with a preservative such as formalin, for example.

The antibodies may also be used for in vivo diagnostic assays. Generally, the antibody is labeled with a radionuclide or a non-radioactive indicator detectable by, e.g., nuclear magnetic resonance, or other means known in the art. Preferably, the label is a radiolabel, such as, e.g., $^{125}$I, $^{131}$I, $^{67}$Cu, $^{99m}$TC, or $^{111}$In. The labeled antibody is administered to a host, preferably via the bloodstream, and the presence and location of the labeled antibody in the host is assayed. This imaging technique is suitably used in the detection, staging and treatment of neoplasms. The radioisotope is conjugated to the protein by any means, including metal-chelating compounds or lactoperoxidase, or iodogen techniques for iodination.

As a matter of convenience, the antibodies of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor that provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents that substantially optimize the sensitivity of the assay. Particularly, the reagents may be provided as dry powders, usually lyophilized, including excipients that on dissolution will provide a reagent solution having the appropriate concentration.

Deposits

The Z270 hybridoma was deposited on Dec. 22, 2005 at the Collection Nationale de Culture de Microorganismes, Institute Pasteur, 25, Rue du Docteur Roux, F-75725 Paris, France, under accession number 1-3549.

EXAMPLES

Further details of the invention are illustrated by the following non-limiting Examples.

Example 1

Selection of Parent humZ270VL and humZ270VH Sequences

This Example describes the selection of parent humZ270VL and humZ270VH sequences as well as optional back mutations for variant h270VL and humZ270VH sequences.

As described in Example 2, the Z270 hybridoma was cloned, and the Z270 VH and VL chain sequences of the corresponding antibody from were determined to be:

Z270VL:
DIQMTQSPASLSASVGETVTITCRASENIYSYLAWYQQKQGKSPQFLVYNAKTLAEGVPSRF SGSGSGTQFSLKINSLQPEDFGSYYCQHHYGTPRTFGGGTKLEIK (SEQ ID NO:1), with an optional arginine (R) residue at Kabat position 108.

Z270VH:
QVQLQQPGAELVRPGASVKLSCKASGYTFTSYWMNWVKQRPEQGLQWIGRIDPYDSETH YSQKFKDKAILTVDKSSSTAYMRLSSLTSEDSAVYYCARGGYDFDVGTLYWFFDVWGAGTT VTVS (SEQ ID NO:2), with an optional C-terminal serine (S) residue.

A second light chain, Z270VL-NB, was also identified. However, this was a common myeloma light chain.

Z270VL-NB:
NIVMTQSPKSMSMSVGERVTLTCKASENWTYVSWYQQKPEQSPKLLIYGASN RYTGVPDRFTGSGSATDFTLTISSVQAEDLADYHCGQGYSYPYTFGGGTKLEIKRA (SEQ ID NO:3), with an optional arginine (R) residue at Kabat position 108, and an optional alanine (A) residue at Kabat position 109.

From an analysis of the murine Z270 sequences, the CDRs according to Kabats definitions were determined as:

```
CDR-L1:
            (residues 24-34 of SEQ ID NO: 1)
RASENIYSYLA

CDR-L2:
            (residues 50-56 of SEQ ID NO: 1)
NAKTLAE

CDR-L3:
            (residues 89-97 of SEQ ID NO: 1)
QHHYGTPRT

CDR-H1:
            (residues 31-35 of SEQ ID NO: 2)
SYWMN

CDR-H2:
            (residues 50-66 of SEQ ID NO: 2)
RIDPYDSETHYSQKFKD

CDR-H3:
            (residues 95-102 of SEQ ID NO: 2)
GGYDFDVGTLYWFFDV.
```

A 3D protein structure model was built using MOE (molecular Operating Environment; available at www-.chemcomp.com) with structural templates from the Protein Database Bank (PDB): 1OPG and 1XF4. The PDB is described in Berman et al. (Nucl Acids Res 2000; 28:235-242), and is available at www.rcsb.org/pdb. Based on a statistical analysis of 201 antibody-antigen complexes in the PDB database the most probable residues in the paratope were determined to be:

Z270VL: residues 24-34, 49-56, 89-97 of SEQ ID NO:1
Z270VH: residues 23-35, 49-58, 93-102 of SEQ ID NO:2.

Using MOE, residues interacting (hydrophobic, hydrogen binding, or charge) with the paratope were identified and the combined set of residues (paratope+interacting residues) were taken as the mask of Z270.

Searching the germline V databases (V-base; available at vbase.mrc-cpe.cam.ac.uk/) with the Z270VL and Z270VH returned the following potential framework templates (E-value given in parenthesis):

Heavy chain: VH1_46 (2e-036), VH1_f (2e-035), VH1_02 (3e-035), VH1_18 (4e-035), VH1_03 (6e-035); and Light chain: VKI_O2 (1e-039), VKI_O12 (1e-039), VKI_L12 (9e-038), VKI_L8 (9e-038), VKI_A20 (9e-038).

Searching the germline databases with the mask returned the following potential framework templates (E-value given in parenthesis):

Heavy chain: VH5_a (4e-013), VH5_51 (3e-011), VH1 f (1e-010), VH1_18 (2e-010), VH1_46 (4e-010): and Light chain: VKI_L9 (2e-012), VKI_O2 (3e-012), VKI_O12 (3e-012), VKI_L24 (2e-011), VKI_A20 (2e-011)

After manual inspections of the alignments and the hits, VH1_18 and VKI_O2 were selected as the human scaffolds. JH6 and JK4 were chosen as germline J-segments.

Humanization was now designed with the following rules:
Residues outside the mask are taken as human.
Residues inside the mask and inside the Kabat CDR are taken as murine.
Residues inside the mask and outside the Kabat CDR with mouse/germline consensus are taken as the consensus sequence.
Residues inside the mask and outside the Kabat CDR with mouse/germline difference are subject to potential back mutations.

The analysis is illustrated in FIG. 1 for Z270VL and Z270VH, where mask residues are those shaded in the Kabat scheme; CDR residues are shown in bold in the Kabat scheme; and mouse/germline differences are shaded in the VKI_02/JK4 and VH1_18/JH6 sequences. Z270VL and humZ270VL1, and humZ270VL1 cons may optionally comprise an arginine (R) residue at Kabat position 108.

The resulting sequences, humZ270VL1 and humZ270VH1, are given with the potential back mutation residues as human.

The CDRs of a humanized Z270 antibody according to the Kabat definitions are shown in FIG. 2. Of the humZ270 CDRs, only the CDR-H2 sequence was different than that of the corresponding murine CDR, differing in 4 positions. However, in effect, this meant that Kabat CDR-H2 residues 60-65 were identical to the human acceptor sequence, providing for a more human molecule and a lesser risk for immunogenicity. In FIG. 2, the differences are indicated in bold text.

Example 2

Cloning of Z270 IgG1 VH and VL regions

This Example describes the cloning and sequencing of murine Z270 VH and VL regions.

Z270 Hybridoma Cell Culture for Total RNA Extraction. Z270 hybridoma was cultured in RPMI 1640 (Hyclone Cat# SH30011.04) plus 10% FCS (Biochrom Cat#S0115). $5 \times 10^6$ to $1 \times 10^7$ cells were harvested for total RNA extraction.

Z270 Hybridoma Cell Culture of Antibody Production. One week batch culture strategy was adopted for the production of the Z270 mAb. The culture medium was RPMI 1640 with 10% FCS. The supernatant was harvested every 7 days. The starting cell density in the culture chamber of CL-1000 flask (INTEGRA Biosciences, Item No. 90005, Lot No. 08541150) was be $2 \times 10^6$ cells/ml. During the culture, the cell density and viability was checked regularly. After 3 days culture in CL-1000 flask, the density was above $1 \times 10^7$ and the viability was about 85%. In the next 4 days the cell density varied between $1.5-2.5 \times 10^7$ cells/ml and the viability decreased gradually to 60-70%. At the $7^{th}$ day the supernatant was collected and reducing SDS-PAGE was used to estimate the antibody concentration with a quantification control (A-TNP 20050118 2 mg/ml).

Z270 Total RNA Extraction. This was done using TRIZOL reagent Invitrogen, Cat. No. 15596-026, according to the manufacturer's instructions.

5'-RACE (Rapid Amplification of cDNA Ends). A protocol was adapted from the manufacturer's instructions for use of SMART™ RACE cDNA Amplification Kit product by Clontech, Catalog no. 634914, with the following design of Gene-Specific Primers (GSPs):

GSP1 for amplification of IgG1 heavy chain variable region
RacePrimerheavy: 5'-GCCAGTGGATAGACAGATGG-3' (SEQ ID NO:12)

GSP2: for amplification of IgG1 Kappa chain variable region
RacePrimerkappa: 5'-GATGGATACAGTTGGT-GCAGC-3' (SEQ ID NO:13).

After first-strand cDNA synthesis, RACE, and analysis of the resulting samples on a 1.5% agarose gel, the RACE DNA band was cut out and purified with Gel purification kit (QIAGEN QIAquick Cat#28706) then cloned into pMD-19 using DNA Ligation Kit (Cat#D6022 from TAKARA) Ver. 2.0 by TA cloning (FIG. 3A). The positive clones were sent out for DNA sequencing.

Several clones of light chain and heavy chain were sequenced with identical sequence as shown in FIG. 4A-D (with bold text indicating signal peptide sequences):
Z270 VL cDNA: (SEQ ID NO:14)
Z270 VL protein (SEQ ID NO:15)
Z270 VH cDNA (SEQ ID NO:16)
Z270 VH protein (SEQ ID NO:17).

Example 3

Cloning of Murine IgG1 Light Chain and Heavy Chain into pJSV002

Figure 3B:
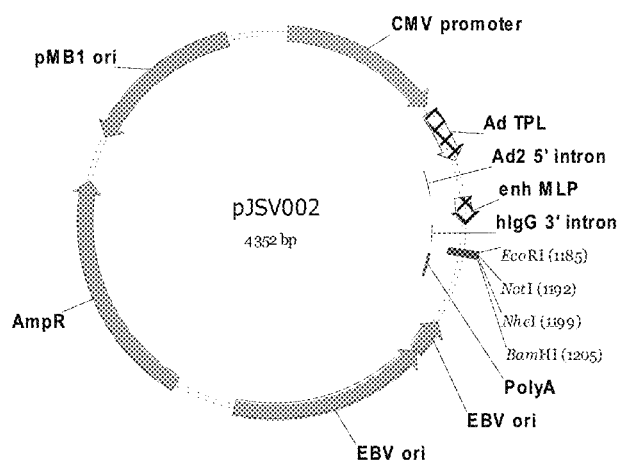

In order to test antibody affinity and to use it for positive control, Z270 antibody light chain and heavy chain is inserted into pJSV002 as murine antibody IgG1. pJSV002 is a transient expression vector that can be used in combination with HEK293 6E cells for Z270 transient expression (FIG. 3B).

Figure 3C:
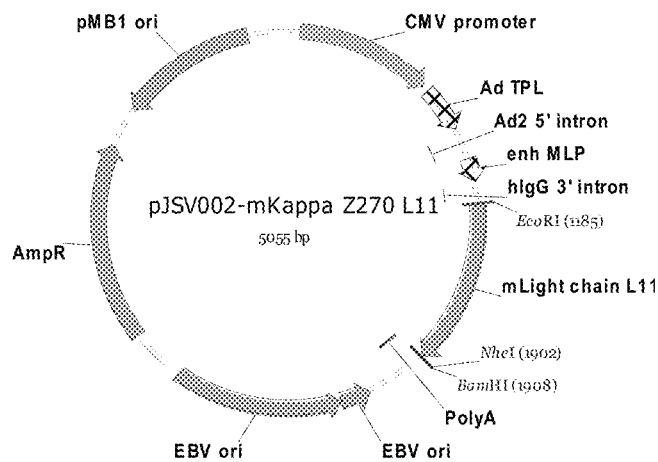

Z270 VL and IgG1 constant region are cloned into EcoRI and Nhe I sites of pJSV002. The resulted plasmid is as shown in FIG. 3C. The inserted sequence with EcoRI and Nhe I (uppercase letters) at both ends is shown in FIG. 4E (SEQ ID NO:18).

Figure 3D:
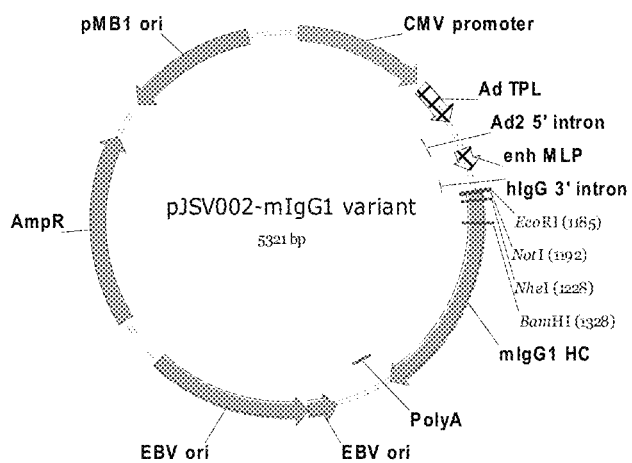
Figure 3E:
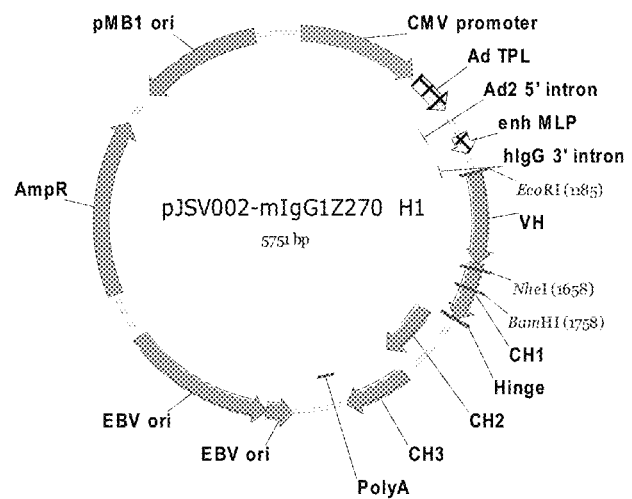

H1 variable region and IgG1 constant region is cloned into EcoRI and Nhe I sites of pJSV002-mIgG1-variant (FIG. 3D). The pJSV002-mIgG1-variant contains murine IgG1 heavy chain constant region (FIG. 3E). The inserted sequence is between EcoRI and Nhe I (gctagc) sites, with restriction sites and murine IgG1 constant region indicated in lowercase letters, is shown in FIG. 4F (SEQ ID NO:19).

Example 4

Plasmid Constructs for Chimeric Z270 Antibody

In order to test antibody affinity and to use it as positive control, murine Z270 antibody light chain and heavy chain are inserted into pJSV002 as human chimeric antibody IgG4 S241 P. The antibody contains murine variable region and human IgG4 constant region with an S241 P mutation in the heavy chain.

Figure 3F:
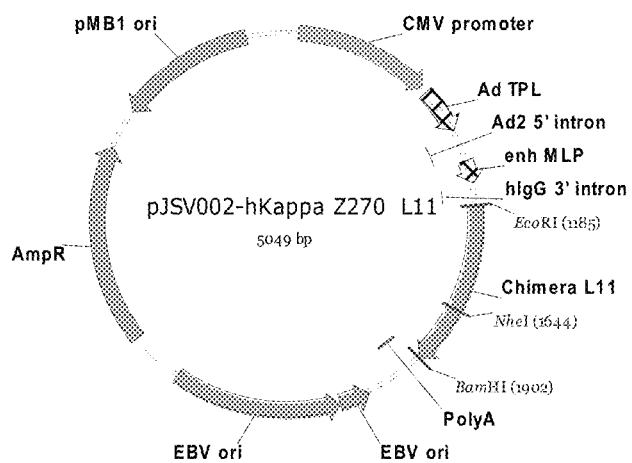

For expression of chimeric Z270 antibody (chimZ270), Z270VL sequence and human light chain (kappa) constant region is inserted into EcoR I and BamH I sites of pJSV002 (FIG. 3F). The sequence shown in FIG. 4G is used, where uppercase letters indicate restriction sites (SEQ ID NO:20).

Figure 3G:
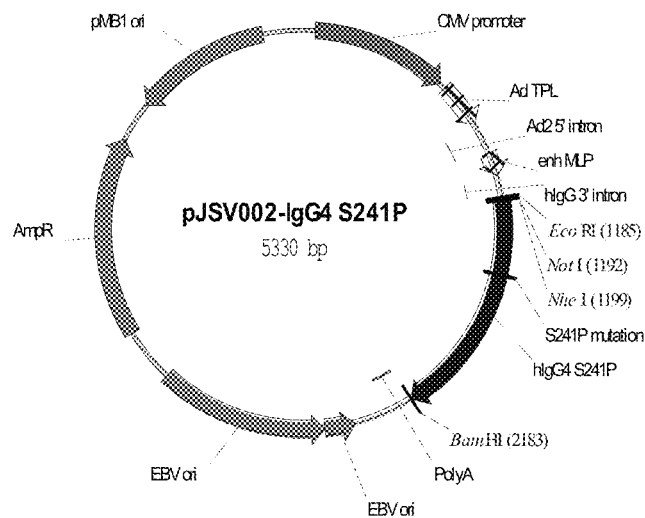
Figure 3H:
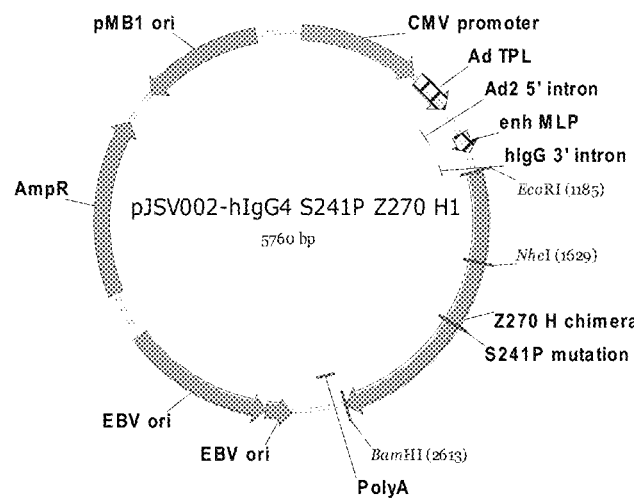

Z270 VH and human heavy chain constant region is inserted into EcoR I and Nhe I sites of pJSV002-IgG4-5241P (FIGS. 3G and 3H). The sequence shown in FIG. 4H is used, with the actual inserted sequence being between Eco RI and Nhe I (gctagc) sites, where upper-case letters indicate restriction sites (SEQ ID NO:21).

Example 5

Expression of Humanized Z270

According to the Z270 humanization strategy described in Example 1, Z270 light chain CDRs are grafted into the VKI_02/JK4 template to prepare humZ270VL1. The sequence shown in FIG. 4I results from synthesizing the sequence between EcoRI and KasI sites and inserting the it into pJSV002-hKappaC (with human Kappa constant region in pJSV002), with CDR-encoding sequences in uppercase letters and restriction sites in bold text (SEQ ID NO:22).

For humanization of the heavy chain, Z270 heavy chain CDRs (optionally with optimized CDR-H2 are grafted into the VH1_18/JK6 template to prepare humZ270VH1. The sequence between EcoRI and NheI sites is synthesized and cloned into pJSV002-hIgG4 S241P (human IgG4 5241P constant region in pJSV002, FIG. 3G), with CDR-encoding sequences in uppercase letters and restriction sites in bold text (FIG. 4J, SEQ ID NO:23).

Figure 5:
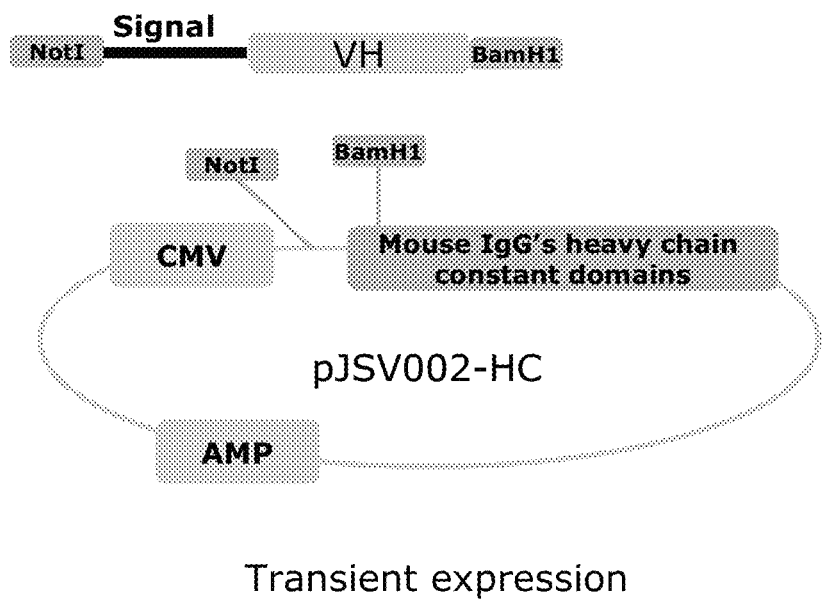
FIG. 5 shows an exemplary design of a vector for expression of humanized Z270 heavy-chains.
Figure 6:
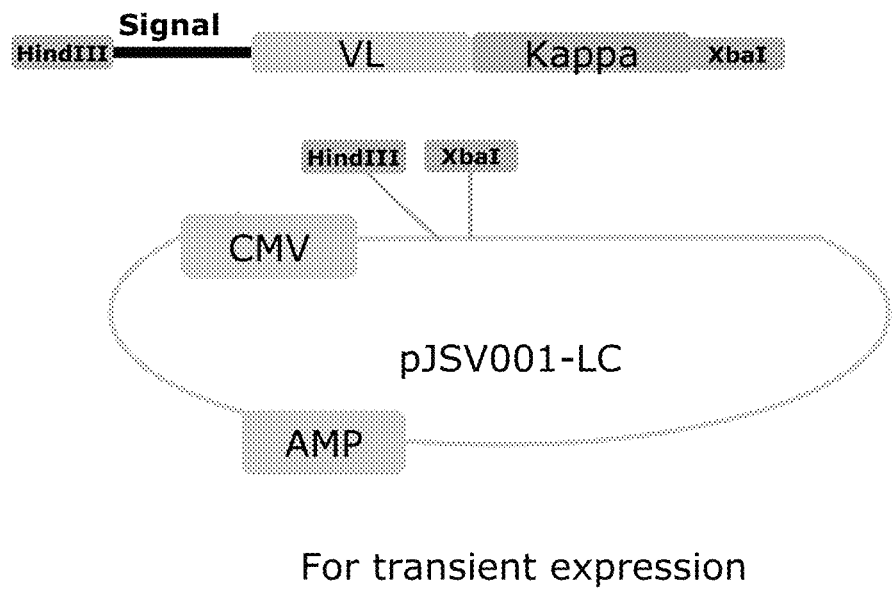
FIG. 6 shows an exemplary design of a vector for expression of humanized Z270 light-chains.

Mutated constructs are likewise cloned into pJSV002 with the corresponding IgG4 S241 P constant region and human Kappa chain constant region, with the following combinations of framework back-mutations in each of humZ270VL and humZ270VH:

humZ270VL: Wt (i.e., no back-mutation), L46F, I48V, L46F_I48V humZ270VH: Wt (i.e., no back-mutation), V5Q, M69L, T71V, T73K, T75S, V5Q_M69L, V5Q_T71V, V5Q_T73K, V5Q_T75S, M69L_T71V, M69L_T73K, M69L_T75S, T71V_T73K, T71V_T75S, T73K_T75S, V5Q_M69L_T71V_T73K_T75S, M69L_T71V_T73K_T75S, V5Q_T71V_T73K_T75S, V5Q_M69L_T73K_T75S, V5Q_M69L_T71V_T75S, V5Q_M69L_T71V_T73K, T71V_T73K_T75S, M69L_T73K_T75S, M69L_T71V_T75S, M69L_T71V_T73K, V5Q_T73K_T75S, V5Q_T71V_T75S, V5Q_T71V_T73K, V5Q_M69L_T75S, V5Q_M69L_T73K, V5Q_M69L_T71V. An exemplary vector design for the heavy chain (HC) is illustrated in FIG. 5, and an exemplary vector design for the light chain (LC) is provided in FIG. 6.

The plasmids are transfected into HEK293 6E for transient expression, using 293fectin. Materials:Cells:HEK 293 6E (293-6E) cells are grown in exponential growth phase (0.8 to 1.2×106 cells/ml). Culture Medium: FreeStyle™ (Cat. No. 12338-018 from Gibco); 25 µg/ml Geneticin 418 (Cat. No. 10131-019 from Gibco); 0.1% pluronic F-68 (Cat. No. 24040-032 from Gibco). Transfection Medium: Opti-MEM (Cat. No. 51985-026 from Gibco); 293fectin (Cat. No. 12347019 from Invitrogen). Plasmid DNA: Purified plasmid DNA of interest (see above).

Cell Count and Inoculation. Two days before transfection, the necessary volume to get $7.5 \times 10^6$ cells is transferred into a 125 ml flask, and fresh Freestyle medium is added to complete to 30 ml (final cell density should be $0.25 \times 10^6$ cells/ml). Two days later (the day of transfection), cell density should be between 1 and $1.2 \times 10^6$ cells/ml. Alternatively, one day before transfection, the necessary volume to get $1.5 \times 10^7$ cells is transferred into a 125 ml flask, and fresh Freestyle medium is added to complete to 30 ml (final cell density should be of $0.50 \times 10^6$ cells/ml). 24 h later (the day of transfection), cell density should be between 0.9 and $1.2 \times 10^6$ cells/ml.

Figure 7:
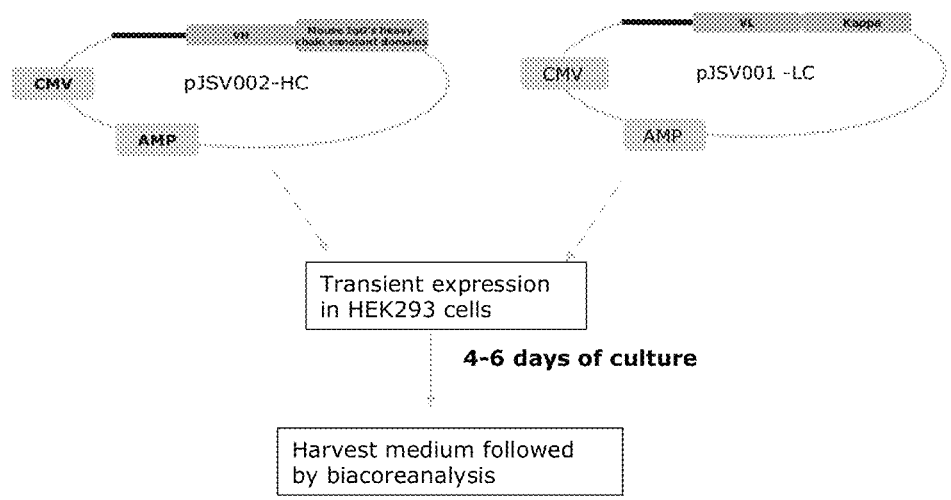
FIG. 7 shows an exemplary outline of a procedure for transient expression of humanized Z270 antibodies in HEK293 cells.

293Fectin-DNA Complexes Preparation. To prepare DNA solution, 30 µg DNA is diluted in a total volume of 1 ml Opti-MEM. To prepare 293fectin solution, 40 µl is diluted in 960 µl Opti-MEM. After 5 min. incubation at room temperature, the 293fectin solution and the DNA solution are mixed, and then incubated 25 minutes at room temperature. The cells are then transfected with 2 ml 293fectin-DNA mixture, and incubate at 37° C. in a humidified incubator (orbital shaker) containing 5% CO2 for 4 to 6 days. FIG. 7 outlines a general procedure for transient expression in HEK293 cells, such as e.g., HEK693 6E cells.

Example 6

Purification of IgG1 from Z270 Hybridoma Culture

IgG1 Z270 antibody is purified from Z270 hybridoma cell culture fluid by adding the sample onto a HiTrap Protein A HP (1 ml) column equilibrated in 3M NaCl 50 mM Tris pH8.5, at a flow rate: 1.0 ml/min, and eluting antibody using 25 mM citric acid, 4.5 mM sodium citric acid pH3.0.

Example 7

Antibody Quantification and Affinity Determination

Plasmids containing light chain and equivalent heavy chain expression constructs are mixed in pairs, and the plasmids are used to transfect HEK6E cells. The culture medium supernatant is then collected.

To quantify mouse IgG1 (or IgG4) antibody quantification, an ELISA plate is coated with Goat poly anti mouse IgG1 (or IgG4) Fc specific capture antibody. Antibody expression supernatant is applied, followed by HRP-Goat poly anti mouse kappa or Fab secondary antibody. HRP substrate is applied, and conversion detected at OD450.

Figure 8:
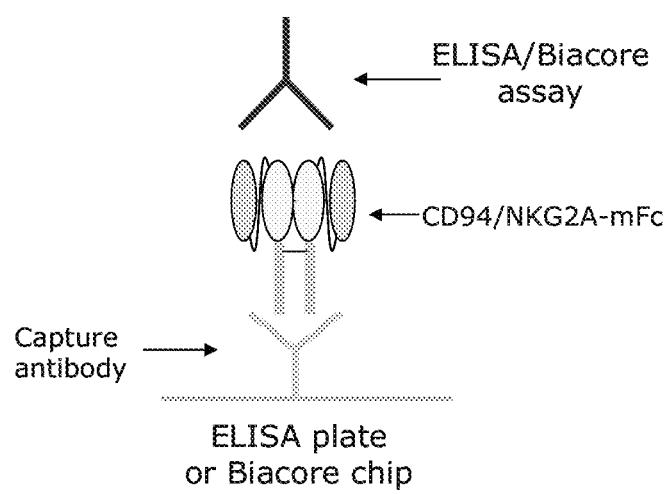
FIG. 8 shows an exemplary Biacore assay to determine humZ270 binding affinity for antigen.

To analyse antigen-binding of humanized Z270 antibodies, the following Biacore assay, illustrated in FIG. 8, is used. Antigen-capture antibody is immobilized on a Biacore chip. The antigen and culture supernatant are applied. The on- and off-rates are analyzed to calculate the affinity.

Example 8

Biacore Analysis of Chimeric, Humanized, and Back-Mutation Variants of Z270

Materials and Methods

Chimeric Z270 and humZ270 in VKI_O2/JK4 light chain and VH1_18/JH6 heavy chain acceptor frameworks were produced according to the methods described in Examples 4 and 5. The antigen-binding properties of chimeric Z270, humZ270 and back-mutation variants were analyzed on a Biacore T100 (Biacore AB, Uppsala, Sweden). The antigen was in the form of a single-chain NKG2A-CD94-mFc construct was covalently immobilized on the sensor CM5 chip (Biacore AB, Uppsala, Sweden) via amine groups using 1-ethyl-3-(3-dimethylaminopropyl)carbodiimide hydrochloride (EDC) and N-hydroxysuccinimide (NHS). The immobilization level was targeted at 300 RU. Z270 antibody variants were diluted to a concentration series (0.157, 0.313, 0.625, 1.25, 2.5 nM) in the running buffer HBS-EP (10 mM HEPES pH 7.4, 150 mM NaCl, 3 mM EDTA, 0.005% (v/v) Tween-20). All the samples were then injected over the immobilized antigen for 2 min at the flow rate of 40 ul/min. Subsequently, the running buffer was injected for 3 min at 40 ul/min for antibody dissociation analysis. After each run, the regeneration buffer (10 mM NaOH, 500 mM NaCl) was injected (30 seconds, 10 ul/min) to completely strip the remaining antibodies off the antigen. Data were evaluated with Biacore T100 evaluation software.

Results

Figure 9A:
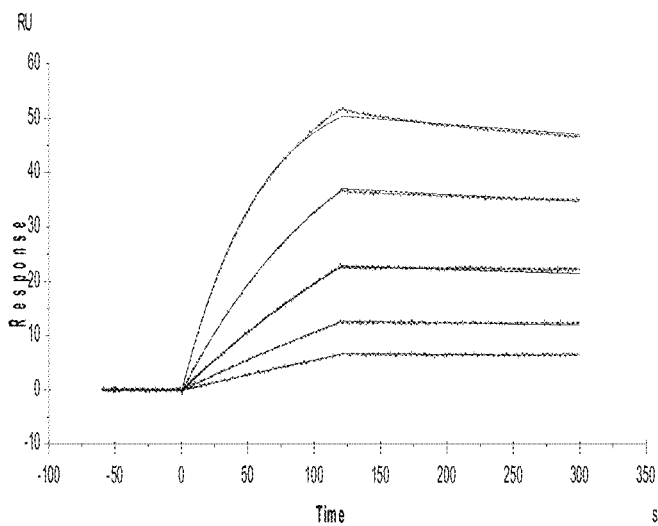
FIGS. 9A-9B show affinity determinations of chimeric Z270 (A) and humZ270VL1/VH1 (B).
Figure 9B:
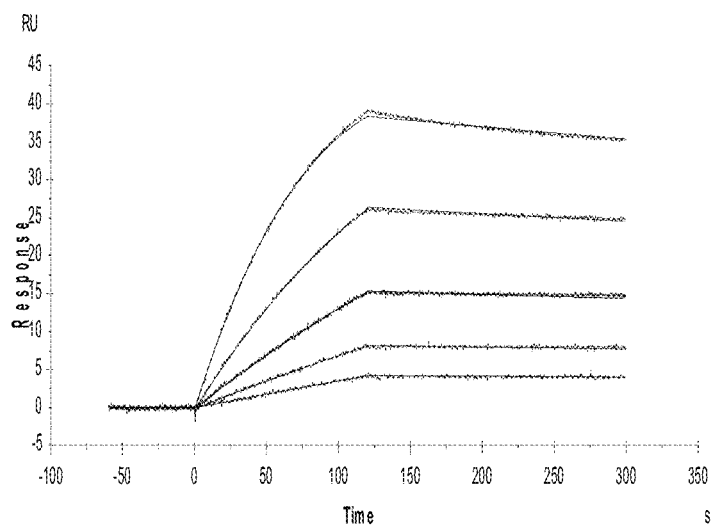
Figure 10:
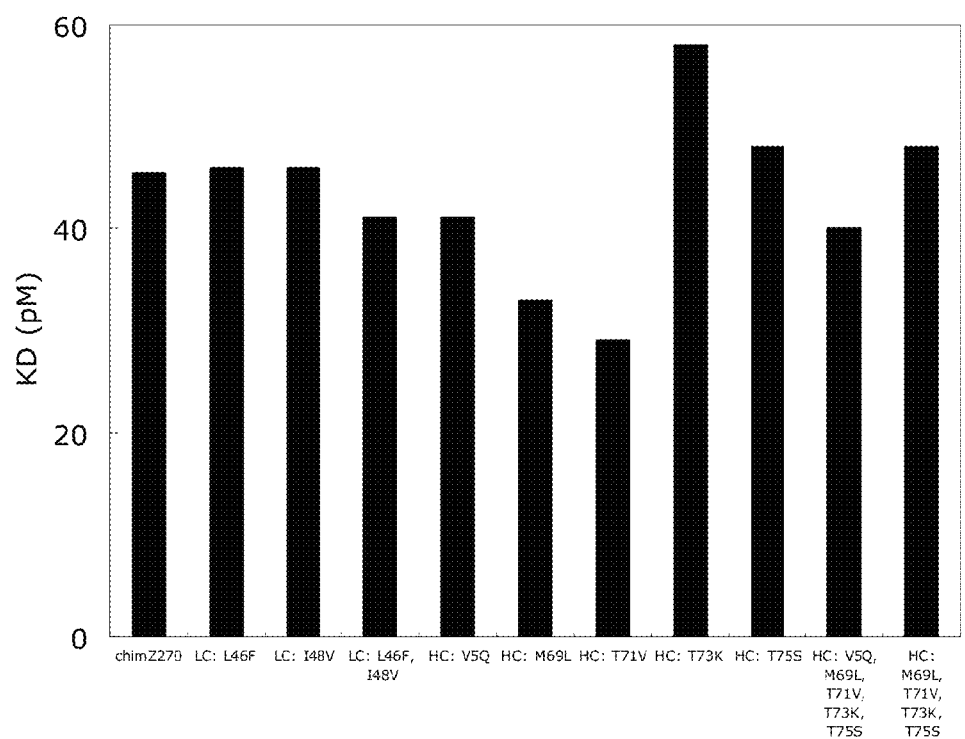
FIG. 10 shows affinity determination of humZ270VL1/VH1, having different back-mutations in the light chain or heavy chain. Chimeric Z270 was used as a comparison.

The affinity of humZ270 was determined as 67 µM. This KD value was higher than that of chimeric Z270 (50 µM) (FIG. 9 and Table 2). Introduction of back mutations to humZ270 in VKI_O2/JK4 light chain and VH1_18/JH6 heavy chain acceptor frameworks did not substantially improve its affinity (FIG. 10).

TABLE 2

| Chimeric Z270 | | | | humZ270 | | | |
|---|---|---|---|---|---|---|---|
| ka (1/Ms) | kd (1/s) | KD (M) | Chi$^2$ (RU$^2$) | ka (1/Ms) | Kd (1/s) | KD (M) | Chi$^2$ (RU$^2$) |
| 7.970E+6 | 3.972E−4 | 4.983E−11 | 0.0968 | 7.492E+6 | 4.982E−4 | 6.650E−11 | 0.044 |

Example 9

Generation of humZ270 with Full-Length CDR-H2

In an alternative strategy, shown in FIG. 11, it was investigated whether full-length Kabat CDRs (including a full-length CDR-H2) would result in an improved affinity of humZ270 in VKI_O2/JK4 light chain and VH1_18/JH6 heavy chain acceptor frameworks. humZ270VH3 (SEQ ID NO:24) follows directly from the difference in CDR definitions, resulting basically in a Kabat CDR-grafted humanized Z270 antibody. humZ270VH4 (SEQ ID NO:25) follows from the observation that K38, Q46, W47, I48, G49, Y59, Q61, K62, K66, and A67 are in proximity to S60, F63, K64, D65 side-chains, resulting in a CDR-grafted humanized Z270 antibody with R38K, E46Q, M48I, R66K, and V67A back-mutations.

Example 10

Generation of humZ270 in Other Human Acceptor Frameworks

A number of different humanized constructs with different human heavy chain acceptor framework sequences were made to explore the framework choice.

FIG. 12 shows an alignment between the different humanized Z270VH constructs prepared. humZ270VH5 (SEQ ID NO:26) is based on VH5_a, humZ270VH6 (SEQ ID NO:27) is based on VH5_51, humZ270VH7 (SEQ ID NO:28) is based on VH1_f, and humZ270VH8 (SEQ ID NO:29) is based on VH1_46, all with a JH6 J-segment. The 6 C-terminal amino acid residues of the Kabat CDR-H2 of all humanized constructs were identical to the human acceptor framework.

Using the alignment program Vector NTI, the following sequence identities between humZ270VH1 and humZ270VH5, -6, -7, and -8 were obtained: 78.2% (VH1 vs. VH5), 79.0% (VH1 vs. VH6), 88.7% (VH1 vs. VH7), and 96.0% (VH1 vs. VH8).

Example 11

Biacore Analysis of Different humZ270 Variants

Figure 13:
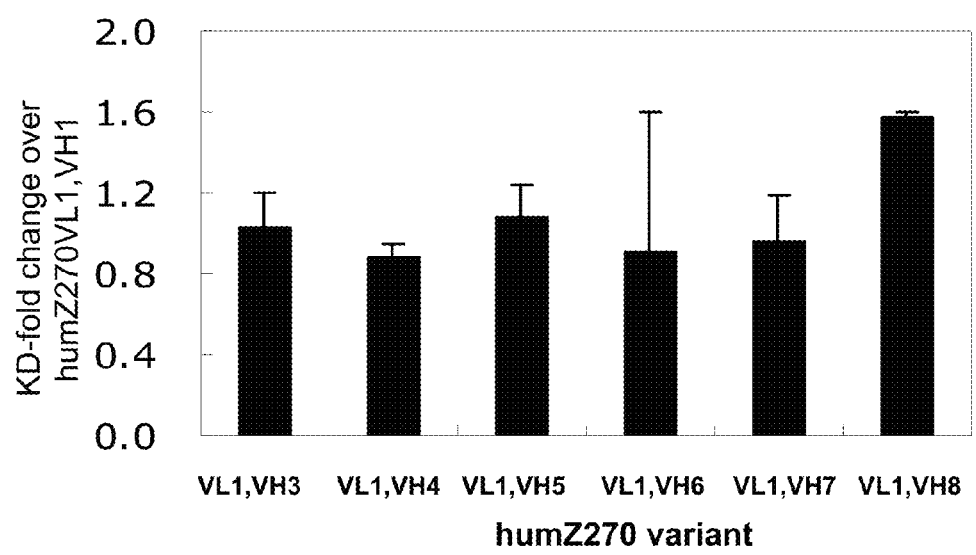
FIG. 13 shows the results of Biacore affinity evaluation of humZ270 variantsVL1/VH1 and VH3-VH8, all normalized to the KD of hZ270VL1/VH1.

The affinities of huZ270 variants, all comprising a humZ270VL1 sequence but with different strategies employed for VH sequence humanization, were analyzed.
Materials and Methods A Biacore T100 (Biacore AB, Uppsala, Sweden) was used. CD94/NKG2A antigen was used in the form of a single-chain NKG2A -CD94-mFc construct, covalently immobilized on the sensor CM5 chip (Biacore AB, Uppsala, Sweden) via amine groups using 1-ethyl-3-(3-dimethylaminopropyl) carbodiimide hydrochloride (EDC) and N-hydroxysuccinimide (NETS). The immobilization level was targeted at 300 RU. humZ270 antibody variants were diluted to a concentration series (0.157, 0.313, 0.625, 1.25, 2.5 nM) in the running buffer HBS-EP. All the samples were then injected over the immobilized antigen for 2 min at the flow rate of 40 ul/min. Subsequently, the running buffer was injected for 3 min at 40 ul/min for antibody dissociation analysis. After each run, the regeneration buffer (10 mM NaOH, 500 mM NaCl) was injected (40 seconds, 10 ul/min) to completely strip the remaining antibodies off the antigen. Data were evaluated with Biacore T100 evaluation software. The KD value of each variant was divided by that of huZ270 with a humZ270VH1 heavy chain to obtain the relative KD fold change.
Results and Conclusions The results are shown in FIG. 13, where the KD value of each variant was normalized to that of huZ270 with a humZ270VH1 heavy chain to obtain the relative change in KD. As shown in FIG. 13, there were no significant difference between the CDR-grafted variants (VH3, VH4) and the humZ270 variant comprising fewer murine residues in the CDR-H2 segment, (humZ270VL1/VH1). Nor were there substantial differences between the "humanized-CDR-H2" variants in different human acceptor frameworks. Since a more human humZ270 antibody has the benefit of a lower risk for an immunogenic response in human patients, the humanized-CDR-H2 variants such as VH1, VH5, VH6, and VH7 can be chosen for therapeutic applications without the compromise of a significantly lower affinity as compared to a standard CDR-grafted humZ270 antibody, and with a lower likelihood of a host immune response.

Example 12

Identification of Critical Residues in Z270VL and VH

In order to identify the paratope of Z270, alanine scan mutagenesis was conducted on the CDRs of the murine antibody. The following amino acids were selected for alanine mutagenesis (FIG. 14):

Z270VL: R24A, S26A, E27A, N28A, Y30A, S31A, N50A, K52A, T53A, E56A, Y92A, T94A

Figure 15:
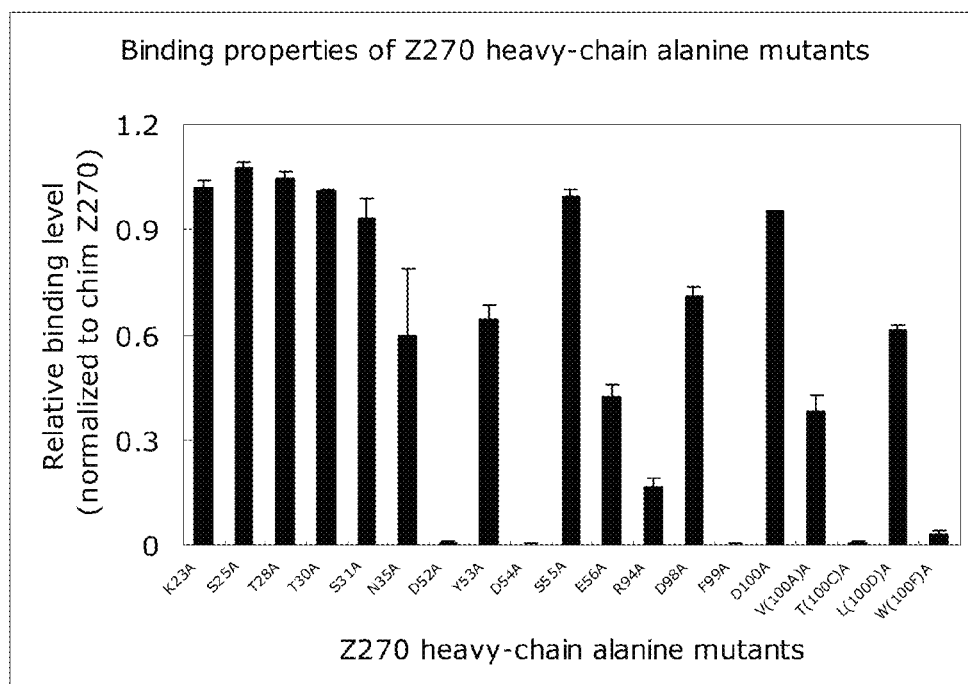
FIG. 15 shows the results of Biacore affinity evaluation of Z270VH alanine mutants, normalized to the binding of chimeric Z270.
Figure 16:
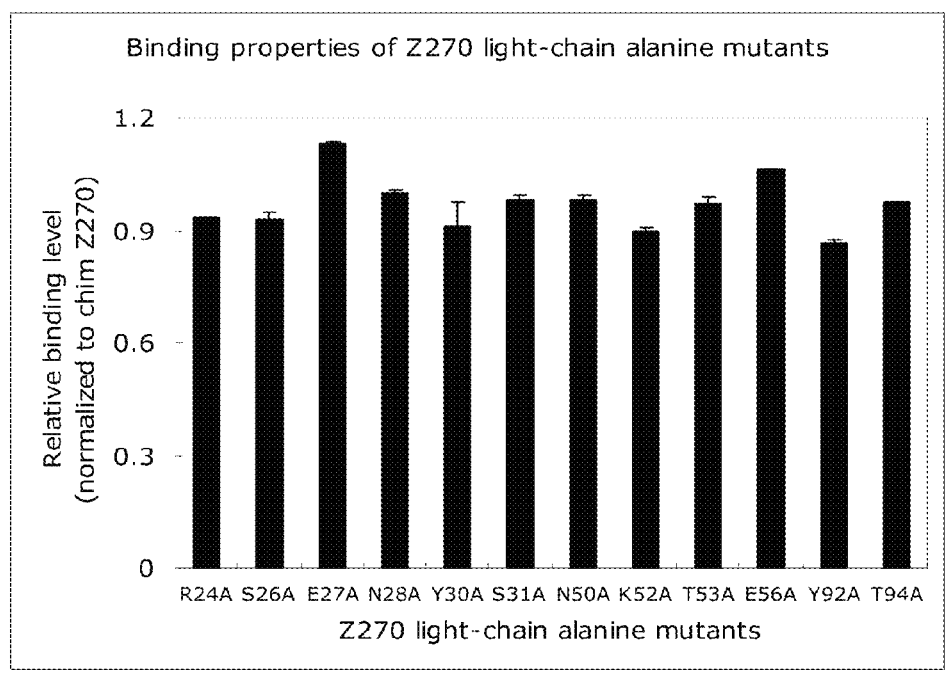
FIG. 16 shows the results of Biacore affinity evaluation of Z270VL alanine mutants, normalized to the binding of chimeric Z270.

Z270VH: K23A, S25A, T28A, T30A, S31A, N35A, D52A, Y53A, D54A, S55A, E56A, R94A, D98A, F99A, D100A, V(100A)A, T(100C)A, L(100D)A, W(100F)A, D101A. Materials and Methods The antigen-binding properties of the alanine mutants were analyzed on a Biacore T100 (Biacore AB, Uppsala, Sweden). Antigen in the form of sc-NKG2A-CD94-mFc was covalently immobilized on the sensor CM5 chip (Biacore AB, Uppsala, Sweden) via amine groups using 1-ethyl-3-(3-dimethylaminopropyl) carbodiimide hydrochloride (EDC) and N-hydroxysuccinimide (NHS). The immobilization level was targeted at 300 RU. Purified Z270 alanine mutants were diluted to 0.75 nM or 1.5 nM in the running buffer HBS-EP. All the samples were then injected over the immobilized antigen for 3 min at the flow rate of 10 ul/min. Subsequently, the running buffer was injected for 1 min at 10 ul/min for antibody binding stability analysis. After each run, the regeneration buffer (10 mM NaOH, 500 mM NaCl) was injected (35 seconds, 10 ul/min) to completely strip the remaining antibodies off the antigen. Data were evaluated with Biacore T100 evaluation software. The relative binding of each mutant was calculated through dividing its binding level (RU) obtained from Biacore by that of chimZ270.
Results and Conclusions As shown in FIG. 15, Z270VH alanine mutants D52A, D54A, F99A, T(100C)A, and W(100F)A completely lost their antigen-binding properties. The heavy-chain mutant R94 remained around 20% antigen-binding ability. The relative binding levels of heavy-chain mutants N35A, Y53A, E56A, D98A, V(100A)A, and L(100D)A were between 40-70% (FIG. 1). Accordingly, the amino acids D52, D54, R94, F99, T(100C), and W(100F) in the Z270 heavy chain CDR-H2 and CDR-H3 are the critical residues to recognize the antigen. Meanwhile, the amino acids N35, Y53, E56, D98, V(100A), and L(100D) in the heavy chain moderately affect the antigen-binding. Interestingly, all Z270 light-chain alanine mutants retain comparable antigen-binding properties to that of chimeric Z270 (FIG. 16). Therefore, no amino acid in the Z270 light chain significantly contributes to antigen recognition.

Example 13

HumZ270 Specifically Binds Cells Expressing CD94/NKG2A

The strength and specificity of humZ270 binding to CD94/NKG2A was tested in flow-cytometry, by analyzing the binding of in HEK293 cells produced wild-type Z270 (recZ270), chimeric Z270 with human IgG4 (chimZ270) or humanized Z270 (humZ270VL1/VH1) to Ba/F3 cells stably over-expressing either CD94/NKG2A or CD94/NKG2C. For this purpose, Ba/F3-CD94/NKG2A and —C cells were incubated with various concentrations of Z270 variants in tissue-culture medium containing 2% FCS, for at least 30 minutes on ice. Subsequently cells were washed, and the cells incubated in similar medium with APC conjugated secondary Ab's, again for at least 30 minutes on ice. After two times washing with ice-cold PBS, the binding of mAb's to cells was visualized using a BD Biosciences FACSarray.

Figure 17:
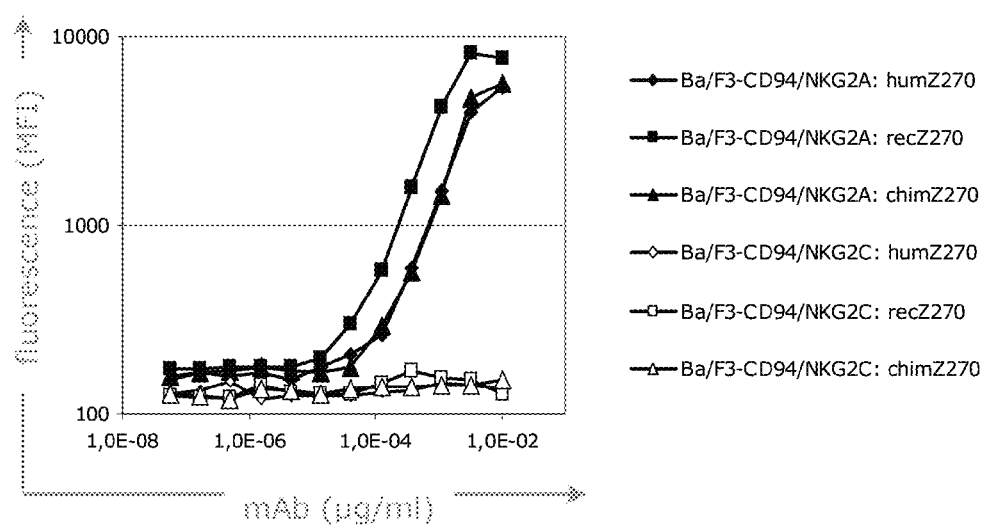
FIG. 17 shows the binding of various recombinant Z270 variants to Ba/F3 cells stably over-expressing either CD94/NKG2A or CD94/NKG2C, using flow-cytometry.

As shown in FIG. 17, all Z270 variants bind in a dose-dependent fashion to Ba/F3-CD94/NKG2A cells, but not to Ba/F3-CD94/NKG2C cells. Thus all variants specifically bind NKG2A, with humZ270 binding with similar efficacy to NKG2A as chimZ270, whereas recZ270 binds slightly more efficiently.

Example 14 humZ270 Induces Killing of HLA-E+Target Cells by CD94/NKG2A-Expressing NKL Cells The ability of recZ270, chimZ270, humZ270VL1/VH1 and Z199 to induce killing of $^{51}$Cr-labeled LCL 721.221-Cw3 cells by CD94/NKG2A+NKL cells was investigated. In this assay, $^{51}$Cr-labeled LCL 721.221-Cw3 target-cells (HLA-E+) were incubated with NKL cells in a humidified incubator containing 5% $CO_2$, for 4 hours at 37° C. (E:T ratio =6:1), in the presence or absence of various concentrations of anti-NKG2A mAb's. The killing of target-cells was analyzed by measuring the amount of $^{51}$Cr in the tissue-culture medium, which was released by target cells upon killing.

Figure 18:
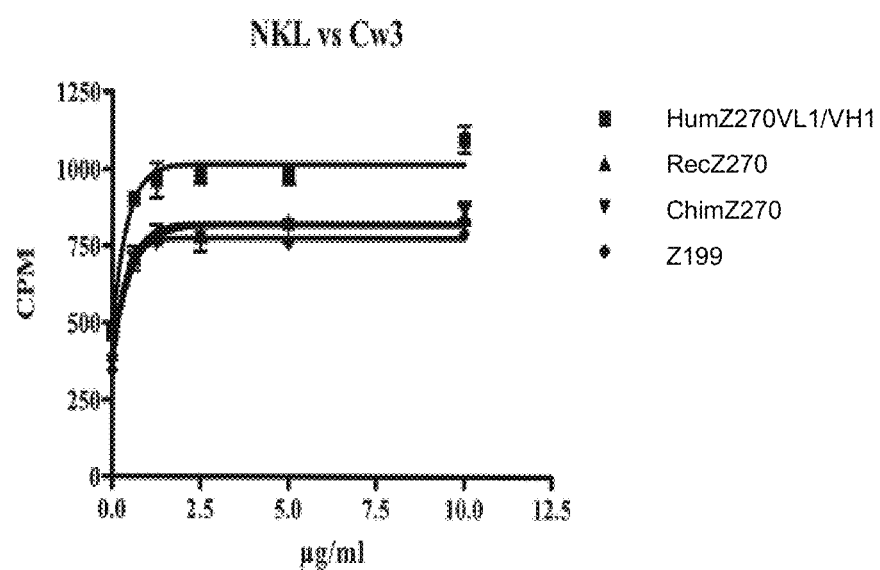
FIG. 18 shows the results of an assay to evaluate the ability of recombinant Z270, chimeric Z270, humZ270VL1/VH1, and Z199 to induce killing of $^{51}$Cr-labeled LCL 721.221-Cw3 cells by CD94/NKG2A+NKL cells, showing that humZ270VL1/VH1 was more efficient in inducing killing.

In FIG. 18, it shown that increasing concentrations of anti-NKG2A antibody induced the killing of LCL 721.221-Cw3 cells by NKL cells. Z199, chimZ270 and recZ270 were all equally efficient, whereas humZ270 induced higher killing of LCL 721.221-Cw3 cells by NKL cells. Thus, humZ270 can efficiently block the inhibitory function of CD94/NKG2A on CD94/NKG2A-expressing cytotoxic lymphocytes, such as subsets of NK-cells, NKT-cells, α/β T-cells and γ/δ T-cells, and was more efficient than the other recombinant variants tested.

Example 15 humZ270 is a Competitive CD94/NKG2A Antagonist

To test whether humZ270VL1/VH1 prevents ligand (i.e. HLA-E) binding to CD94/NKG2A, we analyzed whether humZ270 could prevent the binding of HLA-E tetramers to CD94/NKG2A over-expressing Ba/F3 cells (Ba/F3-CD94/NKG2A). For this, Ba/F3-CD94/NKG2A were incubated with 1) various concentrations of humZ270 or 2) first incubated with a saturing concentration of HLA-E tetramers (4.7 μg/ml) and then incubated with various concentrations of humZ270. All incubations were performed in tissue-culture medium containing 2% FCS, on ice. Subsequently, cells were incubated with APC-conjugated secondary antibodies specific for mouse Ab's, and analyzed by flowcytometry using a BD Biosciences FACSarray.

Figure 19:
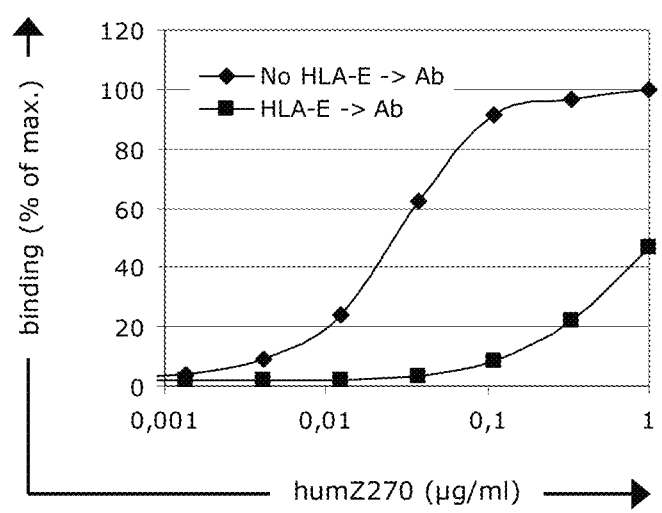
FIG. 19 shows that humZ270VL1/VH1 efficiently binds Ba/F3-CD94/NKG2A cells in a concentration dependent fashion (diamonds). However, when cells were pre-incubated with HLA-E tetramers, humZ270VL1/VH1 was prevented from binding to Ba/F3-CD94/NKG2A cells (squares).

As shown in FIG. 19, humZ270 efficiently binds Ba/F3-CD94/NKG2A cells in a concentration dependent fashion (diamonds). However, when cells were pre-incubated with HLA-E tetramers, humZ270 was prevented from binding to Ba/F3-CD94/NKG2A cells. Thus HumZ270 and HLA-E bind overlapping epitopes on CD94/NKG2A. Therefore, the CD94/NKG2A-inhibitory effect of humZ270 in NK-cytotoxicity assays is likely a consequence of preventing the ability of HLA-E inducing negative signals to cytotoxic lymphocytes via CD94/NKG2A. As such, humZ270 can be considered a competitive CD94/NKG2A antagonist.

Example 16 humZ270 Specifically Binds to CD94/NKG2A

The specificity and efficacy of humZ270VL1/VH1, and various humZ270VL1/VH1 variants with back-mutations in the variable light (VL) or variable heavy (VH) regions were tested for binding to CD94/NKG2A in flow-cytometry. For this, Ba/F3-CD94/NKG2A cells were incubated with humZ270-L46F (VL), humZ270-I48V (VL), humZ270-L46F/I48V (VL), humZ270-V5Q (VH), humZ270-M69L (VH), humZ270-T71V (VH), humZ270-T73K (VH), humZ270-T75S (VH), humZ270-V5Q/M69L/T71V/T73K/T75S (VH), humZ270-M69L/T71V/T73K/T75S (VH) or two different batches of humZ270VL1/VH1 without back-mutations ("DK" and "CHN"). For this purpose, Ba/F3-CD94/NKG2A or —C cells were incubated with various concentrations of the humZ270 variants in tissue-culture medium containing 2% FCS, for at least 30 minutes on ice. The cells were then washed, and incubated in similar medium with APC conjugated secondary antibodies specific for human antibodies, again for at least 30 minutes on ice. After two times washing with ice-cold PBS, the binding of secondary antibodies to cells was visualized using a BD Biosciences FACSarray.

Figure 20:
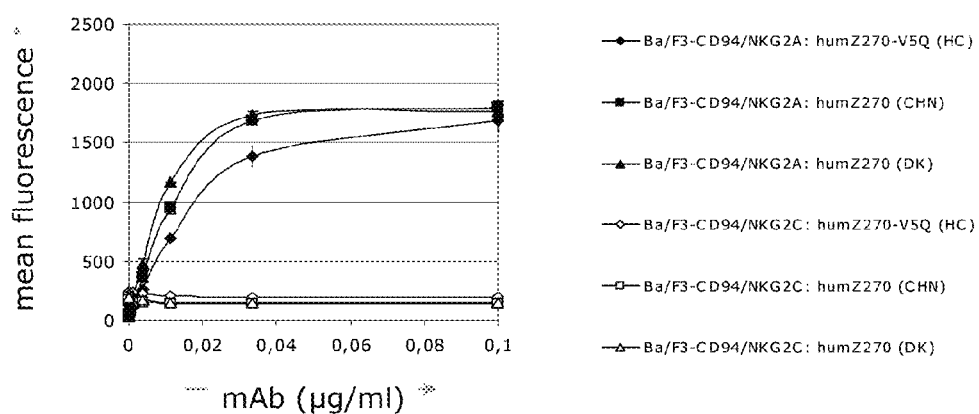
FIG. 20 shows that two different preparations of humZ270VL1/VH1 and a humZ270 variant with a V5Q mutation in VH bind to CD94/NKG2A- but not CD94/NKG2C-expressing cells, though the V5Q-variant slightly less efficiently.

All variants bound specifically to CD94/NKG2A, and not to CD94/NKG2C. All variants bound with similar efficacy to CD94/NKG2A, with the exception of variants containing the V5Q (VL) mutation, which bound slightly less efficiently (see FIG. 20).

EXEMPLARY EMBODIMENTS

The following paragraphs describe exemplary embodiments of the invention.

1. An antibody that specifically binds NKG2A, comprising antigen-binding residues from the complementarity-determining regions (CDRs) of murine antibody Z270 and human acceptor framework sequences, wherein at least the 6 C-terminal amino acid residues of the CDR-H2 are the same as those in the variable heavy (VH) human acceptor sequence.

2. The antibody of embodiment 1, which is more effective than an antibody comprising murine antibody Z270 variable light (VL) and VH sequences in potentiating the cytotoxic activity of a CD94/NKG2A-expressing cytotoxic lymphocyte.

3. The antibody of embodiment 1, which is more effective than an antibody comprising murine antibody Z270 variable light (VL) and VH sequences in neutralizing the inhibitory activity of a CD94/NKG2A receptor expressed on the surface of a cytotoxic lymphocyte.

4. The antibody of embodiment 1, which is more effective than an antibody comprising murine antibody Z270 variable light (VL) and VH sequences in reducing CD94/NKG2A-mediated inhibition of the cytotoxic activity of a CD94/NKG2A-expressing cytotoxic lymphocyte.

5. The antibody of embodiment 1, which is more effective than an antibody comprising murine antibody Z270 variable light (VL) and VH sequences in inducing the killing of a Cw3-expressing target cell by a CD94/NKG2A-expressing cytotoxic lymphocyte.

6. The antibody of any of embodiments 2-5, wherein the CD94/NKG2A-expressing cytotoxic lymphocyte is an NK cell, an NKT cell, an α/β T-cell, or a γ/δ T-cell.

7. The antibody of embodiment 6, wherein the CD94/NKG2A-expressing cytotoxic lymphocyte is an NK cell.

8. The antibody of any of embodiments 1-7, wherein the antibody VH domain comprises residues D52, D54, F99, T(100C), and W(100F) from the VH CDRs of murine antibody Z270.

9. The antibody of embodiment 8, wherein the antibody VH domain further comprises residues N35, Y53, E56, D98, V(100A), and L(100D) from the VH CDRs of murine antibody Z270.

10. The antibody of any of embodiments 1-9, comprising a CDR-H1 corresponding to residues 31-35 of SEQ ID NO:5 and a CDR-H3 corresponding to residues 95-102 of SEQ ID NO:5, wherein the CDR-H2 comprises residues 50-59 of SEQ ID NO:5.

11. The antibody of any of embodiments 1-10, wherein the VH domain human acceptor framework has 70% or more sequence identity to SEQ ID NO:5.

12. The antibody of any of embodiments 1-11, wherein the VH segment of the VH human acceptor framework is VH1_18, VH5_a, VH5_51, VH1_f, or VH1_46, and the J-segment is JH6.

13. The antibody of embodiment 12, wherein the VH segment is VH1_18, VH5_a, VH5_51, or VH1_f.

14. The antibody of embodiment 13, wherein the VH segment is VH1_18.

15. The antibody of any of embodiments 1-14, wherein the VH domain human acceptor sequence is free of any back-mutations.

16. The antibody of any of embodiments 1-14, wherein
    (a) the amino acid at position 5 of the VH domain is V or Q;
    (b) the amino acid at position 69 of the VH domain is M or L;
    (c) the amino acid at position 71 of the VH domain is T or V;
    (d) the amino acid at position 73 of the VH domain is T or K; or
    (e) the amino acid at position 75 of the VH domain is T or S.

17. The antibody of embodiment 16, wherein the amino acid at position 69 is L.

18. The antibody of embodiment 16, wherein the amino acid at position 71 is V.

19. The antibody of any of embodiments 1-15, wherein the VH domain comprises the sequence of SEQ ID NO:5.

20. The antibody of any of embodiments 1-19, comprising a CDR-L1 corresponding to residues 24-34 of SEQ ID NO:4, a CDR-L2 corresponding to residues 50-56 of SEQ ID NO:4, and a CDR-L3 corresponding to residues 89-97 of SEQ ID NO:4.

21. The antibody of embodiment 20, wherein the VL domain human acceptor sequence is free of any back-mutations.

22. The antibody of any of embodiments 20-21, wherein the VL domain human acceptor framework is from VKI_O2/JK4.

23. The antibody of any of embodiments 20-22, wherein the VL domain human acceptor framework comprises SEQ ID NO:4.

24. A humanized antibody or antibody fragment that specifically binds NKG2A, comprising
    (a) a CDR-L1 corresponding to residues 24-34 of SEQ ID NO:4;
    (b) a CDR-L2 corresponding to residues 50-56 of SEQ ID NO:4;
    (c) a CDR-L3 corresponding to residues 89-97 of SEQ ID NO:4;
    (d) a CDR-H1 corresponding to residues 31-35 of SEQ ID NO:5;
    (e) a CDR-H3 corresponding to residues 95-102 of SEQ ID NO:5; and
    (f) a CDR-H2 comprising residues 50-59 of SEQ ID NO:5; and
    (g) human acceptor framework sequences;
    wherein residues 60-65 in the CDR-H2 are from the VH human acceptor sequence, and
    wherein the humanized antibody is more effective than an antibody comprising a variable light (VL) sequence corresponding to SEQ ID NO:1 and a VH sequences corresponding to SEQ ID NO:2 in potentiating the cytotoxic activity of a CD94/NKG2A-expressing NK cell.

25. A humanized antibody that binds human NKG2A, the antibody comprising a VH domain that comprises non-human CDR residues and a human VH acceptor framework, the VH domain comprising a CDR-H1 corresponding to residues 31-35 of SEQ ID NO:5, a CDR-H2 corresponding to residues 50-65 of SEQ ID NO:5, and a CDR-H3 corresponding to residues 95-102 of SEQ ID NO:5.

26. The humanized antibody of embodiment 25, wherein the human VH accepfor framework does not comprise any back-mutation.

27. The humanized antibody of embodiment 25, wherein the amino acid at Kabat position 5 of the VH domain is V or Q.

28. The humanized antibody of embodiment 25, wherein the amino acid at Kabat position of the VH domain 69 is M or L.

29. The humanized antibody of embodiment 25, wherein the amino acid at Kabat position 71 of the VH domain is T or V.

30. The humanized antibody of embodiment 25, wherein the amino acid at Kabat position 73 of the VH domain is T or K.

31. The humanized antibody of embodiment 25, wherein the amino acid at Kabat position 75 of the VH domain is T or S.

32. The humanized antibody of embodiment 25, wherein the VH domain comprises a framework region substitution in at least one Kabat position selected from the group consisting of 5, 69, 71, 73, and 75.

33. The humanized antibody of embodiment 32, wherein the VH domain comprises the amino acid sequence of SEQ ID NO:5, with framework substitutions according to any one of the following options:
    (a) none
    (b) V5Q
    (c) M69L
    (d) T71V
    (e) T73K
    (f) T75S
    (g) V5Q and M69L
    (h) V5Q and T71V
    (i) V5Q and T73K
    (j) V5Q and T75S
    (k) M69L and T71V
    (l) M69L and T73K
    (m) M69L and T75S
    (n) T71V and T73K
    (o) T71V and T75S
    (p) T73K and T75S
    (q) V5Q, T73K and T75S
    (r) V5Q, T71V and T75S
    (s) V5Q, T71V and T73K
    (t) V5Q, M69L and T75S
    (u) V5Q, M69L and T73K
    (v) V5Q, M69L and T71V
    (w) T71V, T73K and T75S
    (x) M69L, T73K and T75S (y) M69L, T71V and T75S,
(z) M69L, T71V and T73K,
(aa) V5Q, M69L, T71V and T73K,
(bb) V5Q, M69L, T71V and T75S,
(cc) V5Q, M69L, T73K and T75S,
(dd) V5Q, T71V, T73K and T75S,
(ee) M69L, T71V, T73K and T75S, and
(ff) V5Q, M69L, T71V, T73K and T75S.

34. The humanized antibody of any of embodiments 25-32, comprising a VL domain that comprises non-human CDR residues incorporated into a human VL acceptor framework, the VL domain comprising a CDR-L1 corresponding to residues 24-34 of SEQ ID NO:4, a CDR-L2 corresponding to residues 50-56 of SEQ ID NO:4, and an CDR-L3 corresponding to residues 89-97 of SEQ ID NO:4.

35. The humanized antibody of embodiment 34, wherein the human VL acceptor framework does not comprise any back-mutation.

36. The humanized antibody of embodiment 34, wherein the amino acid at Kabat position 46 of the VL domain is L or F.

37. The humanized antibody of embodiment 34, wherein the amino acid at Kabat position 48 of the VL domain is I or V.

38. The humanized antibody of embodiment 34, wherein the VL domain comprises a framework region substitution in at least one Kabat position selected from 46 and 48.

39. The humanized antibody of embodiment 38, wherein the VL domain comprises the amino acid sequence of SEQ ID NO:4, with framework substitutions according to any one of the following options:
(a) None
(b) L46F
(c) I48V
(d) L46 and I48V.

40. A humanized antibody that binds human NKG2A, the antibody comprising a VH domain that comprises non-human CDR residues incorporated into a human VH domain, the VH domain comprising a framework region substitution in at least one Kabat position in SEQ ID NO:7 selected from the group consisting of 5, 69, 71, 73, and 75.

41. The humanized antibody of embodiment 40, comprising a V5Q substitution.

42. The humanized antibody of embodiment 40, comprising a M69L substitution.

43. The humanized antibody of embodiment 40, comprising a T71V substitution.

44. The humanized antibody of embodiment 40, comprising a T73K substitution.

45. The humanized antibody of embodiment 40, comprising a T75S substitution.

46. The humanized antibody of embodiment 40, comprising a VL domain that comprises non-human CDR residues incorporated into a human VL domain, the VL domain comprising a framework region substitution in at least one Kabat position in SEQ ID NO:6 selected from 46 and 48.

47. The humanized antibody of embodiment 40, comprising a L46F substitution.

48. The humanized antibody of embodiment 40, comprising a I48V substitution.

49. The humanized antibody of any of embodiments 40-48, comprising a CDR-H1 corresponding to residues 31-35 of SEQ ID NO:5, a CDR-H2 corresponding to residues 50-66 of SEQ ID NO:5, and a CDR-H3 corresponding to residues 95-102 of SEQ ID NO:5.

50. The humanized antibody of any of embodiments 40-49, comprising a VH domain comprising the sequence of SEQ ID NO:7.

51. The humanized antibody of any of embodiments 40-50, comprising a CDR—L1 corresponding to residues 24-34 of SEQ ID NO:6, a CDR-L2 corresponding to residues 50-56 of SEQ ID NO:6, and an CDR-L3 corresponding to residues 89-97 of SEQ ID NO:6.

52. The humanized antibody of any of embodiments 40-52, comprising a VL domain comprising the sequence of SEQ ID NO:6.

53. A humanized antibody that binds human NKG2A, the antibody comprising a VH domain that comprises the amino acid sequence of SEQ ID NO:5, optionally with one or more FR substitutions at Kabat positions 5, 69, 71, 73, and/or 75.

54. The humanized antibody of embodiment 53, wherein the optional FR substitutions are V5Q, M69L, T71V, T73K, and/or T75S.

55. The humanized antibody of embodiment 52, further comprising a VL do—main that comprises the amino acid sequence of SEQ ID NO:4, optionally with one or more FR substitutions at Kabat positions 46 and/or 48.

56. The humanized antibody of embodiment 55, wherein the optional FR sub—stitutions are L46F and/or I48V.

57. A humanized antibody that binds NKG2A, comprising a VH domain that comprises non-human CDR residues incorporated into a human VH domain, wherein the VH domain is at least 50% identical to SEQ ID NO:5.

58. The humanized antibody of embodiment 46, wherein the VH domain is at least 90% identical to SEQ ID NO:5.

59. The humanized antibody of any of embodiments 57 and 58, comprising a CDR-H1 corresponding to residues 31-35 of SEQ ID NO:5, a CDR-H2 corresponding to resi— dues 50-66 of SEQ ID NO:5, and a CDR-H3 corresponding to residues 95-102 of SEQ ID NO:5.

60. The humanized antibody of any of embodiments 57-59, comprising a V or Q at Kabat position 5, an M or L at Kabat position 69, a T or V at Kabat position 71, a T or K at Kabat position 73, and a T or S at Kabat position 75, in the VH domain.

61. The humanized antibody of any of embodiments 57-60, comprising a VL domain that comprises non-human CDR residues incorporated into a human VL domain, wherein the VL domain is at least 50% identical to SEQ ID NO:4.

62. The humanized antibody of any of embodiments 57-61, comprising a VL domain at least 90% identical to SEQ ID NO:4.

63. The humanized antibody of any of embodiments 57-62, comprising a CDR-L1 sequence corresponding to residues 24-34 of SEQ ID NO:4, a CDR-L2 sequence corresponding to residues 50-56 of SEQ ID NO:4, and an CDR-L3 sequence corresponding to residues 89-97 of SEQ ID NO:4.

64. The humanized antibody of any of embodiments 57-63, comprising a L or F at Kabat position 46 and/or an I or V at Kabat position 48.

65. A humanized antibody that binds human NKG2A, the antibody comprising a VH domain that comprises non-human CDR residues incorporated into a human VH domain, the VH domain comprising a CDR-H1 corresponding to residues 31-35 of SEQ ID NO:8, a CDR-H2 corresponding to residues 50-66 of SEQ ID NO:8, and a CDR-H3 corresponding to residues 95-102 of SEQ ID NO:8, wherein the amino acids at Kabat positions 63, 64, 65, 66, and 67 are F, K, D, K, A, respectively.

66. The humanized antibody of embodiment 65, wherein the amino acid at Kabat position 60 is A.

67. The humanized antibody of any of embodiments 65 and 66, wherein the VH domain comprises the amino acid sequence of SEQ ID NO:8.

68. The humanized antibody of any of embodiments 65-67, further comprising a VL domain comprising a CDR-L1 corresponding to residues 24-34 of SEQ ID NO:6, a CDR-L2 corresponding to residues 50-56 of SEQ ID NO:6, and an CDR-L3 corresponding to residues 89-97 of SEQ ID NO:6.

69. The humanized antibody of any of embodiments 65-68, wherein the VL domain comprises the amino acid sequence of SEQ ID NO:6.

70. A humanized version of an anti-NKG2A antibody produced by the Z270 hybridoma.

71. The antibody of any of embodiments 1-70, which is a multispecific antibody or an antibody fragment.

72. The antibody of embodiment 71, which is an antibody fragment selected from a Fab, a Fab', a F(ab)$_2$, a F(ab')$_2$, a F(ab)$_3$, an Fv, a single-chain Fv, a dsFv, an Fd fragment, a dAb fragment, a minibody, a diabody, a triabody, a tetrabody, a kappa body; a camel IgG; an IgNAR; and a multispecific antibody fragment.

73. The antibody of embodiment 72, which is a bispecific antibody.

74. The antibody of any of embodiments 1-70, which is a full-length IgG4 antibody or fragment thereof.

75. The antibody of embodiment 74, wherein the heavy-chain constant domain comprises an S241P mutation.

76. An isolated nucleic acid encoding the antibody of any of the preceding embodiments.

77. A vector comprising the nucleic acid of embodiment 76.

78. A host cell comprising the vector of embodiment 76.

79. A method of producing an antibody comprising culturing the host cell of embodiment 78 so that the nucleic acid is expressed and the antibody produced.

80. The method of embodiment 79, further comprising recovering the antibody from the host cell culture.

81. The method of embodiment 79 wherein, before culturing, the host cell is co-transfected with a vector comprising nucleic acid encoding a variable heavy domain and with a vector comprising nucleic acid encoding a variable light domain.

82. An immunoconjugate comprising an antibody according to any of embodiments 1-75 and a second agent.

83. The immunoconjugate of embodiment 82, wherein the second agent is a cytotoxic agent.

84. The immunoconjugate of embodiment 82, wherein the second agent is a PEG-molecule.

85. A pharmaceutical composition comprising the antibody of any of embodiments 1-75 or the immunoconjugate of any of embodiments 82-84, and a carrier.

86. The pharmaceutical composition of embodiment 74, comprising a buffer selected from citrate, phosphate, and a combination thereof, having a pH from about 6.0 to about 7.5.

87. An article of manufacture comprising a container containing the antibody of any of embodiments 1-75 and instructions directing a user to treat a disorder selected from a cancer, a viral disease, an inflammatory disorder, and an autoimmune disorder, in a mammal with the antibody in an effective amount.

88. The article of embodiment 87, wherein the mammal is a human.

89. The antibody of any of embodiments 1-75 for use in neutralizing the inhibitory activity of a CD94/NKG2A receptor expressed on the surface of a cytotoxic lymphocyte in a human patient.

90. The antibody of any of embodiments 1-75 for use in reducing CD94/NKG2A-mediated inhibition of the cytotoxicity activity of a CD94/NKG2A-expressing cytotoxic lymphocyte in a human patient.

91. The antibody of any of embodiments 1-75 for use in potentiating the cytotoxic activity of a CD94/NKG2A-expressing cytotoxic lymphocyte in a human patient.

92. The antibody of any of embodiments 1-75 for use in inducing the killing of a Cw3-expressing target cell by a CD94/NKG2A-expressing cytotoxic lymphocyte in a human patient.

93. The antibody of any embodiments 89-92, wherein the CD94/NKG2A-expressing cytotoxic lymphocyte is an NK cell, an NKT cell, an α/β T-cell, or a γ/δ T-cell.

94. A method of treating a human patient suffering from a disorder selected from a cancer, a viral disease, an inflammatory disorder, and an autoimmune disorder, comprising administering the pharmaceutical composition of any of embodiments 85-86.

95. The use of the antibody of any of embodiments 1-75 in the preparation of a medicament for administration to a human patient suffering from a disorder selected from a cancer, a viral disease, an inflammatory disorder, and an autoimmune disorder.

96. The antibody of any of embodiments 1-75 for use in the treatment of a human patient suffering from a disorder selected from a cancer, a viral disease, an inflammatory disorder, and an autoimmune disorder.

97. The method, use, or antibody of any of embodiments 89-96, wherein the patient suffers from squamous cell carcinoma, leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, Burkitt's lymphoma, multiple myeloma, acute or chronic myelogenous leukemias, promyelocytic leukemia, fibrosarcoma, rhabdomyosarcoma; melanoma, seminoma, teratocarcinoma, neuroblastoma, glioma, astrocytoma, neuroblastoma, schwannomas; fibrosarcoma, rhabdomyosarcoma, osteosarcoma, melanoma, xeroderma pigmentosum, keratoacanthoma, seminoma, thyroid follicular cancer, teratocarcinoma, other carcinoma of the bladder, breast, colon, kidney, liver, lung, ovary, prostate, pancreas, stomach, cervix, thyroid or skin, other hematopoietic tumors of lymphoid lineage, other hematopoietic tumors of myeloid lineage, other tumors of mesenchymal origin, other tumors of the central or peripheral nervous system, or other tumors of mesenchymal origin.

98. The use according to embodiment 97, wherein the patient suffers from multiple myeloma, Non-Hodgkin's lymphoma, or acute myelogeous lymphoma.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way, Any combination of the above-described elements in all possible variations thereof is encompassed by the invention unless otherwise indicated herein or otherwise clearly contradicted by context.

Unless otherwise expressly indicated or clearly contradicted by context, the term "or" herein is used in the inclusive sense of "and/or", and, accordingly, as implicitly providing support for an embodiment or aspect in which the term is to be interpreted in the exclusive sense of "either this or that".

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

We claim:

1. A method of treating a human patient suffering from a cancer, the method comprising administering to the human patient a non-depleting antibody or antigen binding fragment thereof that specifically binds NKG2A or a pharmaceutical composition comprising said antibody or antigen binding fragment, wherein the antibody comprises antigen-binding residues from the complementarity-determining regions (CDRs) of murine antibody Z270 and human acceptor framework sequences, wherein said antibody comprises a VL domain that is at least 90% identical to SEQ ID NO: 4 and a VH domain that is at least 90% identical to SEQ ID NO: 5, and wherein said antibody comprises CDR-H1 corresponding to residues 31-35 of SEQ ID NO: 5, CDR-H2 corresponding to residues 50-60 of SEQ ID NO: 5, CDR-H3 corresponding to residues 99-114 of SEQ ID NO: 5, CDR-L1 corresponding to residues 24-34 of SEQ ID NO: 4, CDR-L2 corresponding to residues 50-56 of SEQ ID NO: 4 and CDR-L3 corresponding to residues 89-97 of SEQ ID NO: 4.

2. The method of claim 1, wherein:
the amino acid at position 5 of the VH domain is V or Q;
the amino acid at position 70 of the VH domain is M or L;
the amino acid at position 72 of the VH domain is T or V;
the amino acid at position 74 of the VH domain is T or K; or
the amino acid at position 76 of the VH domain is T or S.

3. The method of claim 1, wherein the VH domain human acceptor framework sequences of said antibody are free of any back-mutations.

4. The method of claim 1, wherein the VH domain of said antibody comprises the sequence of SEQ ID NO: 5.

5. The method of claim 1, wherein the VL domain of said antibody comprises SEQ ID NO: 4.

6. The method of claim 1, wherein the antibody is an IgG4 antibody.

7. The method of claim 1, wherein said antibody is an antigen binding fragment or a multispecific antibody.

8. The method according to claim 1, wherein said cancer is selected from the group consisting of bladder cancer, breast cancer, colon cancer, kidney cancer, liver cancer, lung cancer, ovary cancer, prostate cancer, pancreatic cancer, stomach cancer, cervical cancer, thyroid cancer, skin cancer, leukemia, acute lymphocytic leukemia, chronic lymphocytic leukemia, acute lymphoblastic leukemia, B-cell lymphoma, T-cell lymphoma, Hodgkin's lymphoma, non-Hodgkin's lymphoma, hairy cell lymphoma, Burkitt's lymphoma, multiple myeloma, acute and chronic myelogenous leukemias, promyelocytic leukemia, myelodysplastic syndrome, fibrosarcoma, rhabdomyosarcoma, melanoma, seminoma, neuroblastoma, astrocytoma, neuroblastoma, glioma, schwannomas, osteosarcoma, xeroderma pigmentosum, keratoacanthoma, thyroid follicular cancer and teratocarcinoma.

9. The method of claim 1, wherein the antibody is a humanized antibody that:
a) specifically binds to NKG2A,
b) does not specifically bind to an Fc receptor, and
c) when bound to NKG2A on a human NK cell, causes said NK cell to lyse a target human cell bearing HLA-E on the target cell surface, when said target cell comes into contact with said NK cell.

10. The method of claim 1, wherein the antibody is Fab or F(ab')2 fragment.

11. The method of claim 1, wherein the antibody comprises a modified Fc portion, which is modified to minimize or eliminate binding to Fc receptors.

12. The method of claim 1, wherein said cancer is cervical cancer.

13. The method of claim 1, wherein said cancer is leukemia or lymphoma.

14. The method of claim 1, wherein said cancer cells express HLA-E.

* * * * *

UNITED STATES PATENT AND TRADEMARK OFFICE
CERTIFICATE OF CORRECTION

PATENT NO. : 9,683,041 B2
APPLICATION NO. : 14/548327
DATED : June 20, 2017
INVENTOR(S) : Petrus Johannes Louis Spee and Soeren B. Padkaer Page 1 of 2

It is certified that error appears in the above-identified patent and that said Letters Patent is hereby corrected as shown below:

In the Specification

Column 12,
Line 11, "VH1J" should read --VH1_f--.

Column 14,
Line 21, "A605" should read --A60S--.

Column 14,
Line 36, "A605" should read --A60S--.

Column 14,
Line 62, "560A" should read --S60A--.

Column 14,
Line 64, "560A" should read --S60A--.

Column 23,
Line 24, "5 μg/m1" should read --5 μg/ml--.

Column 23,
Line 28, "IFN-γproduction" should read --IFN-γ production--.

Column 23,
Line 50, "culturfing" should read --culturing--.

Column 24,
Line 44, "2p" should read --2μ--.

Signed and Sealed this
Third Day of April, 2018

Andrei Iancu
*Director of the United States Patent and Trademark Office*

CERTIFICATE OF CORRECTION (continued)
U.S. Pat. No. 9,683,041 B2

Column 42,
Line 23, "(SWFI)" should read --(BWFI)--.

Column 45,
Line 21, "WTY" should read --VVTY--.

Column 45,
Line 52, "10PG" should read --1OPG--.

Column 46,
Line 9, "VH1 f" should read --VH1_f--.

Column 48,
Lines 10-11, "pJSV002-IgG4-5241P" should read --pJSV002-IgG4-S241P--.

Column 48,
Line 37, "S241 P" should read --S241P--.

Column 50,
Line 28, "(50 μM)" should read --(50 pM)--.

Column 51,
Line 25, "NKG2A -CD94-mFc" should read --NKG2A-CD94-mFc--.

Column 51,
Line 29, "(NETS)." should read --(NHS).--.

Column 53,
Line 12, "CD94/NKG2A+NKL" should read --CD94/NKG2A+ NKL--.

Column 56,
Line 19, "accepfor" should read --acceptor--.